United States Patent [19]
Thorner et al.

[11] Patent Number: 5,852,187
[45] Date of Patent: *Dec. 22, 1998

[54] MOLECULAR CLONING OF THE OVINE PITUITARY GROWTH HORMONE RELEASING HORMONE RECEPTOR

[75] Inventors: Michael O. Thorner, North Garden; Bruce D. Gaylinn, Trevilians, both of Va.; Reiko Horikawa, Tokyo, Japan; Charles E. Lyons, Jr., Charlottesville, Va.

[73] Assignee: The University of Virginia Patent Foundation, Charlottesville, Va.

[*] Notice: The term of this patent shall not extend beyond the expiration date of Pat. No. 5,644,046.

[21] Appl. No.: 660,963

[22] Filed: Jun. 12, 1996

Related U.S. Application Data

[63] Continuation-in-part of Ser. No. 902,826, Jun. 23, 1992, and a continuation-in-part of Ser. No. 432,043, May 1, 1995, Pat. No. 5,644,046.

[51] Int. Cl.$^6$ ............................ C12N 15/12; C12N 15/10; C07K 14/72
[52] U.S. Cl. ...................... 536/23.5; 536/23.1; 435/69.1; 435/6; 435/91.2; 530/350
[58] Field of Search ................... 536/23.5, 23.1; 435/6, 69.1, 91.2; 530/350, 399

[56] References Cited

U.S. PATENT DOCUMENTS

| | | | |
|---|---|---|---|
| 5,583,010 | 12/1996 | Baumbach et al. | 435/69.1 |
| 5,591,641 | 1/1997 | Thorner et al. | 435/69.1 |
| 5,612,470 | 3/1997 | Thorner et al. | 536/23.5 |
| 5,644,046 | 7/1997 | Thorner et al. | 536/23.5 |

FOREIGN PATENT DOCUMENTS

| | | |
|---|---|---|
| 591697 | 4/1994 | European Pat. Off. . |
| 604244 | 6/1994 | European Pat. Off. . |
| 94/00482 | 1/1994 | WIPO . |
| 94/07915 | 4/1994 | WIPO . |

OTHER PUBLICATIONS

Hashimoto et al., Identification of alternatively spliced messenger ribonucleic acid encoding truncated growth hormone-releasing hormone receptor in human pituitary adenomas, J. Clin. Endocrinol., 80(10):2933–2939, 1995.

Tang et al., Identification of human growth hormone-releasing hormone receptor splicing variants, J. Clin. Endocrinol., 80(8): 2381–2387, 1995.

Hsuing et al., Structure and functional expression of a complementary DNA for porcine growth hormone-releasing hormone receptor, Neuropeptides, 25: 1–10, 1993.

Lin et al., Pit–1 dependent expression of the receptor for growth hormone releasing factor mediates pituitary cell growth, Nature, 360: 765–768, Dec. 1992.

Gaylinn et al., Photoaffinity cross-linking to the pituitary receptor for growth hormone-releasing factor, Endocrinol., 135(3): 950–955, 1994.

Wu et al., The effect of GH-releasing peptide-2 (GHRP-2 or KP 102) on GH secretion from primary cultured ovine pituitary cells can be abolished by specific GH-releasing factor (GRF) receptor antagonist, J. Endocrinol., 140: R9–13, 1994.

Lin et al., Molecular basis of the little mouse phenotype and implications for cell type-specific growth, Nature, 364: 208–213, Jul. 1993.

*Primary Examiner*—Stephen Walsh
*Assistant Examiner*—Claire M. Kaufman
*Attorney, Agent, or Firm*—Burns, Doane, Swecker & Mathis, L.L.P.

[57] ABSTRACT

Growth hormone releasing hormone (GHRH) receptor binding has been characterized using a unique binding assay utilizing iodinated GHRH probes. Photoaffinity GHRH probes have been constructed which allow for photolabeling and characterization of the receptor. In addition, high affinity biotinylated GHRH analogs have been constructed. Solubilization of GHRH-R/GHRH complexes and extraction of specifically bound GHRH using a mild detergent solution, followed by affinity chromatography, leads to a substantially purified GHRH-R isolate. Electrophoretic treatment of the GHRH-R isolate produces GHRH-R of sufficient purity to conduct sequencing of the receptor. Cloning of a gene encoding for polypeptides (protein or fragments thereof) having GHRH-R activity is accomplished using a bacterial host, and the cloned gene is expressed in a mammalian cell line. In addition, molecular cloning of the ovine GHRH-R is provided.

3 Claims, 27 Drawing Sheets

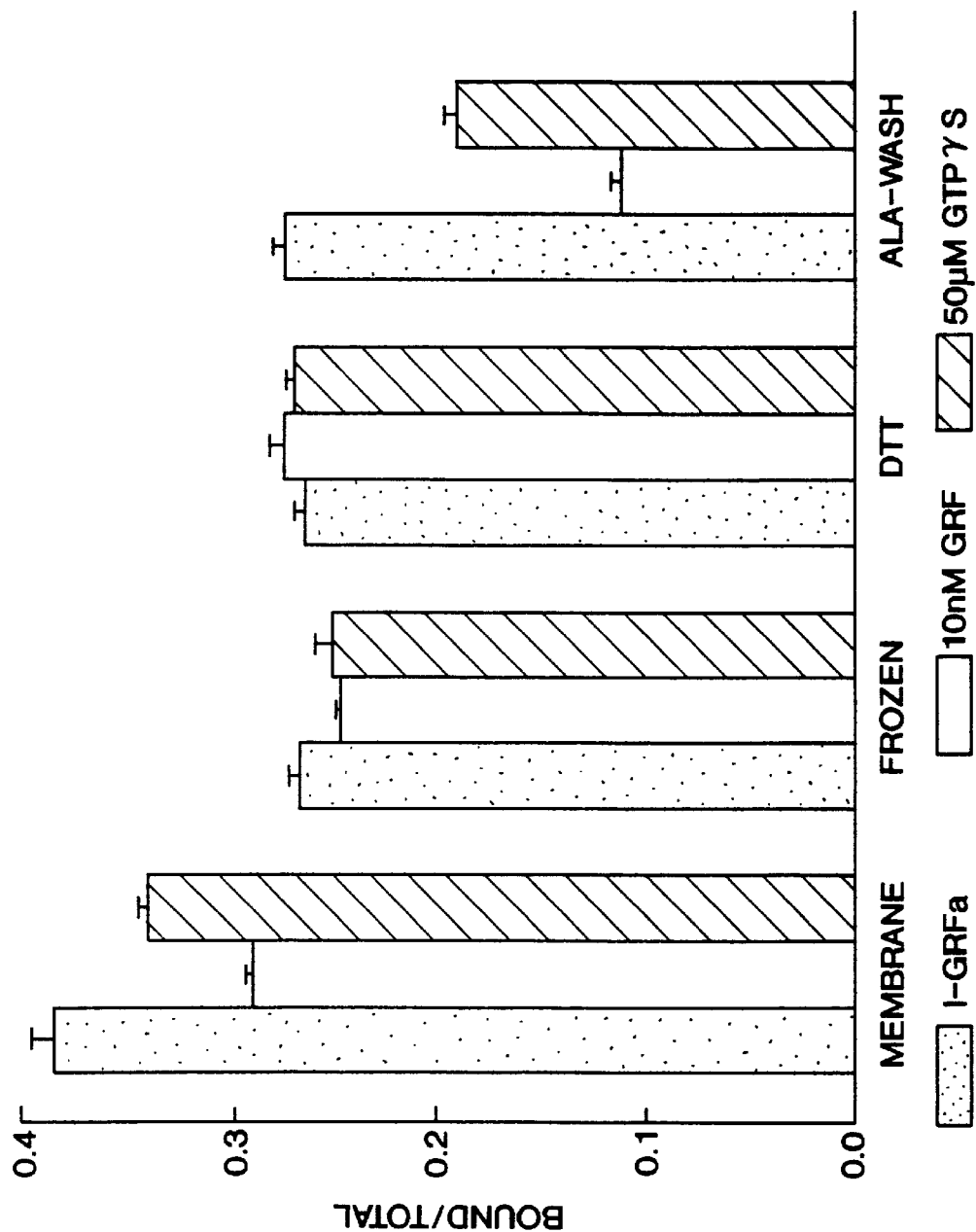

Deglycosylation of Photo-affinity Crosslinked Receptor

Photoaffinity Crosslinking with Deglycosylation

BLUESCRIPT PLASMID CONTAINING 1.6 kbp INSERT OF HAP 7.3

COM8 EXPRESSION VECTOR PLASMID CONTAINING HAP 7.3

Ovine GHRH Receptor cDNA Sequence and Encoded Protein

```
        cggcacgagtctctctctctctctctctctctctctctctctcctcgtgccgaattcg
     1  ------------+---------+---------+---------+---------+---------+  60
        gccgtgctcagagagagagagagagagagagagagagagagagaggagcacggcttaagc a        R  H  E  S  L  S  L  S  L  S  L  S  L  L  V  P  N  S   - gcacgagctggcagcagtgacaacaggggacggtggaaggagcacagggccaccgaggct
    61  ------------+---------+---------+---------+---------+---------+  120
        cgtgctcgaccgtcgtcactgttgtccctgccaccttcctcgtgtcccggtggctccga a        A  R  A  G  S  S  D  N  R  G  R  W  K  E  H  R  A  T  E  A   - gacccaggcagccgtcgccgagctcccaccatgggcagcagggtgtggggcgcctgcgtc
   121  ------------+---------+---------+---------+---------+---------+  180
        ctgggtccgtcggcagcggctcgagggtggtacccgtcgtcccacacccgcggacgcag a        D  P  G  S  R  R  R  A  P  T  M  G  S  R  V  W  G  A  C  V   - ctctgcttgctgggccccttgccaatcgtcctgggccacgtgcacccagagtgtgatgtc
   181  ------------+---------+---------+---------+---------+---------+  240
        gagacgaacgacccggggaacggttagcaggacccggtgcacgtgggtctcacactacag a        L  C  L  L  G  P  L  P  I  V  L  G  H  V  H  P  E  C  D  V   - atcactcagctgagagaggacgagcaagcatgtctacaagctgctgaagggatgcccaac
   241  ------------+---------+---------+---------+---------+---------+  300
        tagtgagtcgactctctcctgctcgttcgtacagatgttcgacgactttccctacgggttg a        I  T  Q  L  R  E  D  E  Q  A  C  L  Q  A  A  E  G  M  P  N   - tccaccttgggctgccccaggatctgggacgggctgctgtgctggccgatggcaggctct
   301  ------------+---------+---------+---------+---------+---------+  360
        aggtggaacccgacggggtcctagaccctgcccgacgacacgaccggctaccgtccgaga a        S  T  L  G  C  P  R  I  W  D  G  L  L  C  W  P  M  A  G  S   - ggagagtgggtgagcctcccctgcccggctttcttctctcacttcagcttggagccaggg
   361  ------------+---------+---------+---------+---------+---------+  420
        cctctcacccactcggaggggacgggccgaaagaagagagtgaagtcgaacctcggtccc a        G  E  W  V  S  L  P  C  P  A  F  F  S  H  F  S  L  E  P  G   - gctgtgaagagggactgcaccattgcaggctggtcggagcccttcccgccttatcccgag
   421  ------------+---------+---------+---------+---------+---------+  480
        cgacacttctccctgacgtggtaacgtccgaccagcctcgggaagggcggaatagggctc a        A  V  K  R  D  C  T  I  A  G  W  S  E  P  F  P  P  Y  P  E   -
```

FIG. 19A

```
        gcctgccctgtgcccctggagctgctgactgaggagaaatcctacttctccgcggtaagg
    481 ----------+----------+----------+----------+----------+----------+ 540
        cggacgggacacggggacctcgacgactgactcctcttttaggatgaagaggcgccattcc
a       A  C  P  V  P  L  E  L  L  T  E  E  K  S  Y  F  S  A  V  R    - atcgtctacaccatgggccacagcgtctcggctgcagccctcctagtggccatcatcatc
    541 ----------+----------+----------+----------+----------+----------+ 600
        tagcagatgtggtacccggtgtcgcagagccgacgtcgggaggatcaccggtagtagtag
a       I  V  Y  T  M  G  H  S  V  S  A  A  A  L  L  V  A  I  I  I    - ctggtcgctctcaggaggctccactgccccaggaactacatccacacccagctgttcacc
    601 ----------+----------+----------+----------+----------+----------+ 660
        gaccagcgagagtcctccgaggtgacggggtccttgatgtaggtgtgggtcgacaagtgg
a       L  V  A  L  R  R  L  H  C  P  R  N  Y  I  H  T  Q  L  F  T    - acctttatcctcaaggcggcagctgtgttcctgaaggacgccaccctctttcaccgggag
    661 ----------+----------+----------+----------+----------+----------+ 720
        tggaaataggagttccgccgtcgacacaaggacttcctgcggtgggagaaagtggccctc
a       T  F  I  L  K  A  A  A  V  F  L  K  D  A  T  L  F  H  R  E    - aacatggaccactgcagcttctccactgtcctgtgcaaggcttctgtgaccgcctctcat
    721 ----------+----------+----------+----------+----------+----------+ 780
        ttgtacctggtgacgtcgaagaggtgacaggacacgttccgaagacactggcggagagta
a       N  M  D  H  C  S  F  S  T  V  L  C  K  A  S  V  T  A  S  H    - ttcgcgaccatgaccaacttcagctggctgctggcagaagctgtgtacctgacctgcctc
    781 ----------+----------+----------+----------+----------+----------+ 840
        aagcgctggtactggttgaagtcgaccgacgaccgtcttcgacacatggactggacggag
a       F  A  T  M  T  N  F  S  W  L  L  A  E  A  V  Y  L  T  C  L    - ttagcctccacattgcccagcacaaggagggtcttctggtggctggttctcgctgcctgg
    841 ----------+----------+----------+----------+----------+----------+ 900
        aatcggaggtgtaacgggtcgtgttcctcccagaagaccaccgaccaagagcgacggacc
a       L  A  S  T  L  P  S  T  R  R  V  F  W  W  L  V  L  A  A  W    - gggcttcctctgctcttcaccagcatgtgggtgggttgcaagttggcctttgaagatgtt
    901 ----------+----------+----------+----------+----------+----------+ 960
        cccgaaggagacgagaagtggtcgtacacccacccaacgttcaaccggaaacttctacaa
a       G  L  P  L  L  F  T  S  M  W  V  G  C  K  L  A  F  E  D  V    - gcgtgctgggacctggacgacagctcccctactggtggatcatcaaaggacccatcgtc
    961 ----------+----------+----------+----------+----------+----------+ 1020
        cgcacgaccctggacctgctgtcgaggggatgaccacctagtagtttcctgggtagcag
a       A  C  W  D  L  D  D  S  S  P  Y  W  W  I  I  K  G  P  I  V    -
```

FIG. 19B

```
       ctctctgttggggtgaactttgggcttttctcaatattatccgtatcctgctgaggaaa
  1021 ---------+---------+---------+---------+---------+---------+ 1080
       gagagacaaccccacttgaaacccgaaaaagagttataataggcataggacgactccttt a       L   S   V   G   V   N   F   G   L   F   L   N   I   I   R   I   L   L   R   K    - ctggagccaactcagggcagcctccacacccagcctcagtactggcgtctctctaagtca
  1081 ---------+---------+---------+---------+---------+---------+ 1140
       gacctcggttgagtcccgtcggaggtgtgggtcggagtcatgaccgcagagagattcagt a       L   E   P   T   Q   G   S   L   H   T   Q   P   Q   Y   W   R   L   S   K   S    - acgcttctcctcattccgctgtttggaatccactatgtcattttcaacttcctgcctgac
  1141 ---------+---------+---------+---------+---------+---------+ 1200
       tgcgaagaggagtaaggcgacaaaccttaggtgatacagtaaaagttgaaggacggactg a       T   L   L   I   P   L   F   G   I   H   Y   V   I   F   N   F   L   P   D    - agtgctgggctggacatccgcctccccctagaactgggactgggctctttccagggcttc
  1201 ---------+---------+---------+---------+---------+---------+ 1260
       tcacgacccgacctgtaggcggaggggatcttgaccctgacccgagaaaggtcccgaag a       S   A   G   L   D   I   R   L   P   L   E   L   G   L   G   S   F   Q   G   F    - attgttgctatcctgtactgcttcctcaaccaagaggtgaggactgagatctcacggaga
  1261 ---------+---------+---------+---------+---------+---------+ 1320
       taacaacgataggacatgacgaaggagttggttctccactcctgactctagagtgcctct a       I   V   A   I   L   Y   C   F   L   N   Q   E   V   R   T   E   I   S   R   R    - tggcacggccacgatcctgaacttctgccagcccggaggactcatatcaagtgaggactc
  1321 ---------+---------+---------+---------+---------+---------+ 1380
       accgtgccggtgctaggacttgaagacggtcgggcctcctgagtatagttcactcctgag a       W   H   G   H   D   P   E   L   L   P   A   R   R   T   H   I   K   *   STOP gagggtgaaggtgctgacatctgtgtgttaggctggtcagagcctgcgactggagcccac
  1381 ---------+---------+---------+---------+---------+---------+ 1440
       ctcccacttccacgactgtagacacacaatccgaccagtctcggacgctgacctcgggtg acctgaacttgggcagctacctgggtctaccaccctccacagcgtcccatgggagcctca
  1441 ---------+---------+---------+---------+---------+---------+ 1500
       tggacttgaacccgtcgatggacccagatggtgggaggtgtcgcagggtaccctcggagt tgcttccacccagcacttctttcctgtctcgttcctgactctttt
  1501 ---------+---------+---------+---------+----- 1545
       acgaaggtgggtcgtgaagaaaggacagagcaaggactgagaaaa
```

FIG. 19C

```
                              T
              A               A   s
    B  H   H  1          B    B   c E D
    s  i   Bi wP          s   s   eAcM5
    s  n   pn 21          e   s   IponO
    S  f   14 6e          R   S   IoR19
    I  I   II II          I   I   IIIII
              /                       ///
      cggcacgagtctctctctctctctctctctctctctctctctcctcgtgccgaattcg
  1   ---------+---------+---------+---------+---------+---------+   60
      gccgtgctcagagagagagagagagagagagagagagagagagagaggagcacggcttaagc a       R  H  E  S  L  S  L  S  L  S  L  S  L  S  L  L  V  P  N  S    -
b          G  T  S  L  S  L  S  L  S  L  S  L  S  L  S  S  C  R  I  R -
c             A  R  V  S  L  S  L  S  L  S  L  S  L  S  P  R  A  E  F  G  -

B
                                                Bs
              F     MT           T              sp  S  H
    B    CC   n     as    T      s        B     il a Ca    B    BC
    s    Ava  Tu    ep    s B    p        s     H2 uMve    s    BMcv  s
    s    lic  s4    14    p b    4        m     K8 9niI    a    gwei  i
    S    uJ8  eH    I5    R v    C        F     A6 61JI    J    IofJ  m
    I    III  II    II    I I    I        I     II IIII    I    IIII  I
                /     /         /          /  /      /  /     /
      gcacgagctggcagcagtgacaacaggggacggtggaaggagcacagggccaccgaggct
 61   ---------+---------+---------+---------+---------+---------+  120
      cgtgctcgaccgtcgtcactgttgtccccgccaccttcctcgtgtcccggtggctccga a       A  R  A  G  S  S  D  N  R  G  R  W  K  E  H  R  A  T  E  A    -
b          H  E  L  A  A  V  T  T  G  D  G  G  R  S  T  G  P  P  R  L -
c             T  S  W  Q  Q  *  Q  Q  G  T  V  E  G  A  Q  G  H  R  G  *  -

B
                            Bs                                       T
        E   F               sp        N   F                          t
    BcS  n  C               CBil  B   1R  n                B    HCN1 h
    soc  Tu v    M       B  AvaH25  sDENalSuT          H  B   BsNHaall
    aRr  s4 i    w       b  linK8s  assclet4s          g  b   aaahecal
    JIF  eH J    o       v  uJIA6t  JaloIAyHe          a  v   nHraI8II
    III  II I    I       I  IIIIII  IIIIIIIII          I  I   IIIIIVI
      /     /        /       / ///  //  / //                      /  //
      gacccaggcagccgtcgccgagctcccaccatgggcagcagggtgtggggcgcctgcgtc
121   ---------+---------+---------+---------+---------+---------+  180
      ctgggtccgtcggcagcggctcgagggtggtacccgtcgtcccacaccccgcggacgcag a       D  P  G  S  R  R  R  A  P  T  M  G  S  R  V  W  G  A  C  V    -
b          T  Q  A  A  V  A  E  L  P  P  P  W  A  A  G  C  G  A  P  A S -
c             P  R  Q  P  S  P  S  S  H  H  G  Q  Q  G  V  G  R  L  R  P  -
```

```
                        E                               E
      B       C       M cC   S                  C     NCBcS
      s       v      BHM BbMovMNc              CAv   lvsoc    B
      a       i      ppw son5iscr              jli   aiaRr    s
      X       J      mho 1117JpiF              euJ   IJJIF    g
      I       I      III IIIIIIII              III   VIIII    I
                      /   ///  ///                    /        //
           ggagagtgggtgagcctccccgtgcccggcttctttctctcacttcagcttggagccaggg
      361  ----------+---------+---------+---------+---------+---------+  420
           cctctcacccactcggaggggacgggccgaaagaagagagtgaagtcgaaccctcggtccc a       G  E  W  V  S  L  P  C  P  A  F  F  S  H  F  S  L  E  P  G    -
    b        E  S  G  *  A  S  P  A  R  L  S  S  L  T  S  A  W  S  Q  G   -
    c         R  V  G  E  P  P  L  P  G  F  L  L  S  L  Q  L  G  A  R  G  -

B
                                                s
                                                p
      AC              CM B    BCC  C          NC B1              B
      lvEM            BM vb sC sva v          lv a2  MA  B  M F As
      wian            cm io rj mic i          ai n8  wc  c  n a va
      NJrl            ge RI De FR8 J          IJ I6  oi  g  l u aJ
      IIII            II II III III I         VI II  II  I  I I II
      ///             /     /    /              /
           gctgtgaagagggactgcaccattgcaggctggtcggagcccttcccgccttatcccgag
      421  ----------+---------+---------+---------+---------+---------+  480
           cgacacttctccctgacgtggtaacgtccgaccagcctcgggaagggcggaatagggctc a       A  V  K  R  D  C  T  I  A  G  W  S  E  P  F  P  P  Y  P  E    -
    b        L  *  R  G  T  A  P  L  Q  A  G  R  S  P  S  R  L  I  P  R   -
    c         C  E  E  G  L  H  H  C  R  L  V  G  A  L  P  A  L  S  R  G  -

B
                            s
           H  A            pE     F                                 M    S
      C   Ca  c           BlcS   Cn              H        B      B  sS   a
      vHaeS  eB   B     s2ocM  AvuMT    D        i   B    s    AsADpaBT  u
      iacIt  Ib   m    a8Rrw  li4ns     d        n   p    e    cacsAcsh  3
      Je8Iu  Iv   g    J6IFo  uJHle     e        4   m    R    iJiaIIla  A
      IIIII  II   I    IIIII  IIIII     I        I   I    I    IIIIIIII  I
       / //        /    ///    ///                                / ///
           gcctgccctgtgcccctggagctgctgactgaggagaaatcctacttctccgcggtaagg
      481  ----------+---------+---------+---------+---------+---------+  540
           cggacgggacacggggacctcgacgactgactcctctttaggatgaagaggcgccattcc a       A  C  P  V  P  L  E  L  L  T  E  E  K  S  Y  F  S  A  V  R    -
    b        P  A  L  C  C  P  W  S  C  *  L  R  R  N  P  T  S  P  R  G   -
    c         L  P  C  A  P  G  A  A  D  *  G  E  I  L  L  L  R  G  K  D  -
```

```
            NS        F              T                    MT
          AC1a      Cn  C T          s   T   EC    C      as      H
          vjau   s  vuPAvTs          Bp  s   cvB   v      ep      A i
          ael9   f  14slisp          b4  p   ois   i      I4      c n
          IPI6   c  RHtuJeR          vC  R   NR1   J      I5      i 4
          IIII   I  IIIIIII          II  I   III   I      II      I I
          ///       ///                                  /
      aacatggaccactgcagcttctccactgtcctgtgcaaggcttctgtgaccgcctctcat
  721 ---------+---------+---------+---------+---------+---------+ 780
      ttgtacctggtgacgtcgaagaggtgacaggacacgttccgaagacactggcggagagta a       N  M  D  H  C  S  F  S  T  V  L  C  K  A  S  V  T  A  S  H   -
b        T  W  T  T  A  A  S  P  L  S  C  A  R  L  L  *  P  P  L  I  -
c         H  G  P  L  Q  L  L  H  C  P  V  Q  G  F  C  D  R  L  S  F -

E              N            M F
           c                           CCsCnP    C                  A C
           oMNTC          a   B         AvapvuvT  a                 AlCv    R                D
           5nrhj          I   b         licAi4us  c                 lwji    s                d
           7luae          I   v         uJ8lJHIe  8                 uNeJ    a                e
           IIIII          I   I         IIIIIIII  I                 IIII    I                I
           ///            /   /         / / //                      ///
      ttcgcgaccatgaccaacttcagctggctgctggcagaagctgtgtacctgacctgcctc
  781 ---------+---------+---------+---------+---------+---------+ 840
      aagcgctggtactggttgaagtcgaccgacgaccgtcttcgacacatggactggacggag a       F  A  T  M  T  N  F  S  W  L  L  A  E  A  V  Y  L  T  C  L   -
b        S  R  P  *  P  T  S  A  G  C  W  Q  K  L  C  T  *  P  A  S  -
c         R  D  H  D  Q  L  Q  L  A  A  G  R  S  C  V  P  D  L  P  L -

F  E
         B   c    B                            C   D          n  cBS
         s   v    M    s       M    M  BBb     s     B   v    r  Tu osc
         p   i    n    r       n    n  sbo     i     b   i    d  s4 Rar
         M   J    l    D       l    l  lsl     m     v   J    I  eH IJF
         I   I    I    I       I    I  III     I     I   I    I  II III
                                       /
      ttagcctccacattgcccagcacaaggagggtcttctggtggctggttctcgctgcctgg
  841 ---------+---------+---------+---------+---------+---------+ 900
      aatcggaggtgtaacgggtcgtgttcctcccagaagaccaccgaccaagagcgacggacc a       L  A  S  T  L  P  S  T  R  R  V  F  W  W  L  V  L  A  A  W   -
b        *  P  P  H  C  P  A  Q  G  G  S  S  G  G  W  F  S  L  P  G  -
c         S  L  H  I  A  Q  H  K  E  G  L  L  V  A  G  S  R  C  L  G -
```

FIG. 20E

```
                    C    M              R T         N           H
                    v    b   HM         1MaES  M   1    p    C  C a
                    i    o   pw         enqaa  s   BaMNfX     v  vHe
                    J    l   ho         AlIrp  l   sIsslc     i  ial
                    I    I   II         IIIII  I   lIlpMm     R  Jel
                                                   IIIII         III
                              /               /       ///              //
               gggcttcctctgctcttcaccagcatgtgggtgggttgcaagttggcctttgaagatgtt
         901   ----------+----------+----------+----------+----------+----------+  960
               cccgaaggagacgagaagtggtcgtacacccacccaacgttcaaccggaaacttctacaa a       G  L  P  L  L  F  T  S  M  W  V  G  C  K  L  A  F  E  D  V   -
       b        G  F  L  C  S  S  P  A  C  G  W  V  A  S  W  P  L  * K  M  L -
       c         A  S  S  A  L  H  Q  H  V  G  G  L  Q  V  G  L  *  R  C  C  -

E                                     E
                              c                                     c
                              oE                       A    S       o   S
                    CM        AOcNPaBS   HBB  C        c    a       AONPa  H
                    ab        vlolpusc   issAv         Be B Bu  D   A  vllpusAis
                    co        aORau9pr   naml i        sI  s s3 p   l  a0au9chni
                    81        I9IIM6GF   4XFuJ         II  I rA n   w  I9IM6cd4m
                    II        IIIVIIII   IIIII         II  I II I   I  IIVIIIIII
                          / //// /          /                        / // //
               gcgtgctgggacctggacgacagctcccctactggtggatcatcaaaggacccatcgtc
         961   ----------+----------+----------+----------+----------+----------+ 1020
               cgcacgaccctggacctgctgtcgaggggggatgaccacctagtagtttcctgggtagcag a       A  C  W  D  L  D  D  S  S  P  Y  W  W  I  I  K  G  P  I  V   -
       b        R  A  G  T  W  T  T  A  P  P  T  G  G  S  S  K  D  P  S  S  -
       c         V  L  G  P  G  R  Q  L  P  L  L  V  D  H  Q  R  T  H  R  P -

C                        B
                                              vH                       p
                              M               ip        S       M      uD
                              n               Jh        s       n      ld
                              l               II        p       l      Oe
                              I                         I       I      II
                                  /                                        /
               ctctctgttggggtgaactttgggcttttttctcaatattatccgtatcctgctgaggaaa
        1021   ----------+----------+----------+----------+----------+----------+ 1080
               gagagacaaccccacttgaaacccgaaaaagagttataataggcataggacgactcctttt a       L  S  V  G  V  N  F  G  L  F  L  N  I  I  R  I  L  L  R  K   -
       b        S  L  L  G  * T  L  G  F  F  S  I  L  S  V  S  C  * G  N    -
       c         L  C  W  G  E  L  W  A  F  S  Q  Y  Y  P  Y  P  A  E  E  T -
```

FIG. 20F

```
                  F                                                A       H
        C N       n C                         C              T B   1B      B i
        B v1   D B  Tu  vCB          B M  vHD          RSTaMsB     wsDC    an
        s i a  d s  s4  i j p        b n  i g d        s c a g n a s   2mdJ    ec
        r J I  e l  e H  J e m       v l  J a e        a a t I l H r   6Bee    RI
        I I V  I I  I I  I I I       I I  I I I        I I I I I I I   I I I I   I I
                  /                                  //                 //
       ctggagccaactcagggcagcctccacacccagcctcagtactggcgtctctctaagtca
1081   ----------+----------+----------+----------+----------+----------+   1140
       gacctcggttgagtcccgtcggaggtgtgggtcggagtcatgaccgcagagagattcagt a       L   E  P  T   Q  G  S   L  H  T   Q  P  Q   Y  W  R   L  S  K   S    -
b        W   S  Q  L   R  A  A   S  T  P   S  L  S   T  G  V   S  L   S  Q   -
c         G   A  N  S   G  Q  P   P  H  P   A  S  V   L  A  S   L  *  V   N   -

T
                t
                h
                l             M
                l             s
                l        A   pM    B        H
                l        c   An    s        iT
                I        i   l l    l        nf
                I        I   I I    I        f I
                                             I I
                                    /
       acgcttctcctcattccgctgtttggaatccactatgtcattttcaacttcctgcctgac
1141   ----------+----------+----------+----------+----------+----------+   1200
       tgcgaagaggagtaaggcgacaaaccttaggtgatacagtaaaagttgaaggacggactg a       T   L  L  L   I  P   L  F   G  I  H   Y  V  I   F  N   F  L  P   D    -
b        R   F  S  S   F  R   C  L   E  S  T   M  S  F   S  T   S  C  L   T   -
c         A   S  P  H   S  A   V  W   N  P  L   C  H  F   Q  L   P  A  *  Q   -

B
                                                        s
         T                                              p        E
         s   T   C   B                                 CB1    BBcS    C
        Fp   s   v   s         AE    C       B  M  B   B  B   Bva2   ssoc   vC
        o4   p   i   p         cc    j       f  n  s   f  s   sin8   maRr   i j
        kC   R   J   G         I I    e       a  l  I   I  r   rJI6   FJIF   Je
        I I   I   I   I         I I    I       I  I  I   I  I   I I I I   I I I I   I I
            /                                            / /              / /
       agtgctgggctggacatccgcctcccccctagaactgggactgggctctttccagggcttc
1201   ----------+----------+----------+----------+----------+----------+   1260
       tcacgacccgacctgtaggcggaggggggatcttgaccctgacccgagaaaggtcccgaag a       S   A  G  L   D  I  R   L  P   L  E  L   G  L  G   S  F  Q   G  F    -
b        V   L  G  W   T  S  A   S  P   *  N  W   D  W  A   L  S  R   A  S   -
c         C   W  A  G   H  P  P   P  P   P  R  T   G  T  G   L  F  P   G  L  H   -
```

FIG. 20G

```
                                         S
                                      BB  a
                 RT       M    M M    D gsDHu     M
                 sa       n    n n    d ltpp3     s
                 at       l    l l    e lYnhA     l
                 II       I    I I    I IIIII     I
                /                         / //
         attgttgctatcctgtactgcttcctcaaccaagaggtgaggactgagatctcacggaga
1261     ---------+---------+---------+---------+---------+---------+  1320
         taacaacgataggacatgacgaaggagttggttctccactcctgactctagagtgcctct a        I  V  A  I  L  Y  C  F  L  N  Q  E  V  R  T  E  I  S  R  R   -
b          L  L  L  S  C  T  A  S  S  T  K  R  *  G  L  R  S  H  G  D -
c            C  C  Y  P  V  L  L  P  Q  P  R  G  E  D  *  D  L  T  E  M -

H S
           CGa a              C C    S   H                H
         B EAvde u D        B aMv MNPc   i    M   D     M i ATX
         c aliir 3 p        c cni sclr   n    n   l     n n vah
         c ewJII A n        e 81J pieF   f    l   e     l f ago
         I IIIII I I        I III IIII   I    I   I     I I III
                //           /  ///                              /
         tggcacggccacgatcctgaacttctgccagcccggaggactcatatcaagtgaggactc
1321     ---------+---------+---------+---------+---------+---------+  1380
         accgtgccggtgctaggacttgaagacggtcgggcctcctgagtatagttcactcctgag a        W  H  G  H  D  P  E  L  L  P  A  R  R  T  H  I  K  *  G  L   -
b          G  T  A  T  I  L  N  F  C  Q  P  G  G  L  I  S  S  E  D  S -
c            A  R  P  R  S  *  T  S  A  S  P  E  D  S  Y  Q  V  R  T  R -

B
                                                                 s
                                                                 p
                                   C       CAC          CNB1
                       H   M       v       Vla    B  M  Bvla2
                       p   s       i       iwC    s  w  Sian8
                       h   l       J       JN8    l  o  rJII6
                       I   I       I       III    I  I  IIVII
                                                        / /
         gagggtgaaggtgctgacatctgtgtgttaggctggtcagagcctgcgactggagcccac
1381     ---------+---------+---------+---------+---------+---------+  1440
         ctcccacttccacgactgtagacacacaatccgaccagtctcggacgctgacctcgggtg a        E  G  E  G  A  D  I  C  V  L  G  W  S  E  P  A  T  G  A  H   -
b          R  V  K  V  L  T  S  V  C  *  A  G  Q  S  L  R  L  E  P  T -
c            G  *  R  C  *  H  L  C  V  R  L  V  R  A  C  D  W  S  P  H -
```

FIG. 20H

```
                          F       E                                          N
                         Rn   C  cBs                       B              B  l   NC
                      B  B  luTAv osc   SBA     B    H     M sDNSa lv
                      s  p  e4sli Rar   ibc    s     g     n  asctI al
                      l  m  AHeuJ IJF   MVC    m F   a     l  JaoyI IJ
                      I  I  IIIII III   III    I     I     I  IIIII VI
                                 //                                  ///
                         acctgaacttggcagctacctgggtctaccaccctccacagcgtcccatgggagcctca
                 1441   ---------+---------+---------+---------+---------+---------+   1500
                         tggacttgaacccgtcgatggacccagatggtgggaggtgtcgcagggtaccctcggagt
```

```
  a       T  *  T  W  A  A  T  W  V  Y  H  P  P  Q  R  P  M  G  A  S    -
  b        P  E  L  G  Q  L  P  G  S  T  T  L  H  S  V  P  W  E  P  H   -
  c          L  N  L  G  S  Y  L  G  L  P  P  S  T  A  S  H  G  S  L  M -
```

```
                     N                              A
                     l                  T           l      H
                     a        M         a          wP      i
                     l        n         q          21      n
                     I        l         I          6e      f
                     I        I                    II      I
                                                    /
                         tgcttccacccagcacttctttcctgtctcgttcctgactctttt
                 1501   ---------+---------+---------+---------+-----     1545
                         acgaaggtgggtcgtgaagaaaggacagagcaaggactgagaaaa
```

```
         ←——TM7——→  ←————C-Terminal Tail————
Ovine    FIVAILYCFLNQEVRTEISRRWHGHDPELLPARRTHIK*
Porcine  FIVAILYCFLNQEVRTEISRRWHGHDPELLPAWRTHAKWAKPSRSRAKVLTTVC*
Human    FIVAILYCFLNQEVRTEISRKWHGHDPELLPAWRTRAKWTTPSRSAAKVLTSMC*
Rat      FVVAVLYCFLNQEVRTEISRKWYGHDPELLPARRTCTEWTTPPRSRVKVLTSEC*
Mouse    FIVAVLYCFLNQEVRTEISRKWYGHDPEILPARRTCTEWTTPPRSRLKVLTSEC*
```

FIG. 21

SEQUENCE LISTING ( 1 ) GENERAL INFORMATION:

( i i i ) NUMBER OF SEQUENCES: 18

( 2 ) INFORMATION FOR SEQ ID NO:1:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:1:

GCAACAGTGG GCGGAGCATG CTCAGC                                                        2 6

( 2 ) INFORMATION FOR SEQ ID NO:2:

( i ) SEQUENCE CHARACTERISTICS:
        ( A ) LENGTH: 26 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:2:

GGCGCCTTGC TGCAGCCTCA GATGAT                                                        2 6

( 2 ) INFORMATION FOR SEQ ID NO:3:

( i ) SEQUENCE CHARACTERISTICS:
        ( A ) LENGTH: 23 base pairs
        ( B ) TYPE: nucleic acid
        ( C ) STRANDEDNESS: single
        ( D ) TOPOLOGY: linear ( i i ) MOLECULE TYPE: cDNA ( x i ) SEQUENCE DESCRIPTION: SEQ ID NO:3:

AAGGTCATGT ACACTGTAGG CTA                                                            2 3

( 2 ) INFORMATION FOR SEQ ID NO:4:

( i ) SEQUENCE CHARACTERISTICS:
        ( A ) LENGTH: 23 base pairs (B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:4:

AGCGGGAACT CTTGAAGGTG CCA     23

(2) INFORMATION FOR SEQ ID NO:5:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO:5:

CCAATACTGA GACTGGGTAT GGAGGCTGCC     30

(2) INFORMATION FOR SEQ ID NO:6:

(i) SEQUENCE CHARACTERISTICS:
(A) LENGTH: 30 base pairs
(B) TYPE: nucleic acid
(C) STRANDEDNESS: single
(D) TOPOLOGY: linear (ii) MOLECULE TYPE: DNA (genomic)

(xi) SEQUENCE DESCRIPTION: SEQ ID NO:6:

GGAAACTGGA GCCAGCTCAG GGCAGCCTCC     30

(2) INFORMATION FOR SEQ ID NO:7:

(i) SEQUENCE CHARACTERISTICS:
(A) LENGTH: 1272 base pairs
(B) TYPE: nucleic acid
(C) STRANDEDNESS: single
(D) TOPOLOGY: linear (ii) MOLECULE TYPE: cDNA (ix) FEATURE:
(A) NAME/KEY: CDS
(B) LOCATION: 1..1269

(xi) SEQUENCE DESCRIPTION: SEQ ID NO:7:

| ATG | GAC | CGC | CGG | ATG | TGG | GGG | GCC | CAC | GTC | TTC | TGC | GTG | TTG | AGC | CCG | 48 |
| Met | Asp | Arg | Arg | Met | Trp | Gly | Ala | His | Val | Phe | Cys | Val | Leu | Ser | Pro | |
| 1 | | | | 5 | | | | | 10 | | | | | 15 | | |

| TTA | CCG | ACC | GTA | TTG | GGC | CAC | ATG | CAC | CCA | GAA | TGT | GAC | TTC | ATC | ACC | 96 |
| Leu | Pro | Thr | Val | Leu | Gly | His | Met | His | Pro | Glu | Cys | Asp | Phe | Ile | Thr | |
| | | | 20 | | | | | 25 | | | | | 30 | | | |

| CAG | CTG | AGA | GAG | GAT | GAG | AGT | GCC | TGT | CTA | CAA | GCA | GCA | GAG | GAG | ATG | 144 |
| Gln | Leu | Arg | Glu | Asp | Glu | Ser | Ala | Cys | Leu | Gln | Ala | Ala | Glu | Glu | Met | |
| | | 35 | | | | | 40 | | | | | 45 | | | | |

| CCC | AAC | ACC | ACC | CTG | GGC | TGC | CCT | GCG | ACC | TGG | GAT | GGG | CTG | CTG | TGC | 192 |
| Pro | Asn | Thr | Thr | Leu | Gly | Cys | Pro | Ala | Thr | Trp | Asp | Gly | Leu | Leu | Cys | |
| | 50 | | | | | 55 | | | | | 60 | | | | | |

| TGG | CCA | ACG | GCA | GGC | TCT | GGC | GAG | TGG | GTC | ACC | CTC | CCC | TGC | CCG | GAT | 240 |
| Trp | Pro | Thr | Ala | Gly | Ser | Gly | Glu | Trp | Val | Thr | Leu | Pro | Cys | Pro | Asp | |
| 65 | | | | | 70 | | | | | 75 | | | | | 80 | |

| TTC | TTC | TCT | CAC | TTC | AGC | TCA | GAG | TCA | GGG | GCT | GTG | AAA | CGG | GAT | TGT | 288 |
| Phe | Phe | Ser | His | Phe | Ser | Ser | Glu | Ser | Gly | Ala | Val | Lys | Arg | Asp | Cys | |
| | | | | 85 | | | | | 90 | | | | | 95 | | |

| | | | | | | | | | | | | | | | | |
|---|---|---|---|---|---|---|---|---|---|---|---|---|---|---|---|---|
| ACT | ATC | ACT | GGC | TGG | TCT | GAG | CCC | TTT | CCA | CCT | TAC | CCT | GTG | GCC | TGC | 336 |
| Thr | Ile | Thr | Gly | Trp | Ser | Glu | Pro | Phe | Pro | Pro | Tyr | Pro | Val | Ala | Cys | |
| | | 100 | | | | | 105 | | | | | | 110 | | | |
| CCT | GTG | CCT | CTG | GAG | CTG | CTG | GCT | GAG | GAG | GAA | TCT | TAC | TTC | TCC | ACA | 384 |
| Pro | Val | Pro | Leu | Glu | Leu | Leu | Ala | Glu | Glu | Glu | Ser | Tyr | Phe | Ser | Thr | |
| | | 115 | | | | 120 | | | | | 125 | | | | | |
| GTG | AAG | ATT | ATC | TAC | ACC | GTG | GGC | CAT | AGC | ATC | TCT | ATT | GTA | GCC | CTC | 432 |
| Val | Lys | Ile | Ile | Tyr | Thr | Val | Gly | His | Ser | Ile | Ser | Ile | Val | Ala | Leu | |
| | 130 | | | | | 135 | | | | 140 | | | | | | |
| TTC | GTG | GCC | ATC | ACC | ATC | CTG | GTT | GCT | CTC | AGG | AGG | CTC | CAC | TGC | CCC | 480 |
| Phe | Val | Ala | Ile | Thr | Ile | Leu | Val | Ala | Leu | Arg | Arg | Leu | His | Cys | Pro | |
| 145 | | | | | 150 | | | | | 155 | | | | | 160 | |
| CGG | AAC | TAC | GTC | CAC | ACC | CAG | CTG | TTC | ACC | ACT | TTT | ATC | CTC | AAG | GCG | 528 |
| Arg | Asn | Tyr | Val | His | Thr | Gln | Leu | Phe | Thr | Thr | Phe | Ile | Leu | Lys | Ala | |
| | | | | 165 | | | | | 170 | | | | | 175 | | |
| GGA | GCT | GTG | TTC | CTG | AAG | GAT | GCT | GCC | CTT | TTC | CAC | AGC | GAC | GAC | ACT | 576 |
| Gly | Ala | Val | Phe | Leu | Lys | Asp | Ala | Ala | Leu | Phe | His | Ser | Asp | Asp | Thr | |
| | | | 180 | | | | | 185 | | | | | 190 | | | |
| GAC | CAC | TGC | AGC | TTC | TCC | ACT | GTT | CTA | TGC | AAG | GTC | TCT | GTG | GCC | GCC | 624 |
| Asp | His | Cys | Ser | Phe | Ser | Thr | Val | Leu | Cys | Lys | Val | Ser | Val | Ala | Ala | |
| | | 195 | | | | | 200 | | | | | 205 | | | | |
| TCC | CAT | TTC | GCC | ACC | ATG | ACC | AAC | TTC | AGC | TGG | CTG | TTG | GCA | GAA | GCC | 672 |
| Ser | His | Phe | Ala | Thr | Met | Thr | Asn | Phe | Ser | Trp | Leu | Leu | Ala | Glu | Ala | |
| | 210 | | | | | 215 | | | | | 220 | | | | | |
| GTC | TAC | CTG | AAC | TGC | CTC | CTG | GCC | TCC | ACC | TCC | CCC | AGC | TCA | AGG | AGA | 720 |
| Val | Tyr | Leu | Asn | Cys | Leu | Leu | Ala | Ser | Thr | Ser | Pro | Ser | Ser | Arg | Arg | |
| 225 | | | | | 230 | | | | | 235 | | | | | 240 | |
| GCC | TTC | TGG | TGG | CTG | GTT | CTC | GCT | GGC | TGG | GGG | CTG | CCC | GTG | CTC | TTC | 768 |
| Ala | Phe | Trp | Trp | Leu | Val | Leu | Ala | Gly | Trp | Gly | Leu | Pro | Val | Leu | Phe | |
| | | | | 245 | | | | | 250 | | | | | 255 | | |
| ACT | GGC | ACG | TGG | GTG | AGC | TGC | AAA | CTG | GCC | TTC | GAG | GAC | ATC | GCG | TGC | 816 |
| Thr | Gly | Thr | Trp | Val | Ser | Cys | Lys | Leu | Ala | Phe | Glu | Asp | Ile | Ala | Cys | |
| | | | 260 | | | | | 265 | | | | | 270 | | | |
| TGG | GAC | CTG | GAC | GAC | ACC | TCC | CCC | TAC | TGG | TGG | ATC | ATC | AAA | GGG | CCC | 864 |
| Trp | Asp | Leu | Asp | Asp | Thr | Ser | Pro | Tyr | Trp | Trp | Ile | Ile | Lys | Gly | Pro | |
| | | 275 | | | | | 280 | | | | | 285 | | | | |
| ATT | GTC | CTC | TCG | GTC | GGG | GTG | AAC | TTT | GGG | CTT | TTT | CTC | AAT | ATT | ATC | 912 |
| Ile | Val | Leu | Ser | Val | Gly | Val | Asn | Phe | Gly | Leu | Phe | Leu | Asn | Ile | Ile | |
| | 290 | | | | | 295 | | | | | 300 | | | | | |
| CGC | ATC | CTG | GTG | AGG | AAA | CTG | GAG | CCA | GCT | CAG | GGC | AGC | CTC | CAT | ACC | 960 |
| Arg | Ile | Leu | Val | Arg | Lys | Leu | Glu | Pro | Ala | Gln | Gly | Ser | Leu | His | Thr | |
| 305 | | | | | 310 | | | | | 315 | | | | | 320 | |
| CAG | TCT | CAG | TAT | TGG | CGT | CTC | TCC | AAG | TCG | ACA | CTT | TTC | CTG | ATC | CCA | 1008 |
| Gln | Ser | Gln | Tyr | Trp | Arg | Leu | Ser | Lys | Ser | Thr | Leu | Phe | Leu | Ile | Pro | |
| | | | | 325 | | | | | 330 | | | | | 335 | | |
| CTC | TTT | GGA | ATT | CAC | TAC | ATC | ATC | TTC | AAC | TTC | CTG | CCA | GAC | AAT | GCT | 1056 |
| Leu | Phe | Gly | Ile | His | Tyr | Ile | Ile | Phe | Asn | Phe | Leu | Pro | Asp | Asn | Ala | |
| | | | 340 | | | | | 345 | | | | | 350 | | | |
| GGC | CTG | GGC | ATC | CGC | CTC | CCC | CTG | GAG | CTG | GGA | CTG | GGT | TCC | TTC | CAG | 1104 |
| Gly | Leu | Gly | Ile | Arg | Leu | Pro | Leu | Glu | Leu | Gly | Leu | Gly | Ser | Phe | Gln | |
| | | 355 | | | | | 360 | | | | | 365 | | | | |
| GGC | TTC | ATT | GTT | GCC | ATC | CTC | TAC | TGC | TTC | CTC | AAC | CAA | GAG | GTG | AGG | 1152 |
| Gly | Phe | Ile | Val | Ala | Ile | Leu | Tyr | Cys | Phe | Leu | Asn | Gln | Glu | Val | Arg | |
| | 370 | | | | | 375 | | | | | 380 | | | | | |
| ACT | GAG | ATC | TCA | CGG | AAG | TGG | CAT | GGC | CAT | GAC | CCT | GAG | CTT | CTG | CCA | 1200 |
| Thr | Glu | Ile | Ser | Arg | Lys | Trp | His | Gly | His | Asp | Pro | Glu | Leu | Leu | Pro | |
| 385 | | | | | 390 | | | | | 395 | | | | | 400 | |
| GCC | TGG | AGG | ACC | CGT | GCT | AAG | TGG | ACC | ACG | CCT | TCC | CGC | TCG | GCG | GCA | 1248 |
| Ala | Trp | Arg | Thr | Arg | Ala | Lys | Trp | Thr | Thr | Pro | Ser | Arg | Ser | Ala | Ala | |
| | | | | 405 | | | | | 410 | | | | | 415 | | |

```
AAG  GTG  CTG  ACA  TCT  ATG  TGC  TAG                                    1272
Lys  Val  Leu  Thr  Ser  Met  Cys
               420
```

( 2 ) INFORMATION FOR SEQ ID NO:8:

( i ) SEQUENCE CHARACTERISTICS:
        ( A ) LENGTH: 423 amino acids
        ( B ) TYPE: amino acid
        ( D ) TOPOLOGY: linear ( i i ) MOLECULE TYPE: protein ( x i ) SEQUENCE DESCRIPTION: SEQ ID NO:8:

```
Met  Asp  Arg  Arg  Met  Trp  Gly  Ala  His  Val  Phe  Cys  Val  Leu  Ser  Pro
 1                   5                   10                  15

Leu  Pro  Thr  Val  Leu  Gly  His  Met  His  Pro  Glu  Cys  Asp  Phe  Ile  Thr
               20                   25                   30

Gln  Leu  Arg  Glu  Asp  Glu  Ser  Ala  Cys  Leu  Gln  Ala  Ala  Glu  Glu  Met
          35                   40                        45

Pro  Asn  Thr  Thr  Leu  Gly  Cys  Pro  Ala  Thr  Trp  Asp  Gly  Leu  Leu  Cys
     50                        55                   60

Trp  Pro  Thr  Ala  Gly  Ser  Gly  Glu  Trp  Val  Thr  Leu  Pro  Cys  Pro  Asp
65                        70                   75                        80

Phe  Phe  Ser  His  Phe  Ser  Ser  Glu  Ser  Gly  Ala  Val  Lys  Arg  Asp  Cys
                    85                        90                        95

Thr  Ile  Thr  Gly  Trp  Ser  Glu  Pro  Phe  Pro  Pro  Tyr  Pro  Val  Ala  Cys
               100                       105                      110

Pro  Val  Pro  Leu  Glu  Leu  Leu  Ala  Glu  Glu  Ser  Tyr  Phe  Ser  Thr
          115                       120                      125

Val  Lys  Ile  Ile  Tyr  Thr  Val  Gly  His  Ser  Ile  Ser  Ile  Val  Ala  Leu
     130                       135                      140

Phe  Val  Ala  Ile  Thr  Ile  Leu  Val  Ala  Leu  Arg  Arg  Leu  His  Cys  Pro
145                           150                      155                     160

Arg  Asn  Tyr  Val  His  Thr  Gln  Leu  Phe  Thr  Thr  Phe  Ile  Leu  Lys  Ala
                    165                       170                      175

Gly  Ala  Val  Phe  Leu  Lys  Asp  Ala  Ala  Leu  Phe  His  Ser  Asp  Asp  Thr
               180                       185                      190

Asp  His  Cys  Ser  Phe  Ser  Thr  Val  Leu  Cys  Lys  Val  Ser  Val  Ala  Ala
          195                       200                      205

Ser  His  Phe  Ala  Thr  Met  Thr  Asn  Phe  Ser  Trp  Leu  Ala  Glu  Ala
     210                       215                      220

Val  Tyr  Leu  Asn  Cys  Leu  Leu  Ala  Ser  Thr  Ser  Pro  Ser  Ser  Arg  Arg
225                      230                       235                      240

Ala  Phe  Trp  Trp  Leu  Val  Leu  Ala  Gly  Trp  Gly  Leu  Pro  Val  Leu  Phe
                    245                       250                      255

Thr  Gly  Thr  Trp  Val  Ser  Cys  Lys  Leu  Ala  Phe  Glu  Asp  Ile  Ala  Cys
               260                       265                      270

Trp  Asp  Leu  Asp  Asp  Thr  Ser  Pro  Tyr  Trp  Trp  Ile  Ile  Lys  Gly  Pro
          275                       280                      285

Ile  Val  Leu  Ser  Val  Gly  Val  Asn  Phe  Gly  Leu  Phe  Leu  Asn  Ile  Ile
     290                       295                      300

Arg  Ile  Leu  Val  Arg  Lys  Leu  Glu  Pro  Ala  Gln  Gly  Ser  Leu  His  Thr
305                      310                       315                      320

Gln  Ser  Gln  Tyr  Trp  Arg  Leu  Ser  Lys  Ser  Thr  Leu  Phe  Leu  Ile  Pro
                    325                       330                      335
```

-continued

| | | | | | | | | | | | | | | |
|---|---|---|---|---|---|---|---|---|---|---|---|---|---|---|
| Leu | Phe | Gly | Ile | His | Tyr | Ile | Ile | Phe | Asn | Phe | Leu | Pro | Asp | Asn | Ala |
| | | | 340 | | | | 345 | | | | | 350 | | |
| Gly | Leu | Gly | Ile | Arg | Leu | Pro | Leu | Glu | Leu | Gly | Leu | Gly | Ser | Phe | Gln |
| | | | 355 | | | | 360 | | | | 365 | | | |
| Gly | Phe | Ile | Val | Ala | Ile | Leu | Tyr | Cys | Phe | Leu | Asn | Gln | Glu | Val | Arg |
| | 370 | | | | | 375 | | | | | 380 | | | | |
| Thr | Glu | Ile | Ser | Arg | Lys | Trp | His | Gly | His | Asp | Pro | Glu | Leu | Leu | Pro |
| 385 | | | | | 390 | | | | | 395 | | | | | 400 |
| Ala | Trp | Arg | Thr | Arg | Ala | Lys | Trp | Thr | Thr | Pro | Ser | Arg | Ser | Ala | Ala |
| | | | | 405 | | | | | 410 | | | | | 415 | |
| Lys | Val | Leu | Thr | Ser | Met | Cys | | | | | | | | | |
| | | | 420 | | | | | | | | | | | | |

(2) INFORMATION FOR SEQ ID NO:9:

(i) SEQUENCE CHARACTERISTICS:
        (A) LENGTH: 1545 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: CDS
        (B) LOCATION: 1..1371

(xi) SEQUENCE DESCRIPTION: SEQ ID NO:9:

| | | | | | | | | | | | | | | | | |
|---|---|---|---|---|---|---|---|---|---|---|---|---|---|---|---|---|
| CGG | CAC | GAG | TCT | CTC | TCT | CTC | TCT | CTC | TCT | CTC | TCT | CTC | CTC | | | 48 |
| Arg | His | Glu | Ser | Leu | Ser | Leu | Ser | Leu | Ser | Leu | Ser | Leu | Leu | | | |
| | 425 | | | | 430 | | | | | 435 | | | | | | |
| GTG | CCG | AAT | TCG | GCA | CGA | GCT | GGC | AGC | AGT | GAC | AAC | AGG | GGA | CGG | TGG | 96 |
| Val | Pro | Asn | Ser | Ala | Arg | Ala | Gly | Ser | Ser | Asp | Asn | Arg | Gly | Arg | Trp | |
| 440 | | | | | 445 | | | | | 450 | | | | | 455 | |
| AAG | GAG | CAC | AGG | GCC | ACC | GAG | GCT | GAC | CCA | GGC | AGC | CGT | CGC | CGA | GCT | 144 |
| Lys | Glu | His | Arg | Ala | Thr | Glu | Ala | Asp | Pro | Gly | Ser | Arg | Arg | Arg | Ala | |
| | | | | 460 | | | | | 465 | | | | | 470 | | |
| CCC | ACC | ATG | GGC | AGC | AGG | GTG | TGG | GGC | GCC | TGC | GTC | CTC | TGC | TTG | CTG | 192 |
| Pro | Thr | Met | Gly | Ser | Arg | Val | Trp | Gly | Ala | Cys | Val | Leu | Cys | Leu | Leu | |
| | | | 475 | | | | | 480 | | | | | 485 | | | |
| GGC | CCC | TTG | CCA | ATC | GTC | CTG | GGC | CAC | GTG | CAC | CCA | GAG | TGT | GAT | GTC | 240 |
| Gly | Pro | Leu | Pro | Ile | Val | Leu | Gly | His | Val | His | Pro | Glu | Cys | Asp | Val | |
| | | 490 | | | | | 495 | | | | | 500 | | | | |
| ATC | ACT | CAG | CTG | AGA | GAG | GAC | GAG | CAA | GCA | TGT | CTA | CAA | GCT | GCT | GAA | 288 |
| Ile | Thr | Gln | Leu | Arg | Glu | Asp | Glu | Gln | Ala | Cys | Leu | Gln | Ala | Ala | Glu | |
| | 505 | | | | | 510 | | | | | 515 | | | | | |
| GGG | ATG | CCC | AAC | TCC | ACC | TTG | GGC | TGC | CCC | AGG | ATC | TGG | GAC | GGG | CTG | 336 |
| Gly | Met | Pro | Asn | Ser | Thr | Leu | Gly | Cys | Pro | Arg | Ile | Trp | Asp | Gly | Leu | |
| 520 | | | | | 525 | | | | | 530 | | | | | 535 | |
| CTG | TGC | TGG | CCG | ATG | GCA | GGC | TCT | GGA | GAG | TGG | GTG | AGC | CTC | CCC | TGC | 384 |
| Leu | Cys | Trp | Pro | Met | Ala | Gly | Ser | Gly | Glu | Trp | Val | Ser | Leu | Pro | Cys | |
| | | | | 540 | | | | | 545 | | | | | 550 | | |
| CCG | GCT | TTC | TTC | TCT | CAC | TTC | AGC | TTG | GAG | CCA | GGG | GCT | GTG | AAG | AGG | 432 |
| Pro | Ala | Phe | Phe | Ser | His | Phe | Ser | Leu | Glu | Pro | Gly | Ala | Val | Lys | Arg | |
| | | | 555 | | | | 560 | | | | | 565 | | | | |
| GAC | TGC | ACC | ATT | GCA | GGC | TGG | TCG | GAG | CCC | TTC | CCG | CCT | TAT | CCC | GAG | 480 |
| Asp | Cys | Thr | Ile | Ala | Gly | Trp | Ser | Glu | Pro | Phe | Pro | Pro | Tyr | Pro | Glu | |
| | | 570 | | | | | 575 | | | | | 580 | | | | |
| GCC | TGC | CCT | GTG | CCC | CTG | GAG | CTG | CTG | ACT | GAG | GAG | AAA | TCC | TAC | TTC | 528 |
| Ala | Cys | Pro | Val | Pro | Leu | Glu | Leu | Leu | Thr | Glu | Glu | Lys | Ser | Tyr | Phe | |
| | 585 | | | | | 590 | | | | | 595 | | | | | |
| TCC | GCG | GTA | AGG | ATC | GTC | TAC | ACC | ATG | GGC | CAC | AGC | GTC | TCG | GCT | GCA | 576 |

-continued

| | | | | | | | | | | | | | | | |
|---|---|---|---|---|---|---|---|---|---|---|---|---|---|---|---|
| Ser | Ala | Val | Arg | Ile | Val | Tyr | Thr | Met | Gly | His | Ser | Val | Ser | Ala | Ala |
| 600 | | | | | 605 | | | | 610 | | | | | | 615 |

| GCC | CTC | CTA | GTG | GCC | ATC | ATC | ATC | CTG | GTC | GCT | CTC | AGG | AGG | CTC | CAC | 624 |
|---|---|---|---|---|---|---|---|---|---|---|---|---|---|---|---|---|
| Ala | Leu | Leu | Val | Ala | Ile | Ile | Ile | Leu | Val | Ala | Leu | Arg | Arg | Leu | His | |
| | | | | 620 | | | | | 625 | | | | | 630 | | |

| TGC | CCC | AGG | AAC | TAC | ATC | CAC | ACC | CAG | CTG | TTC | ACC | ACC | TTT | ATC | CTC | 672 |
|---|---|---|---|---|---|---|---|---|---|---|---|---|---|---|---|---|
| Cys | Pro | Arg | Asn | Tyr | Ile | His | Thr | Gln | Leu | Phe | Thr | Thr | Phe | Ile | Leu | |
| | | | 635 | | | | | 640 | | | | | 645 | | | |

| AAG | GCG | GCA | GCT | GTG | TTC | CTG | AAG | GAC | GCC | ACC | CTC | TTT | CAC | CGG | GAG | 720 |
|---|---|---|---|---|---|---|---|---|---|---|---|---|---|---|---|---|
| Lys | Ala | Ala | Ala | Val | Phe | Leu | Lys | Asp | Ala | Thr | Leu | Phe | His | Arg | Glu | |
| | | 650 | | | | | 655 | | | | | 660 | | | | |

| AAC | ATG | GAC | CAC | TGC | AGC | TTC | TCC | ACT | GTC | CTG | TGC | AAG | GCT | TCT | GTG | 768 |
|---|---|---|---|---|---|---|---|---|---|---|---|---|---|---|---|---|
| Asn | Met | Asp | His | Cys | Ser | Phe | Ser | Thr | Val | Leu | Cys | Lys | Ala | Ser | Val | |
| | 665 | | | | | 670 | | | | | 675 | | | | | |

| ACC | GCC | TCT | CAT | TTC | GCG | ACC | ATG | ACC | AAC | TTC | AGC | TGG | CTG | CTG | GCA | 816 |
|---|---|---|---|---|---|---|---|---|---|---|---|---|---|---|---|---|
| Thr | Ala | Ser | His | Phe | Ala | Thr | Met | Thr | Asn | Phe | Ser | Trp | Leu | Leu | Ala | |
| 680 | | | | | 685 | | | | | 690 | | | | | 695 | |

| GAA | GCT | GTG | TAC | CTG | ACC | TGC | CTC | TTA | GCC | TCC | ACA | TTG | CCC | AGC | ACA | 864 |
|---|---|---|---|---|---|---|---|---|---|---|---|---|---|---|---|---|
| Glu | Ala | Val | Tyr | Leu | Thr | Cys | Leu | Leu | Ala | Ser | Thr | Leu | Pro | Ser | Thr | |
| | | | | 700 | | | | | 705 | | | | | 710 | | |

| AGG | AGG | GTC | TTC | TGG | TGG | CTG | GTT | CTC | GCT | GCC | TGG | GGG | CTT | CCT | CTG | 912 |
|---|---|---|---|---|---|---|---|---|---|---|---|---|---|---|---|---|
| Arg | Arg | Val | Phe | Trp | Trp | Leu | Val | Leu | Ala | Ala | Trp | Gly | Leu | Pro | Leu | |
| | | | 715 | | | | | 720 | | | | | 725 | | | |

| CTC | TTC | ACC | AGC | ATG | TGG | GTG | GGT | TGC | AAG | TTG | GCC | TTT | GAA | GAT | GTT | 960 |
|---|---|---|---|---|---|---|---|---|---|---|---|---|---|---|---|---|
| Leu | Phe | Thr | Ser | Met | Trp | Val | Gly | Cys | Lys | Leu | Ala | Phe | Glu | Asp | Val | |
| | | 730 | | | | | 735 | | | | | 740 | | | | |

| GCG | TGC | TGG | GAC | CTG | GAC | GAC | AGC | TCC | CCC | TAC | TGG | TGG | ATC | ATC | AAA | 1008 |
|---|---|---|---|---|---|---|---|---|---|---|---|---|---|---|---|---|
| Ala | Cys | Trp | Asp | Leu | Asp | Asp | Ser | Ser | Pro | Tyr | Trp | Trp | Ile | Ile | Lys | |
| | 745 | | | | | 750 | | | | | 755 | | | | | |

| GGA | CCC | ATC | GTC | CTC | TCT | GTT | GGG | GTG | AAC | TTT | GGG | CTT | TTT | CTC | AAT | 1056 |
|---|---|---|---|---|---|---|---|---|---|---|---|---|---|---|---|---|
| Gly | Pro | Ile | Val | Leu | Ser | Val | Gly | Val | Asn | Phe | Gly | Leu | Phe | Leu | Asn | |
| 760 | | | | | 765 | | | | | 770 | | | | | 775 | |

| ATT | ATC | CGT | ATC | CTG | CTG | AGG | AAA | CTG | GAG | CCA | ACT | CAG | GGC | AGC | CTC | 1104 |
|---|---|---|---|---|---|---|---|---|---|---|---|---|---|---|---|---|
| Ile | Ile | Arg | Ile | Leu | Leu | Arg | Lys | Leu | Glu | Pro | Thr | Gln | Gly | Ser | Leu | |
| | | | | 780 | | | | | 785 | | | | | 790 | | |

| CAC | ACC | CAG | CCT | CAG | TAC | TGG | CGT | CTC | TCT | AAG | TCA | ACG | CTT | CTC | CTC | 1152 |
|---|---|---|---|---|---|---|---|---|---|---|---|---|---|---|---|---|
| His | Thr | Gln | Pro | Gln | Tyr | Trp | Arg | Leu | Ser | Lys | Ser | Thr | Leu | Leu | Leu | |
| | | | 795 | | | | | 800 | | | | | 805 | | | |

| ATT | CCG | CTG | TTT | GGA | ATC | CAC | TAT | GTC | ATT | TTC | AAC | TTC | CTG | CCT | GAC | 1200 |
|---|---|---|---|---|---|---|---|---|---|---|---|---|---|---|---|---|
| Ile | Pro | Leu | Phe | Gly | Ile | His | Tyr | Val | Ile | Phe | Asn | Phe | Leu | Pro | Asp | |
| | | 810 | | | | | 815 | | | | | 820 | | | | |

| AGT | GCT | GGG | CTG | GAC | ATC | CGC | CTC | CCC | CTA | GAA | CTG | GGA | CTG | GGC | TCT | 1248 |
|---|---|---|---|---|---|---|---|---|---|---|---|---|---|---|---|---|
| Ser | Ala | Gly | Leu | Asp | Ile | Arg | Leu | Pro | Leu | Glu | Leu | Gly | Leu | Gly | Ser | |
| | 825 | | | | | 830 | | | | | 835 | | | | | |

| TTC | CAG | GGC | TTC | ATT | GTT | GCT | ATC | CTG | TAC | TGC | TTC | CTC | AAC | CAA | GAG | 1296 |
|---|---|---|---|---|---|---|---|---|---|---|---|---|---|---|---|---|
| Phe | Gln | Gly | Phe | Ile | Val | Ala | Ile | Leu | Tyr | Cys | Phe | Leu | Asn | Gln | Glu | |
| 840 | | | | | 845 | | | | | 850 | | | | | 855 | |

| GTG | AGG | ACT | GAG | ATC | TCA | CGG | AGA | TGG | CAC | GGC | CAC | GAT | CCT | GAA | CTT | 1344 |
|---|---|---|---|---|---|---|---|---|---|---|---|---|---|---|---|---|
| Val | Arg | Thr | Glu | Ile | Ser | Arg | Arg | Trp | His | Gly | His | Asp | Pro | Glu | Leu | |
| | | | | 860 | | | | | 865 | | | | | 870 | | |

| CTG | CCA | GCC | CGG | AGG | ACT | CAT | ATC | AAG | TGAGGACTCG | AGGGTGAAGG | 1391 |
|---|---|---|---|---|---|---|---|---|---|---|---|
| Leu | Pro | Ala | Arg | Arg | Thr | His | Ile | Lys | | | |
| | | | 875 | | | | | 880 | | | |

TGCTGACATC TGTGTGTTAG CTGGTCAGA GCCTGCGACT GGAGCCCACA CCTGAACTTG    1451

GGCAGCTACC TGGGTCTACC ACCCTCCACA GCGTCCCATG GGAGCCTCAT GCTTCCACCC    1511

AGCACTTCTT TCCTGTCTCG TTCCTGACTC TTTT    1545

( 2 ) INFORMATION FOR SEQ ID NO:10:

(i) SEQUENCE CHARACTERISTICS:
(A) LENGTH: 457 amino acids
(B) TYPE: amino acid
(D) TOPOLOGY: linear (ii) MOLECULE TYPE: protein (xi) SEQUENCE DESCRIPTION: SEQ ID NO:10:

```
Arg His Glu Ser Leu Ser Leu Ser Leu Ser Leu Ser Leu Ser Leu Leu
 1               5                  10                  15

Val Pro Asn Ser Ala Arg Ala Gly Ser Ser Asp Asn Arg Gly Arg Trp
            20                  25                  30

Lys Glu His Arg Ala Thr Glu Ala Asp Pro Gly Ser Arg Arg Ala
            35                  40                  45

Pro Thr Met Gly Ser Arg Val Trp Gly Ala Cys Val Leu Cys Leu Leu
     50                  55                  60

Gly Pro Leu Pro Ile Val Leu Gly His Val His Pro Glu Cys Asp Val
 65                  70                  75                  80

Ile Thr Gln Leu Arg Glu Asp Glu Gln Ala Cys Leu Gln Ala Ala Glu
                 85                  90                  95

Gly Met Pro Asn Ser Thr Leu Gly Cys Pro Arg Ile Trp Asp Gly Leu
                100                 105                 110

Leu Cys Trp Pro Met Ala Gly Ser Gly Glu Trp Val Ser Leu Pro Cys
            115                 120                 125

Pro Ala Phe Phe Ser His Phe Ser Leu Glu Pro Gly Ala Val Lys Arg
    130                 135                 140

Asp Cys Thr Ile Ala Gly Trp Ser Glu Pro Phe Pro Pro Tyr Pro Glu
145                 150                 155                 160

Ala Cys Pro Val Pro Leu Glu Leu Leu Thr Glu Glu Lys Ser Tyr Phe
                165                 170                 175

Ser Ala Val Arg Ile Val Tyr Thr Met Gly His Ser Val Ser Ala Ala
            180                 185                 190

Ala Leu Leu Val Ala Ile Ile Ile Leu Val Ala Leu Arg Arg Leu His
        195                 200                 205

Cys Pro Arg Asn Tyr Ile His Thr Gln Leu Phe Thr Thr Phe Ile Leu
    210                 215                 220

Lys Ala Ala Ala Val Phe Leu Lys Asp Ala Thr Leu Phe His Arg Glu
225                 230                 235                 240

Asn Met Asp His Cys Ser Phe Ser Thr Val Leu Cys Lys Ala Ser Val
                245                 250                 255

Thr Ala Ser His Phe Ala Thr Met Thr Asn Phe Ser Trp Leu Leu Ala
            260                 265                 270

Glu Ala Val Tyr Leu Thr Cys Leu Leu Ala Ser Thr Leu Pro Ser Thr
        275                 280                 285

Arg Arg Val Phe Trp Trp Leu Val Leu Ala Ala Trp Gly Leu Pro Leu
    290                 295                 300

Leu Phe Thr Ser Met Trp Val Gly Cys Lys Leu Ala Phe Glu Asp Val
305                 310                 315                 320

Ala Cys Trp Asp Leu Asp Asp Ser Ser Pro Tyr Trp Trp Ile Ile Lys
                325                 330                 335

Gly Pro Ile Val Leu Ser Val Gly Val Asn Phe Gly Leu Phe Leu Asn
            340                 345                 350

Ile Ile Arg Ile Leu Leu Arg Lys Leu Glu Pro Thr Gln Gly Ser Leu
        355                 360                 365

His Thr Gln Pro Gln Tyr Trp Arg Leu Ser Lys Ser Thr Leu Leu Leu
    370                 375                 380
```

```
Ile  Pro  Leu  Phe  Gly  Ile  His  Tyr  Val  Ile  Phe  Asn  Phe  Leu  Pro  Asp
385                 390                 395                 400

Ser  Ala  Gly  Leu  Asp  Ile  Arg  Leu  Pro  Leu  Glu  Leu  Gly  Leu  Gly  Ser
                405                 410                 415

Phe  Gln  Gly  Phe  Ile  Val  Ala  Ile  Leu  Tyr  Cys  Phe  Leu  Asn  Gln  Glu
           420                 425                 430

Val  Arg  Thr  Glu  Ile  Ser  Arg  Arg  Trp  His  Gly  His  Asp  Pro  Glu  Leu
          435                 440                 445

Leu  Pro  Ala  Arg  Arg  Thr  His  Ile  Lys
450                      455
```

( 2 ) INFORMATION FOR SEQ ID NO:11:

( i ) SEQUENCE CHARACTERISTICS:
        ( A ) LENGTH: 513 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:11:

```
Arg  His  Glu  Ser  Leu  Ser  Leu  Ser  Leu  Ser  Leu  Ser  Leu  Ser  Leu  Leu
1                 5                   10                  15

Val  Pro  Asn  Ser  Ala  Arg  Ala  Gly  Ser  Ser  Asp  Asn  Arg  Gly  Arg  Trp
               20                  25                  30

Lys  Glu  His  Arg  Ala  Thr  Glu  Ala  Asp  Pro  Gly  Ser  Arg  Arg  Arg  Ala
          35                  40                  45

Pro  Thr  Met  Gly  Ser  Arg  Val  Trp  Gly  Ala  Cys  Val  Leu  Cys  Leu  Leu
     50                  55                  60

Gly  Pro  Leu  Pro  Ile  Val  Leu  Gly  His  Val  His  Pro  Glu  Cys  Asp  Val
65                  70                  75                       80

Ile  Thr  Gln  Leu  Arg  Glu  Asp  Glu  Gln  Ala  Cys  Leu  Gln  Ala  Ala  Glu
                85                  90                       95

Gly  Met  Pro  Asn  Ser  Thr  Leu  Gly  Cys  Pro  Arg  Ile  Trp  Asp  Gly  Leu
               100                 105                 110

Leu  Cys  Trp  Pro  Met  Ala  Gly  Ser  Gly  Glu  Trp  Val  Ser  Leu  Pro  Cys
          115                 120                 125

Pro  Ala  Phe  Phe  Ser  His  Phe  Ser  Leu  Glu  Pro  Gly  Ala  Val  Lys  Arg
     130                 135                 140

Asp  Cys  Thr  Ile  Ala  Gly  Trp  Ser  Glu  Pro  Phe  Pro  Pro  Tyr  Pro  Glu
145                 150                 155                      160

Ala  Cys  Pro  Val  Pro  Leu  Glu  Leu  Leu  Thr  Glu  Glu  Lys  Ser  Tyr  Phe
                165                 170                 175

Ser  Ala  Val  Arg  Ile  Val  Tyr  Thr  Met  Gly  His  Ser  Val  Ser  Ala  Ala
          180                 185                 190

Ala  Leu  Leu  Val  Ala  Ile  Ile  Ile  Leu  Val  Ala  Leu  Arg  Arg  Leu  His
     195                 200                 205

Cys  Pro  Arg  Asn  Tyr  Ile  His  Thr  Gln  Leu  Phe  Thr  Thr  Phe  Ile  Leu
     210                 215                 220

Lys  Ala  Ala  Ala  Val  Phe  Leu  Lys  Asp  Ala  Thr  Leu  Phe  His  Arg  Glu
225                 230                 235                      240

Asn  Met  Asp  His  Cys  Ser  Phe  Ser  Thr  Val  Leu  Cys  Lys  Ala  Ser  Val
               245                 250                 255

Thr  Ala  Ser  His  Phe  Ala  Thr  Met  Thr  Asn  Phe  Ser  Trp  Leu  Leu  Ala
               260                 265                 270
```

| | | | | | | | | | | | | | | |
|---|---|---|---|---|---|---|---|---|---|---|---|---|---|---|
| Glu | Ala | Val 275 | Tyr | Leu | Thr | Cys | Leu 280 | Leu | Ala | Ser | Thr | Leu 285 | Pro | Ser | Thr |
| Arg | Arg 290 | Val | Phe | Trp | Trp | Leu 295 | Val | Leu | Ala | Ala | Trp 300 | Gly | Leu | Pro | Leu |
| Leu 305 | Phe | Thr | Ser | Met | Trp 310 | Val | Gly | Cys | Lys | Leu 315 | Ala | Phe | Glu | Asp | Val 320 |
| Ala | Cys | Trp | Asp | Leu 325 | Asp | Asp | Ser | Ser | Pro 330 | Tyr | Trp | Trp | Ile | Ile 335 | Lys |
| Gly | Pro | Ile | Val 340 | Leu | Ser | Val | Gly | Val 345 | Asn | Phe | Gly | Leu | Phe 350 | Leu | Asn |
| Ile | Ile | Arg 355 | Ile | Leu | Leu | Arg | Lys 360 | Leu | Glu | Pro | Thr | Gln 365 | Gly | Ser | Leu |
| His | Thr 370 | Gln | Pro | Gln | Tyr | Trp 375 | Arg | Leu | Ser | Lys | Ser 380 | Thr | Leu | Leu | Leu |
| Ile 385 | Pro | Leu | Phe | Gly | Ile 390 | His | Tyr | Val | Ile | Phe 395 | Asn | Phe | Leu | Pro | Asp 400 |
| Ser | Ala | Gly | Leu | Asp 405 | Ile | Arg | Leu | Pro | Leu 410 | Glu | Leu | Gly | Leu | Gly 415 | Ser |
| Phe | Gln | Gly | Phe 420 | Ile | Val | Ala | Ile | Leu 425 | Tyr | Cys | Phe | Leu | Asn 430 | Gln | Glu |
| Val | Arg | Thr 435 | Glu | Ile | Ser | Arg | Arg 440 | Trp | His | Gly | His | Asp 445 | Pro | Glu | Leu |
| Leu | Pro 450 | Ala | Arg | Arg | Thr | His 455 | Ile | Lys | Gly | Leu | Glu 460 | Gly | Glu | Gly | Ala |
| Asp 465 | Ile | Cys | Val | Leu | Gly 470 | Trp | Ser | Glu | Pro | Ala 475 | Thr | Gly | Ala | His | Thr 480 |
| Thr | Trp | Ala | Ala | Thr 485 | Trp | Val | Tyr | His | Pro 490 | Pro | Gln | Arg | Pro | Met 495 | Gly |
| Ala | Ser | Cys | Phe 500 | His | Pro | Ala | Leu | Leu 505 | Ser | Cys | Leu | Val | Pro 510 | Asp | Ser |
| Phe | | | | | | | | | | | | | | | |

( 2 ) INFORMATION FOR SEQ ID NO:12:

( i ) SEQUENCE CHARACTERISTICS:
        ( A ) LENGTH: 498 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:12:

| | | | | | | | | | | | | | | |
|---|---|---|---|---|---|---|---|---|---|---|---|---|---|---|
| Gly 1 | Thr | Ser | Leu | Ser 5 | Leu | Ser | Leu | Ser | Leu 10 | Ser | Leu | Ser | Leu | Ser 15 | Ser |
| Cys | Arg | Ile | Arg 20 | His | Glu | Leu | Ala | Ala 25 | Val | Thr | Thr | Gly | Asp 30 | Gly | Gly |
| Arg | Ser | Thr 35 | Gly | Pro | Pro | Arg | Leu 40 | Thr | Gln | Ala | Ala | Val 45 | Ala | Glu | Leu |
| Pro | Pro 50 | Trp | Ala | Ala | Gly | Cys 55 | Gly | Ala | Pro | Ala | Ser 60 | Ala | Cys | Trp |
| Ala 65 | Pro | Cys | Gln | Ser | Ser 70 | Trp | Ala | Thr | Cys | Thr 75 | Gln | Ser | Val | Met | Ser 80 |
| Ser | Leu | Ser | Glu | Arg 85 | Thr | Ser | Lys | His | Val 90 | Tyr | Lys | Leu | Leu | Lys 95 | Gly |
| Cys | Pro | Thr | Pro 100 | Pro | Trp | Ala | Ala | Pro 105 | Gly | Ser | Gly | Thr | Gly 110 | Cys | Cys |

-continued

```
Ala  Gly  Arg  Trp  Gln  Ala  Leu  Glu  Ser  Gly  Ala  Ser  Pro  Ala  Arg  Leu
          115                 120                 125
Ser  Ser  Leu  Thr  Ser  Ala  Trp  Ser  Gln  Gly  Leu  Arg  Gly  Thr  Ala  Pro
     130                 135                 140
Leu  Gln  Ala  Gly  Arg  Ser  Pro  Ser  Arg  Leu  Ile  Pro  Arg  Pro  Ala  Leu
145                      150                 155                           160
Cys  Pro  Trp  Ser  Cys  Leu  Arg  Arg  Asn  Pro  Thr  Ser  Pro  Arg  Gly  Ser
               165                      170                           175
Ser  Thr  Pro  Trp  Ala  Thr  Ala  Ser  Arg  Leu  Gln  Pro  Ser  Trp  Pro  Ser
               180                 185                      190
Ser  Ser  Trp  Ser  Leu  Ser  Gly  Gly  Ser  Thr  Ala  Pro  Gly  Thr  Thr  Ser
          195                 200                 205
Thr  Pro  Ser  Cys  Ser  Pro  Pro  Leu  Ser  Ser  Arg  Arg  Gln  Leu  Cys  Ser
     210                 215                 220
Arg  Thr  Pro  Pro  Ser  Phe  Thr  Gly  Arg  Thr  Trp  Thr  Thr  Ala  Ala  Ser
225                      230                 235                           240
Pro  Leu  Ser  Cys  Ala  Arg  Leu  Leu  Pro  Pro  Leu  Ile  Ser  Arg  Pro  Pro
               245                      250                           255
Thr  Ser  Ala  Gly  Cys  Trp  Gln  Lys  Leu  Cys  Thr  Pro  Ala  Ser  Pro  Pro
               260                 265                      270
His  Cys  Pro  Ala  Gln  Gly  Gly  Ser  Gly  Gly  Trp  Phe  Ser  Leu  Pro
          275                 280                 285
Gly  Gly  Phe  Leu  Cys  Ser  Ser  Pro  Ala  Cys  Gly  Trp  Val  Ala  Ser  Trp
          290                 295                 300
Pro  Leu  Lys  Met  Leu  Arg  Ala  Gly  Thr  Trp  Thr  Thr  Ala  Pro  Pro  Thr
305                      310                 315                           320
Gly  Gly  Ser  Ser  Lys  Asp  Pro  Ser  Ser  Ser  Leu  Leu  Gly  Thr  Leu  Gly
               325                      330                           335
Phe  Phe  Ser  Ile  Leu  Ser  Val  Ser  Cys  Gly  Asn  Trp  Ser  Gln  Leu  Arg
               340                 345                      350
Ala  Ala  Ser  Thr  Pro  Ser  Leu  Ser  Thr  Gly  Val  Ser  Leu  Ser  Gln  Arg
               355                 360                      365
Phe  Ser  Ser  Phe  Arg  Cys  Leu  Glu  Ser  Thr  Met  Ser  Phe  Ser  Thr  Ser
     370                 375                 380
Cys  Leu  Thr  Val  Leu  Gly  Trp  Thr  Ser  Ala  Ser  Pro  Asn  Trp  Asp  Trp
385                      390                 395                           400
Ala  Leu  Ser  Arg  Ala  Ser  Leu  Leu  Leu  Ser  Cys  Thr  Ala  Ser  Ser  Thr
               405                      410                           415
Lys  Arg  Gly  Leu  Arg  Ser  His  Gly  Asp  Gly  Thr  Ala  Thr  Ile  Leu  Asn
               420                 425                      430
Phe  Cys  Gln  Pro  Gly  Gly  Leu  Ile  Ser  Ser  Glu  Asp  Ser  Arg  Val  Lys
          435                 440                 445
Val  Leu  Thr  Ser  Val  Cys  Ala  Gly  Gln  Ser  Leu  Arg  Leu  Glu  Pro  Thr
     450                 455                 460
Pro  Glu  Leu  Gly  Gln  Leu  Pro  Gly  Ser  Thr  Thr  Leu  His  Ser  Val  Pro
465                      470                 475                           480
Trp  Glu  Pro  His  Ala  Ser  Thr  Gln  His  Phe  Phe  Pro  Val  Ser  Phe  Leu
               485                 490                      495
Thr  Leu
```

( 2 ) INFORMATION FOR SEQ ID NO:13:

( i ) SEQUENCE CHARACTERISTICS:
        ( A ) LENGTH: 501 amino acids (B) TYPE: amino acid
(C) STRANDEDNESS:
(D) TOPOLOGY: linear (ii) MOLECULE TYPE: protein (xi) SEQUENCE DESCRIPTION: SEQ ID NO:13:

| | | | | | | | | | | | | | | |
|---|---|---|---|---|---|---|---|---|---|---|---|---|---|---|
| Ala | Arg | Val | Ser | Leu | Ser | Leu | Ser | Leu | Ser | Leu | Ser | Leu | Ser | Pro | Arg |
| 1 | | | | 5 | | | | | 10 | | | | | 15 |
| Ala | Glu | Phe | Gly | Thr | Ser | Trp | Gln | Gln | Gln | Gln | Gly | Thr | Val | Glu | Gly |
| | | | 20 | | | | | 25 | | | | | 30 | | |
| Ala | Gln | Gly | His | Arg | Gly | Pro | Arg | Gln | Pro | Ser | Pro | Ser | Ser | His | His |
| | | | 35 | | | | 40 | | | | | 45 | | | |
| Gly | Gln | Gln | Gly | Val | Gly | Arg | Leu | Arg | Pro | Leu | Leu | Ala | Gly | Pro | Leu |
| | 50 | | | | | 55 | | | | | 60 | | | | |
| Ala | Asn | Arg | Pro | Gly | Pro | Arg | Ala | Pro | Arg | Val | Cys | His | His | Ser | Ala |
| 65 | | | | | 70 | | | | 75 | | | | | | 80 |
| Glu | Arg | Gly | Arg | Ala | Ser | Met | Ser | Thr | Ser | Cys | Arg | Asp | Ala | Gln | Leu |
| | | | | 85 | | | | | 90 | | | | | 95 | |
| His | Leu | Gly | Leu | Pro | Gln | Asp | Leu | Gly | Arg | Ala | Ala | Val | Leu | Ala | Asp |
| | | | 100 | | | | | 105 | | | | | 110 | | |
| Gly | Arg | Leu | Trp | Arg | Val | Gly | Glu | Pro | Pro | Leu | Pro | Gly | Phe | Leu | Leu |
| | | 115 | | | | | 120 | | | | | 125 | | | |
| Ser | Leu | Gln | Leu | Gly | Ala | Arg | Gly | Cys | Glu | Glu | Gly | Leu | His | His | Cys |
| | 130 | | | | | 135 | | | | | 140 | | | | |
| Arg | Leu | Val | Gly | Ala | Leu | Pro | Ala | Leu | Ser | Arg | Gly | Leu | Pro | Cys | Ala |
| 145 | | | | | 150 | | | | | 155 | | | | | 160 |
| Pro | Gly | Ala | Ala | Asp | Gly | Glu | Ile | Leu | Leu | Leu | Arg | Gly | Lys | Asp | Arg |
| | | | | 165 | | | | | 170 | | | | | 175 | |
| Leu | His | His | Gly | Pro | Gln | Arg | Leu | Gly | Cys | Ser | Pro | Pro | Ser | Gly | His |
| | | | 180 | | | | | 185 | | | | | 190 | | |
| His | His | Pro | Gly | Arg | Ser | Gln | Glu | Ala | Pro | Leu | Pro | Gln | Glu | Leu | His |
| | | 195 | | | | | 200 | | | | | 205 | | | |
| Pro | His | Pro | Ala | Val | His | His | Leu | Tyr | Pro | Gln | Gly | Gly | Ser | Cys | Val |
| | 210 | | | | | 215 | | | | | 220 | | | | |
| Pro | Glu | Gly | Arg | His | Pro | Leu | Ser | Pro | Gly | Glu | His | Gly | Pro | Leu | Gln |
| 225 | | | | | 230 | | | | | 235 | | | | | 240 |
| Leu | Leu | His | Cys | Pro | Val | Gln | Gly | Phe | Cys | Asp | Arg | Leu | Ser | Phe | Arg |
| | | | | 245 | | | | | 250 | | | | | 255 | |
| Asp | His | Asp | Gln | Leu | Gln | Leu | Ala | Ala | Gly | Arg | Ser | Cys | Val | Pro | Asp |
| | | | 260 | | | | | 265 | | | | | 270 | | |
| Leu | Pro | Leu | Ser | Leu | His | Ile | Ala | Gln | His | Lys | Glu | Gly | Leu | Leu | Val |
| | | 275 | | | | | 280 | | | | | 285 | | | |
| Ala | Gly | Ser | Arg | Cys | Leu | Gly | Ala | Ser | Ser | Ala | Leu | His | Gln | His | Val |
| | 290 | | | | | 295 | | | | | 300 | | | | |
| Gly | Gly | Leu | Gln | Val | Gly | Leu | Arg | Cys | Cys | Val | Leu | Gly | Pro | Gly | Arg |
| 305 | | | | | 310 | | | | | 315 | | | | | 320 |
| Gln | Leu | Pro | Leu | Leu | Val | Asp | His | Gln | Arg | Thr | His | Arg | Pro | Leu | Cys |
| | | | | 325 | | | | | 330 | | | | | 335 | |
| Trp | Gly | Glu | Leu | Trp | Ala | Phe | Ser | Gln | Tyr | Tyr | Pro | Tyr | Pro | Ala | Glu |
| | | | 340 | | | | | 345 | | | | | 350 | | |
| Glu | Thr | Gly | Ala | Asn | Ser | Gly | Gln | Pro | Pro | His | Pro | Ala | Ser | Val | Leu |
| | | 355 | | | | | 360 | | | | | 365 | | | |
| Ala | Ser | Leu | Val | Asn | Ala | Ser | Pro | His | Ser | Ala | Val | Trp | Asn | Pro | Leu |
| | 370 | | | | | 375 | | | | | 380 | | | | |

```
Cys  His  Phe  Gln  Leu  Pro  Ala  Gln  Cys  Trp  Ala  Gly  His  Pro  Pro  Pro
385                      390                      395                      400

Pro  Arg  Thr  Gly  Thr  Gly  Leu  Phe  Pro  Gly  Leu  His  Cys  Cys  Tyr  Pro
                    405                      410                      415

Val  Leu  Leu  Pro  Gln  Pro  Arg  Gly  Glu  Asp  Asp  Leu  Thr  Glu  Met  Ala
               420                      425                      430

Arg  Pro  Arg  Ser  Thr  Ser  Ala  Ser  Pro  Glu  Asp  Ser  Tyr  Gln  Val  Arg
               435                      440                      445

Thr  Arg  Gly  Arg  Cys  His  Leu  Cys  Val  Arg  Leu  Val  Arg  Ala  Cys  Asp
          450                      455                      460

Trp  Ser  Pro  His  Leu  Asn  Leu  Gly  Ser  Tyr  Leu  Gly  Leu  Pro  Pro  Ser
465                      470                      475                      480

Thr  Ala  Ser  His  Gly  Ser  Leu  Met  Leu  Pro  Pro  Ser  Thr  Ser  Phe  Leu
                    485                      490                      495

Ser  Arg  Ser  Leu  Phe
               500
```

( 2 ) INFORMATION FOR SEQ ID NO:14:

( i ) SEQUENCE CHARACTERISTICS:
        ( A ) LENGTH: 38 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:14:

```
Phe  Ile  Val  Ala  Ile  Leu  Tyr  Cys  Phe  Leu  Asn  Gln  Glu  Val  Arg  Thr
1                   5                        10                       15

Glu  Ile  Ser  Arg  Arg  Trp  His  Gly  His  Asp  Pro  Glu  Leu  Leu  Pro  Ala
               20                       25                       30

Arg  Arg  Thr  His  Ile  Lys
               35
```

( 2 ) INFORMATION FOR SEQ ID NO:15:

( i ) SEQUENCE CHARACTERISTICS:
        ( A ) LENGTH: 54 amino acids
        ( B ) TYPE: amino acid
        ( C ) STRANDEDNESS:
        ( D ) TOPOLOGY: linear ( i i ) MOLECULE TYPE: protein ( x i ) SEQUENCE DESCRIPTION: SEQ ID NO:15:

```
Phe  Ile  Val  Ala  Ile  Leu  Tyr  Cys  Phe  Leu  Asn  Gln  Glu  Val  Arg  Thr
1                   5                        10                       15

Glu  Ile  Ser  Arg  Arg  Trp  His  Gly  His  Asp  Pro  Glu  Leu  Leu  Pro  Ala
               20                       25                       30

Trp  Arg  Thr  His  Ala  Lys  Trp  Ala  Lys  Pro  Ser  Arg  Ser  Arg  Ala  Lys
               35                       40                       45

Val  Leu  Thr  Thr  Val  Cys
               50
```

( 2 ) INFORMATION FOR SEQ ID NO:16:

( i ) SEQUENCE CHARACTERISTICS:
        ( A ) LENGTH: 54 amino acids
        ( B ) TYPE: amino acid
        ( C ) STRANDEDNESS:
        ( D ) TOPOLOGY: linear (i) MOLECULE TYPE: protein (xi) SEQUENCE DESCRIPTION: SEQ ID NO:16:

| Phe | Ile | Val | Ala | Ile | Leu | Tyr | Cys | Phe | Leu | Asn | Gln | Glu | Val | Arg | Thr |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Glu | Ile | Ser | Arg | Lys | Trp | His | Gly | His | Asp | Pro | Glu | Leu | Leu | Pro | Ala |
|     |     |     | 20  |     |     |     |     | 25  |     |     |     |     | 30  |     |     |
| Trp | Arg | Thr | Arg | Ala | Lys | Trp | Thr | Thr | Pro | Ser | Arg | Ser | Ala | Ala | Lys |
|     |     | 35  |     |     |     |     | 40  |     |     |     |     | 45  |     |     |     |
| Val | Leu | Thr | Ser | Met | Cys |
|     |     | 50  |     |     |     |

(2) INFORMATION FOR SEQ ID NO:17:

(i) SEQUENCE CHARACTERISTICS:
  (A) LENGTH: 54 amino acids
  (B) TYPE: amino acid
  (C) STRANDEDNESS:
  (D) TOPOLOGY: linear (ii) MOLECULE TYPE: protein (xi) SEQUENCE DESCRIPTION: SEQ ID NO:17:

| Phe | Val | Val | Ala | Val | Leu | Tyr | Cys | Phe | Leu | Asn | Gln | Glu | Val | Arg | Thr |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Glu | Ile | Ser | Arg | Lys | Trp | Tyr | Gly | His | Asp | Pro | Glu | Leu | Leu | Pro | Ala |
|     |     |     | 20  |     |     |     |     | 25  |     |     |     |     | 30  |     |     |
| Arg | Arg | Thr | Cys | Thr | Glu | Trp | Thr | Thr | Pro | Pro | Arg | Ser | Arg | Val | Lys |
|     |     | 35  |     |     |     |     | 40  |     |     |     |     | 45  |     |     |     |
| Val | Leu | Thr | Ser | Glu | Cys |
|     |     | 50  |     |     |     |

(2) INFORMATION FOR SEQ ID NO:18:

(i) SEQUENCE CHARACTERISTICS:
  (A) LENGTH: 54 amino acids
  (B) TYPE: amino acid
  (C) STRANDEDNESS:
  (D) TOPOLOGY: linear (ii) MOLECULE TYPE: protein (xi) SEQUENCE DESCRIPTION: SEQ ID NO:18:

| Phe | Ile | Val | Ala | Val | Leu | Tyr | Cys | Phe | Leu | Asn | Gln | Glu | Val | Arg | Thr |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Glu | Ile | Ser | Arg | Lys | Trp | Tyr | Gly | His | Asp | Pro | Glu | Ile | Leu | Pro | Ala |
|     |     |     | 20  |     |     |     |     | 25  |     |     |     |     | 30  |     |     |
| Arg | Arg | Thr | Cys | Thr | Glu | Trp | Thr | Thr | Pro | Pro | Arg | Ser | Arg | Leu | Lys |
|     |     | 35  |     |     |     |     | 40  |     |     |     |     | 45  |     |     |     |
| Val | Leu | Thr | Ser | Glu | Cys |
|     |     | 50  |     |     |     |

MOLECULAR CLONING OF THE OVINE PITUITARY GROWTH HORMONE RELEASING HORMONE RECEPTOR

CROSS REFERENCE TO RELATED APPLICATIONS

This application is a continuation-in-part of U.S. application Ser. No. 07/902,826, filed Jun. 23, 1992; and a continuation-in-part of U.S. application Ser. No. 08/432,043, filed May 1, 1995, now U.S. Pat. No. 5,644,046.

This invention was made with U.S. Government support under grant DK45350 awarded by the National Institutes of Health. The government has certain rights in the invention.

FIELD OF THE INVENTION

This invention is directed to isolation, characterization, and production of hormone receptors, and is directed more particularly to methods and compositions useful in purifying and characterizing growth hormone releasing hormone receptor, isolation and sequencing of purified growth hormone releasing hormone receptor, cloning of a gene encoding for growth hormone releasing hormone receptor or biologically active fragments thereof, a living cell line possessing recombinant DNA encoding for growth hormone releasing hormone receptor or biologically active fragments thereof, and methods for producing growth hormone releasing hormone receptor and biologically active fragments thereof.

BACKGROUND OF THE INVENTION

Growth hormone releasing hormone (GHRH) is secreted by the hypothalamus, and stimulates the release of growth hormone (GH) from the anterior pituitary. GHRH is a member of a family of homologous peptides that includes glucagon, secretin, VIP (vasoactive intestinal peptide), PHI (peptide histidine isoleucine), PACAP (pituitary adenylate cyclase activating peptide), GIP (gastric inhibitory peptide), and helodermin. GHRH has been the subject of considerable study, but little is known about the GHRH receptor, GHRH-R, to which GHRH binds in the anterior pituitary to induce the release of GH.

Large scale production of the cloned GHRH receptor would enable the screening of large numbers of GHRH analogs, and would facilitate the development of improved agonists and antagonists in the clinical therapy of growth disorders. More specifically, the screening of large numbers of analogs and xenobiotics for GHRH activity could lead to the development of improved agonists for use in clinical therapy of growth hormone deficient children, and in clinical therapy of adults to improve nutrition and to alter body composition (muscle vs. fat). Such screening, possibly assisted by computer modeling based on receptor structure, could also lead to orally active non-peptide GHRH agonists that would be especially useful in medical and veterinary practice, for example, to develop higher yield milk production and higher yield, leaner livestock.

Commercial exploitation of drugs which interact with the GHRH-R will require a source of a purified form of GHRH-R and suitable binding assays.

The isolation and cloning of the GHRH receptor and its in vitro expression will also lead to: (1) in situ hybridization studies mapping the distribution of GHRH receptors throughout the body and to examination of their potential physiological role outside the pituitary; this might reveal potential roles for GHRH in the brain, gonad, pancreas, placenta, and gut, where the peptide is thought to be concentrated; (2) studies of receptor structure involving mutated or chimeric receptors to explore structure/function relations and second messenger interactions in the quest for specifically tailored agonist/antagonist molecules; (3) an understanding of the GHRH-R's evolutionary relation to other G-protein-linked receptors, especially those in the glucagon/secretin/VIP family; and (4) cloning of other members of this sub-family that are expected to have sequence similarity.

The ovine GHRH-R sequence can be used to map the binding site of GHRH on the ovine GHRH receptor and to compare GHRH-R sequence differences between species. Sequence differences between species allow identification of specific sites within receptor domains. Characterizing the binding site is an important step in development of GHRH antagonists and GHRH analogs and mimetics that could provide pharmacological means to modify growth hormone related effects.

There are several alternate routes towards obtaining functional receptor clones, such as: (1) purification of the receptor protein to obtain a partial protein sequence; this partial protein sequence could then be used to make probes for screening appropriate DNA for the corresponding nucleotide sequence; (2) screening DNA for sequences similar to known receptors thought to be related to the GHRH receptor; and (3) screening for DNA that, when expressed as protein, yields GHRH receptor, which would be detected by GHRH binding, biological activity, or by a GHRH receptor antibody. Note that any conceivable cloning method requires binding assays as well as functional assays with GHRH and related peptides in order to identify the GHRH receptor and to characterize expressed clones.

Unfortunately, purification of pituitary receptors is very difficult because of the scarcity of tissue, as well as the problems involved in solubilizing the receptors in active form, and in developing an efficient purification method. Even if the receptor protein can be isolated, the concentration of the receptor in the pituitary tissue is so low that it is exceptionally difficult to generate a sufficiently large amount of receptor to perform partial protein sequencing sufficient to generate DNA probes for the gene encoding for the GHRH receptor.

Further, since it is believed that the GHRH receptor is glycosylated, it may not be possible for bacteria to express biologically active receptor or fragments thereof.

There is thus a need for GHRH binding assays and compositions for use therein which will help characterize and isolate the GHRH receptor. In particular, there is a need for methods which can characterize the pituitary GHRH receptor in terms of size, glycosylation, solubility and stability of the receptor (GHRH-R)—ligand (GHRH or GHRH analog) complex, so that methods can be developed to purify the receptor protein and identify receptor clones. There is also a need for purified or partially purified GHRH-R and methods for obtaining same. By partially purified GHRH-R, it is meant that a GHRH-R isolate is formed having GHRH-R isolated from most of the organic matrix of the anterior pituitary cells. The GHRH-R isolate has a purity sufficient to allow for determining the GHRH-R sequence, with it being understood that this may require further purification to remove any remaining compounds which would interfere with sequencing, such as G-proteins. Nevertheless, the GHRH-R isolate of the present invention, produced using the extraction and isolation method of the present invention contains GHRH-R, preferably at a concentration greater than that at which GHRH-R is naturally present in the anterior pituitary, and the GHRH-R isolate can be further purified, if necessary, using SDS-PAGE to remove any compounds which would interfere with sequencing of the GHRH-R. Thus, the present invention also includes the production of GHRH-R of sufficient purity to conduct sequencing, or for use in bioassays of GHRH-R binding activity.

There is a further need for a method for cloning of a gene which encodes for the GHRH-R or biologically active fragments thereof, and for an isolated, purified, nucleic acid sequence or sequences encoding a growth hormone releasing hormone receptor and biologically active fragments thereof. There is also a need for a vector, host cell, or host organisms comprising a nucleic acid sequence encoding protein or polypeptides having the activity of GHRH-R.

Historically the GHRH-R has been difficult to work with since GHRH has very high non-specific binding (making it difficult to determine whether or not GHRH or GHRH analogs are binding specifically to GHRH-R), and GHRH-R has extremely low abundance. The nonspecific binding of GHRH analogs to glass and plasticware has been a major problem in previous work limiting the accuracy and reproducibility of receptor binding studies. Because of the "sticky" nature of the negatively charged GHRH peptide, the use of a simple filtration type binding assay has been impossible. Nonspecific counts are so high as to preclude detection of specific binding. In addition, the commonly used blocking agent polyethylenimine, which is used for blocking nonspecific binding of proteins on glass fiber filters is positively charged, and will bind GHRH analogs (negatively charged) nonspecifically. Further, a soluble receptor preparation with high binding affinity, which would vastly enhance efforts to purify the GHRH-R, has not been available.

Prior studies have characterized the GHRH receptor with respect to its affinity for probes, such as GHRH and related peptides, and linkage to G-protein. Attempts have also been made to use non-specific chemical cross-linkers to label the GHRH receptor. See, for example, Zysk, et al., "Cross-Linking of a Growth Hormone Releasing Factor-Binding Protein in Anterior Pituitary Cells," *J. Biol. Chem.*, 261:1678 (1986), and Velicelebi, et al., "Covalent Cross-Linking of Growth Hormone-Releasing Factor to Pituitary Receptors," *Endocrinology*, 118:1278 (1986). The results of these two studies suggest, respectively, the presence of a 26 KDa and a 70 KDa GHRH-receptor in the anterior pituitary. The discrepancy between the molecular weight found in these two studies emphasizes the difficulties involved in isolating and characterizing the GHRH-R, and the need for improved methods and compositions useful for isolating and characterizing the GHRH-R.

GHRH binding to the rat anterior pituitary is believed to be influenced by GTP, which causes the GHRH-receptor to reduce its affinity for GHRH (GTP is said to uncouple the G protein GHRH-receptor complex). The high affinity state of GHRH-R bound to GHRH is believed to be stabilized by interactions with a guanine nucleotide regulatory protein to form a hormone-receptor-G-protein ternary complex. GTP is hypothesized to destabilize the G-protein-receptor interactions, resulting in dissociation of the GHRH/GHRH-R-G-protein complex and reversion of the independent receptor to a low affinity state, while the liberated G-protein goes on to activate its respective second messenger system. See Struthers, et al., "Nucleotide Regulation of Growth Hormone-Releasing Factor Binding to Rat Pituitary Receptors," *Endocrinology*, 124:24–29 (1989).

It has been discovered that, in ovine and bovine anterior pituitary tissues, GHRH and its analogs are displaced by 500 to 1,000 fold lower concentrations of a GHRH analog, GHRHa (the preparation of which is described later) than VIP or PACAP. This finding is complementary to binding properties noted in the human pancreas (a source of secretin and VIP receptors) where the ability to stimulate adenylate cyclase in the presence of GTP shows an order of potency of secretin>helodermin>PHI$\geq$VIP>GHRH(1–27)NH$_2$. Similarly, using $^{125}$I-secretin, Kds obtained were secretin 0.8 nM, helodermin 200 nM, PHI 250 nM. VIP and GHRH (1–29)-NH$_2$ induce only 20% inhibition at 10 $\mu$M.

At supraphysiologic doses, GHRH is known to act at VIP receptors, and conversely VIP is a weak GHRH agonist.

Other articles which provide background information on isolation and characterization of hormone receptors include: Christopher, et al., "The VIP/PHI/secretin-helodermin/ helospectin/GRH Family: Structure-Function Relationship Of The Natural Peptides, Their Precursors And Synthetic Analogs As Tested In Vitro On Receptors And Adenylate Cyclase In A Panel Of Tissue Membranes," in *Peptide Hormones As Prohormones: Processing, Biological Activity, Pharmacology*, Ed. Jean Martinez, Pub. Ellis Horwood Lim., Chichester, England, 1989, Chichester, England. Laburthe, et al., "Molecular Analysis of Vasoactive Intestinal Peptide Receptors: A Comparison With Receptors for VIP Related Peptides," *Ann NY Acad. Sci.*, 527:296–313 (1988). Frohm, et al., "Growth Hormone-Releasing Hormone," *Endocr Rev.*, 7:223–253 (1986). Seifert, et al., "Growth Hormone-Releasing Factor Binding Sites In Rat Anterior Pituitary Membrane Homogenates: Modulation By Glucocorticoids," *Endocrinolgy*, 117:424–426 (1985). Bilezikjian, et al., "Desensitization To Growth Hormone-Releasing Factor (GRF) Is Associated With Down-Regulation of GRF-Binding Sites," *Endocrinology*, 118:2045–2052 (1986). Ishihara, et al., "Functional Expression and Tissue Distribution of a Novel Receptor for Vasoactive Intestinal Polypeptide," *Neuron*, 8:811–819 (1992). Ishihara, et al., "Molecular Cloning and Expression of a cDNA Encoding the Secretin Receptor," *EMBO J*, 10:1635–1641 (1991). Lin, et al., "Expression Cloning of an Adenylate Cyclase-Coupled Calcitonin Receptor," *Science*, 254:1022–1024 (1991). Juppner, et al., "A G Protein-Linked Receptor For Parathyroid Hormone and Parathyroid Hormone-Related Peptide," *Science*, 254:1024–1026 (1991). Frohman, et al., "Tissue Distribution and Molecular Heterogeneity of Human Growth Hormone-Releasing Factor in the Transgenic mouse," *Endocrinology*, 127:2149–2156 (1990). Paul et al., "Characterization of Receptors for Vasoactive Intestinal Peptide Solubilized From the Lung," *J. Biol. Chem.*, 262:158–162 (1987). Guijarro et al., "Solubilization of Active and Stable Receptors for Vasoactive Intestinal Peptide from Rat Liver," *Regulatory Peptides*, 25:37–50 (1989). Cronin et al., "Biological Activity of a Growth Hormone Releasing Factor Secreted By a Human Tumor," *Am. J. Physiol.*, 244 (Endocrinol Metab) E346–E353 (1983). Leong et al., "Enumeration of Lactotropes and Somatotropes in Cultured Male and Female Pituitary Cells: Evidence in Favor of a Mammosomatotrope Subpopulation," *Endocrinology*, 116:1371–1378 (1985). Munson, et al., "Ligand: a Versatile Computerized Approach For Characterization of Ligand-Binding Systems," *Anal. Biochem.*, 107:220–239 (1980). Wessel, et al., "A Method for the Quantitative Recovery of Protein in Dilute Solution in the Presence of Detergents and Lipids," *Anal. Biochem.*, 138:141–143 (1984). Bagnato et al., "Gonadotropin-Induced Expression of Receptors for Growth Hormone Releasing Factor in Cultured Granulosa Cells*," *Endocrinology*, 128, 2889–2894 (1991)

(compositions studied by Bagnato et al show GHRH binding properties which are different from binding properties of pituitary tissues). All articles and other documents mentioned herein are incorporated by reference as if reproduced in full below.

While the foregoing studies have been helpful in developing a preliminary understanding of the behavior of the GHRH-R, there remains a need for a sensitive and reproducible assay for the GHRH-R, which will enable the further characterization of the GHRH-R leading to the purification and cloning of the GHRH-R. Such an assay must overcome the problems of nonspecific binding of GHRH and GHRH analogs, and the low abundance of the GHRH-receptor. Iodination and purification of GHRH analogs with resultant high specific activity allows for the improvement of specific binding to crude anterior pituitary membranes.

Despite the multitude of paths to cloning and sequencing of the GHRH receptor that could be tried, substantial obstacles had to be overcome regardless of the path followed. An example of such problems is seen in efforts to clone and express the VIP receptor; initial claims to cloning and expression of the VIP receptor were repudiated in a later publication, and this served to misguide efforts to clone and express other receptors. See Sreedharan et al., "Cloning and Expression of the Human Vasoactive Intestinal Peptide Receptor," *Proc. Natl. Acad. Sci.* USA, 88: 4986–4990, (1990); Cook et al., "Characterization of the RDC1 Gene Which Encodes the Canine Homolog of a Proposed Human VIP Receptor," *FEBS Lett.*, 300: 149–152, (1991). With regard to cloning and expressing the GHRH-R, the tiny amount of GHRH-R present in mammalian organisms makes it difficult to gather a sufficient amount of purified receptor to determine enough of the amino acid residue sequence to construct oligonucleotide probes specific for the GHRH-R, which can then be used in screening a cDNA library. Further, it is necessary that a cDNA library be found which contains enough GHRH-R genes to give a strong enough signal to be distinguishable from homologous genes which may also hybridize to the probe. Finally, expression cloning, which involves repeated screening of transformed cells for expression of a receptor, is unpractical for cloning of GHRH-R, since existing techniques are not sensitive enough to be used in initial screenings for GHRH-R; this is due to non-specific binding and the very small amount of receptor. Thus, there remains a need for a method for cloning and expression of the gene encoding for GHRH-R and biologically active fragments thereof, as well as a need for a living cell line possessing recombinant DNA encoding for GHRH-R or biologically active fragments thereof. There is further a need for screening assays which utilize GHRH-R or biologically active fragments thereof for testing compounds which may interact with GHRH-R or fragments thereof. Since GRF must be administered via injection, such assays are critical in the search for compounds which can be administered orally and which interact with GHRH-R or fragments thereof. Such assays are also critical for finding other compounds which interact as agonists or antagonists for GHRH-R or fragments thereof. Therefore it is a primary object of the present invention to develop a sensitive and reproducible assay for GHRH binding to receptor.

It is a further object of the present invention to develop reagents to specifically and unambiguously label the GHRH-receptor.

It is yet another object of the present invention to develop a GHRH-receptor purification scheme and to obtain a GHRH-R isolate of sufficient purity, or capable of being readily purified to a purity, which will allow for at least partial sequencing of GHRH-R.

It is a further object of the present invention to produce purified GHRH-R.

It is a still further object of the present invention to provide a method for cloning a gene which encodes for GHRH-R or biologically active fragments thereof.

It is another object of the present invention to provide an isolated, purified, nucleic acid sequence encoding a growth hormone releasing hormone receptor or biologically active fragments thereof.

It is yet another object of the present invention to provide a vector comprising a nucleic acid sequence encoding a growth hormone releasing hormone receptor, or biologically active fragments thereof.

It is a still further object of the present invention to provide a host cell or living cell line comprising a nucleic acid sequence encoding a growth hormone releasing hormone receptor or biologically active fragment thereof.

It is a further object of the present invention to provide a pharmaceutical composition comprising GHRH-R or biologically active fragments thereof, and a therapeutic method for administering an effective amount of same to an organism to bind to endogenous GHRH, or to elicit antibodies which bind to the receptor and thereby induce or block activity.

Further, it is another object of the present invention to provide recombinant GHRH-R sufficient to allow large scale screening of peptides and xenobiotics for GHRH receptor binding ability.

SUMMARY OF THE INVENTION

These and other objects of the present invention are accomplished through an improved GHRH binding assay leading to the characterization and isolation of a crude GHRH-R extract (isolate). The present invention provides for cloning of the gene encoding for a GHRH-R and biologically active fragments thereof, and provides the amino acid sequences of a GHRH-R and biologically active fragments thereof, as well as oligonucleotide probes or primers which can hybridize to a gene encoding GHRH-R or fragments thereof. The present invention also provides for recombinant organisms and progeny thereof comprising a gene encoding for a GHRH-R and biologically active fragments thereof, said recombinant ("transformed") organism not expressing GHRH-R above background level or not containing said GHRH-R encoding gene prior to transformation. GHRH-R in pituitary membranes or in transformed or transfected organisms is characterized through the use of radio-iodinated probes formed from GHRH analogs. The GHRH analogs (GRFa, $GHRH_a$, or $GHRH_b$) and other analogs are iodinated in a preferred embodiment using solid phase iodobeads, and the monoiodinated material purified by reverse phase HPLC so as to be essentially carrier-free. Non-specific binding of GHRH analogs to glass and plasticware during delivery and dilution has been substantially eliminated by using organic solvents. In a preferred embodiment, fifty percent acetonitrile is used for dilution and delivery of GHRH analogs. GHRH and GHRHa specific binding to crude anterior pituitary membrane pellets is increased by addition of a pore-forming antibiotic. In a preferred embodiment, the antibiotic alamethicin (at approximately 0.05 mg/ml) is combined with homogenized anterior pituitary membrane pellets to increase GHRH specific binding.

GHRH analogs containing UV sensitive cross-linking groups (photoprobes or photoaffinity probes) have been prepared that demonstrate specific high affinity, GTP sensitive, cross-linking to the GHRH-receptor. Probes differ in both the location of the photosensitive group and the length of the spacer arm. Preferred photoprobes are formed by coupling of the GHRH analog [His$^1$, Nle$^{27}$]-GHRH-(1–32)-NH$_2$ to N-5-azido-2-nitrobenzoyloxysuccinimide (ANB-NOS), or to sulfosuccinimidyl-6-(4'-azido-2'-nitrophenylamino) hexanoate (sulfo-SANPAH or SANPAH), followed by iodination and purification. Preferably, coupling to the reagent ANB-NOS is targeted at the lysines at the 12 or 21 positions; the compound is subsequently iodinated on the tyrosine at the 10 position, and the product purified by reverse phase HPLC to form a photoprobe to be referred to as $^{125}$I-GHRH$_a$-ANB-NOS. In an alternate embodiment, the photoprobe $^{125}$I-GHRH$_a$-SANPAH is formed in a dimethylformamide solvent system by coupling of SANPAH targeted to the N-terminal histidine of GHRH$_a$, purification by reverse phase HPLC, iodination of the tyrosine at the 10 position of the GHRH$_a$, and repurification by HPLC.

It has been surprisingly discovered that, by use of the aforementioned photoaffinity probes, it is possible to produce a soluble complex of GHRH$_a$ bound to GHRH-R; the covalently cross-linked complex is readily soluble in a mild detergent solution, preferably containing a zwitterionic detergent compound capable of solubilizing proteins, such as 3-[(3-cholamidopropyl)-dimethyl-ammonio]-1-propane sulfonate (referred to as CHAPS, available from Pierce or from ICN Biomedicals, of Irvine, Calif.), and that most of the non-specifically cross-linked contaminants are not soluble in the mild detergent solution. It was then discovered that non-crosslinked complexes were also solubilized under these conditions. Photocrosslinking was performed after solubilization and proved that the receptor (GHRH-R) and ligand (GHRH-probe) had formed a stable soluble complex. In a preferred embodiment, this enables the elimination of up to about 90% of the non-specifically bound GHRH by extraction with a CHAPS containing solution, and removal of free peptide with charcoal/dextran. This results in a greatly improved GHRH binding assay.

In a further embodiment, a partially purified GHRH isolate is obtained through affinity chromatography by attachment of a function to GHRH or a GHRH analog, which has an affinity for a compound immobilized on a support. In a preferred embodiment, biotinylated derivatives of GHRH$_a$ are bound to GHRH-R, solubilized, and then immobilized on a streptavidin column; it has been discovered that the bound GHRH/GHRH-R complex disassociates at pH 5.0 in a buffer, thus forming a partially purified GHRH-R isolate, capable of being used to determine the amino acid residue sequence of the GHRH-R, which in a preferred embodiment occurs after further purification of the GHRH-R isolate using SDS-PAGE to remove compounds, such as G-proteins, which would interfere with sequencing, and thereby forming purified GHRH-R.

In yet another embodiment, the present invention provides for the cloning of a gene encoding for a GHRH-R and biologically active fragments thereof.

Preferably, a gene encoding for a protein or polypeptide having GHRH-R activity is isolated and connected with a vector DNA to form a recombinant DNA; the vector DNA including said gene is capable of replicating in a prokaryotic or eukaryotic cell. The gene encoding for a protein or polypeptide having GHRH-R activity is located downstream of a promotor in the vector, and is replicated as part of the vector. The recombinant DNA is then incorporated into a host cell, which did not previously contain said gene, to form a transformed or transfected cell line capable of expressing GHRH-R or biologically active fragments thereof.

In a preferred embodiment, a cDNA library, prepared from a growth hormone secreting pituitary tumor from a human acromegalic inserted in the vector λgt10, is screened at low stringency with a probe based on rat secretin receptor, RS-R, cDNA. It has been surprisingly discovered that probes based on rat secretin receptor cDNA will hybridize to at least a portion of the nucleotide sequence encoding for a GHRH receptor, yet clones representing the human secretin receptor are not found in any significant amount in the human acromegalic pituitary, HAP, tumor library. This surprising discovery (e.g., greater amounts of DNA encoding for proteins or polypeptides having GHRH-R activity than found in normal pituitary tissue, with no substantial competing activity from secretin or other related receptors) enabled the successful cloning of a gene encoding for protein or polypeptides having GHRH-R activity. Of great significance was the surprising discovery that rat cerebellum contained sufficient secretin receptor to be amplified using PCR to produce the RS-R probe used herein, despite a publication which taught that secretin receptor was not detectable in rat cerebellum. See Ishihara et al., *EMBO. J.*, 10:1635–1641 (1991).

Preferably, plaque purification of phage that hybridize to the RS-R probe is followed by excision of the cloned gene from λgt10, and by insertion into the plasmid pGEM7Zf(+) which is then used to transform *E. Coli.* The inserted gene is then sequenced by the dideoxy chain termination method following plasmid replication (amplification) in *E. Coli* and purification. A labeled oligonucleotide probe is then prepared from partial sequence(s) which resemble receptor cDNA, and used for high stringency screening of a second acromegalic pituitary, HAP, tumor cDNA library in the vector λBluemid, in which the inserts are contained in the pBluescript plasmid (which is capable of carrying for cloning purposes inserts as large as the theorized size of the entire gene encoding for GHRH-R). This enabled the cloning and sequencing of the entire GHRH-R. In a preferred embodiment, the gene encoding for GHRH-R is inserted into a eukaryotic expression vector, and the GHRH-R expressed is in a mammalian cell line.

Thus, the present invention relates to a substantially pure protein and biologically active fragments thereof having growth hormone releasing hormone (GHRH) receptor activity. The receptor is purified at least 10,000 fold relative to the membrane-bound receptor. By "biologically active fragments" is meant natural or synthetic portions of the full-length receptor which are capable of binding receptor-specific ligand, or which are capable of eliciting in a host animal GHRH-R specific antisera or a second messenger response while either conjugated to a carrier or in nonconjugated form. In a preferred embodiment, the receptor is derived from a human source, but homologous receptors are also derived from vertebrate species, such as but not limited to piscine, avian, ovine, caprine, bovine, porcine, murine, equine, canine, and feline.

The invention is also directed to pharmaceutical compositions comprising an effective amount of the pure receptor or fragments thereof, or proteins and polypeptides having GHRH-R activity in combination with a pharmaceutically acceptable carrier, and provides a method for the therapeutic use of such pharmaceutical compositions. The receptor and receptor fragments (proteins and polypeptides having GHRH-R ligand binding or immunological activity) are useful in screening methods for identifying GHRH analogs, as well as in identifying compounds which may act as GHRH antagonists at the receptor site. They also are useful in raising GHRH-R specific antibodies; such antibodies may, by blocking the receptor site, effectively prevent GHRH binding and thereby block growth. Other antibodies can be used to activate the GHRH receptor (e.g., thyroid stimulating antibodies, such as those causing Graves Disease). Pharmaceutical compositions containing the receptor or segment fragments can be used to treat disorders resulting from or associated with an excess of circulating GHRH. Such compositions can be employed for in vivo administration to bind circulating GHRH, thus preventing its binding to endogenous receptor.

In a preferred embodiment, the invention provides for an isolated nucleic acid sequence encoding a GHRH receptor, recombinant vectors including said sequence and host cells containing said sequence useful in production of a GHRH-receptor or biologically active fragments thereof (including proteins and polypeptides having GHRH-R activity).

In addition, the invention provides for molecular cloning of the ovine pituitary GHRH receptor. The ovine receptor sequence can be used to map the binding site of GHRH on its receptor and to compare differences between sequences of different species. For example, sequence differences between species allow identification of specific sites within receptor domains. Characterizing the binding site is an important step toward developing GHRH analogs, mimetics and antagonists that could provide pharmacological means to alter growth hormone related effects. Differences between the ovine GHRH-R sequence and other known GHRH-R sequences (human, porcine, rat and mouse), discussed in detail below, indicate that regulation of the ovine receptor is different from that for the known human, porcine, rat and mouse GHRH receptors. This may also be true for other closely related species, such as bovine, which are classified in the same suborder as ovine. Thus, the ovine GHRH-R, and possibly the receptors of other species such as bovine, may be susceptible to different means of pharmacological intervention than the known receptors.

BRIEF DESCRIPTION OF THE DRAWINGS

FIG. 1 is a bar chart demonstrating binding of $^{125}$I-GHRH$_a$ to crude ovine pituitary membrane pellets. The bars indicate the fraction of total counts bound to pellets after incubation with probe alone or in the presence of 10 nM GHRHa or 50 $\mu$M GTP$\gamma$S. Four different cases (sets of bars) are shown. The first case (membrane) shows binding to a preparation of crude membrane pellets. The second set (frozen) shows that there is little specific binding in the same membrane preparation after it has been frozen and thawed. The third set (DTT) shows binding to this same preparation (not frozen), but in the presence of 1 mM DTT. The fourth set (ala-wash) shows an improved protocol of the present invention which includes the pore forming antibiotic alamethicin and an additional wash step. Error bars indicate standard error of the mean, and N=3 or 4 replicates per point.

FIGS. 19(A–C) show the ovine GHRH receptor cDNA sequence SEQ ID NO:9 and encoded protein SEQ ID NO:10.

FIGS. 20(A–I) show in SEQ ID NOS:11–13 the locations on the ovine GHRH receptor cDNA sequence illustrated in FIG. 19 where it is cut with various restriction enzymes.

FIG. 21 shows a comparison of the ovine GHRH receptor C-terminus SEQ ID NO:14 with that for the porcine SEQ ID NO:15, human SEQ ID NO:16, rat SEQ ID NO:17 and mouse SEQ ID NO:18 GHRH-R.

DETAILED DESCRIPTION OF THE INVENTION

Figure 2A:
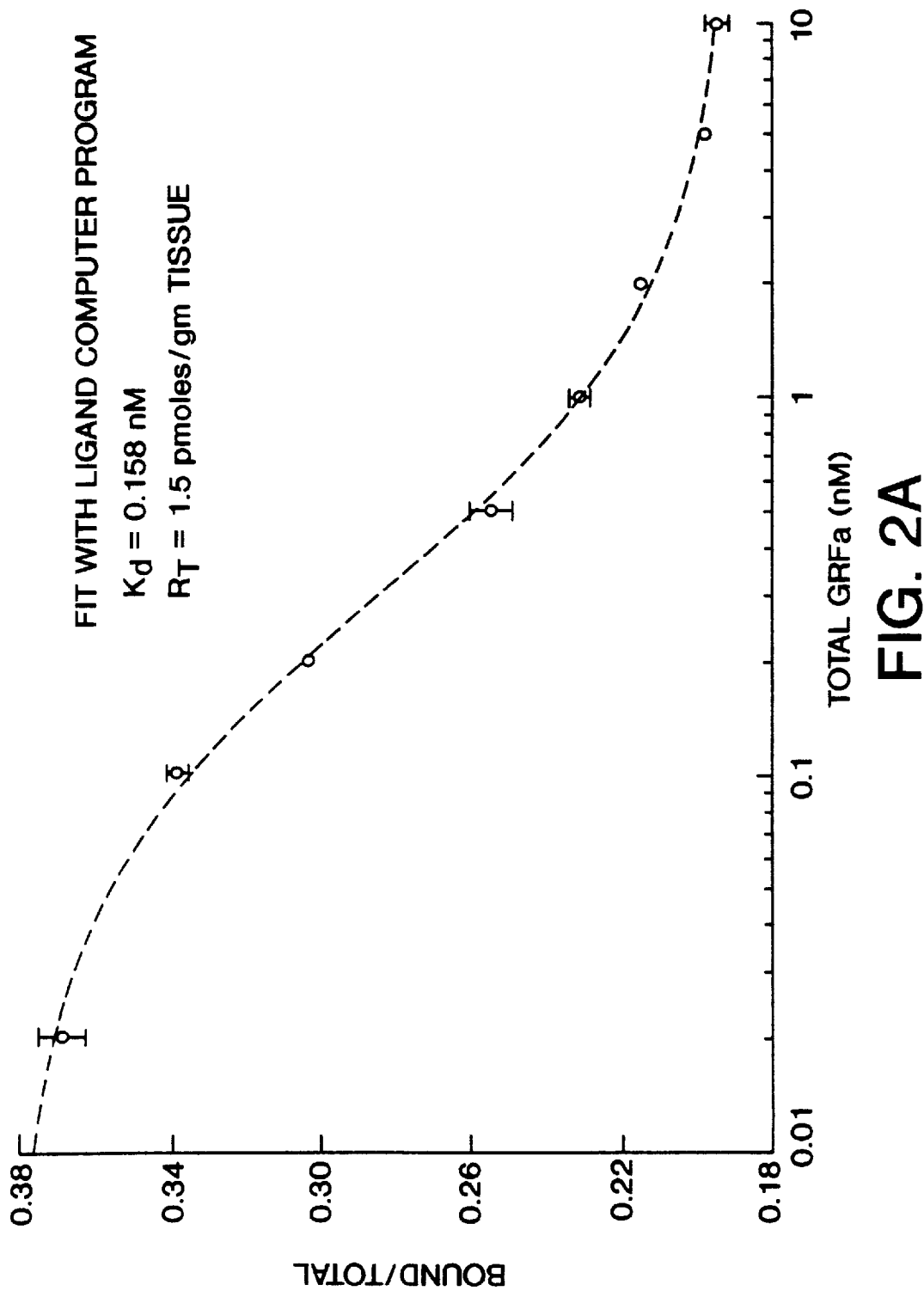
FIG. 2 is a graph used for saturation binding analysis. Points are data from binding assays performed in the presence of increasing levels of unlabeled GHRHa. Error bars indicate standard error of the mean. The inset shows a plot of the same data and curve in the Scatchard coordinate system (error base not shown on inset).

An overall approach to cloning of the GHRH-receptor involves (1) characterizing the GHRH-receptor, (2) using the knowledge of the characteristics of the GHRH-receptor to isolate the GHRH-receptor, (3) determining the peptide sequence of the GHRH-receptor (or of a portion of the GHRH-receptor), (4) determining the DNA sequence which is responsible for the production of the GHRH-receptor by use of degenerate oligonucleotide sequences (which may be from receptors believed to be homologous to the GHRH-R) to screen a cDNA library, and (5) cloning of the DNA sequence.

CHARACTERIZATION OF THE GHRH-R

GHRH-Binding Assay

In one aspect, the present invention is directed to a sensitive and reproducible assay for GHRH binding to the GHRH receptor, which demonstrates reversible high affinity GHRH-specific, GTP-dependent, binding. Because of the high nonspecific binding of the negatively charged GHRH peptide, use of a simpler filtration type binding assay has been impossible. With the assay of the present invention, specific binding (defined as the counts of gamma, γ, radiation produced by $^{125}$I-GHRH$_a$ binding which are eliminated from homogenized membrane pellets by 10 nM GHRHa) is 30 to 60% of the total counts bound in crude membrane pellets and up to 90% of the counts after extraction with a mild detergent (for example CHAPS) and charcoal/dextran treatment. A preferred embodiment of the binding assay of the present invention involves many factors, including a gentle solid-phase iodination protocol, HPLC purification of carrier free radioligand, an organic solvent system for the quantitative delivery of GHRHa, both plated cell and reverse hemolytic plaque assays to confirm the biological activity of the probe, and the use of about 0.05 mg/ml alamethicin, a pore forming antibiotic to increase specific radioligand binding to anterior pituitary membrane pellets. Alamethicin both increases specific binding and decreases trapped counts. A wash decreases recovered counts but further improves the relative amount of specific binding.

A preferred GHRHa analog for receptor binding studies is [His$^1$, Nle$^{27}$]-GHRH-(1–32)-NH$_2$ (referred to as GHRH$_a$). The GHRH analog is a peptide which has good GHRH-R binding activity, and differs from the human sequence in length, and has two amino acids, which are altered to facilitate its use as an iodination substrate. A preferred source of GHRHa is Peninsula Laboratories (Belmont, Calif.).

Preparation of iodinated GHRH analogs of optimal specific activity and biological activity is performed by first iodinating GHRH analogs (including photoprobes) using solid phase iodobeads (such as those available from Pierce), and then the monoiodinated material is purified essentially carrier-free by reverse phase HPLC, preferably using a fluorocarbon based Bio-Series Poly F column (available from MacMod). Quantitative dilution and delivery of GHRH analogs is obtained using organic solvents, preferably a 50% acetonitrile in water solution is used as a carrier. In this way, inaccurate and non-reproducible dilutions encountered with aqueous vehicles are avoided.

It has been surprisingly discovered that an approximately three-fold increase in specific binding, compared to prior methodology, is obtained when a pore-forming antibiotic is combined with crude anterior pituitary membrane pellets (See Struthers, et al., Endocrinology, 124:24 (1989). In a preferred embodiment, addition of about 50 μg/ml of the antibiotic alamethicin is utilized to obtain optimal specific binding.

With reference to FIG. 1, the binding of $^{125}$I-GHRH$_a$ probe to crude membrane pellets which have been treated under different conditions is presented. There are four sets of three bars. Each bar in a set indicates the fraction of total counts bound after incubation with iodinated probe. For each set of three bars, the left bar indicates total counts bound after incubation with iodinated probe alone, without pre-exposure of the membranes to cold GHRH or another compound known to compete with GHRH$_a$ or interfere with GHRH$_a$ binding. The center bar indicates the fraction of total counts bound after incubation with iodinated probe which has been added to the incubation together with 10 nM unlabeled GHRH$_a$ (which competes for specific binding sites). The difference between the leftmost and center bar of each set of bars indicates specific binding of GHRH, which represents the amount of GHRH-R present. The right hand bar indicates the fraction of total counts bound after incubation with $^{125}$I-probe in the presence of 50 μM GTPγS. Since GTPγS is known to cause dissociation of G-protein from some receptor complexes resulting in lowered affinity and decreased binding, the decrease in specific binding when using GTPγS is consistent with the presence of GHRH-R-G-protein complex.

Specific binding is defined as the difference in the binding seen with 20 pM iodinated analog alone and binding of the analog in the presence of 10 nM non-iodinated GHRH$_a$. Saturation binding, Scatchard analysis; competition studies, and other data discussed here show that these high affinity sites are specific binding sites.

Figure 2B:
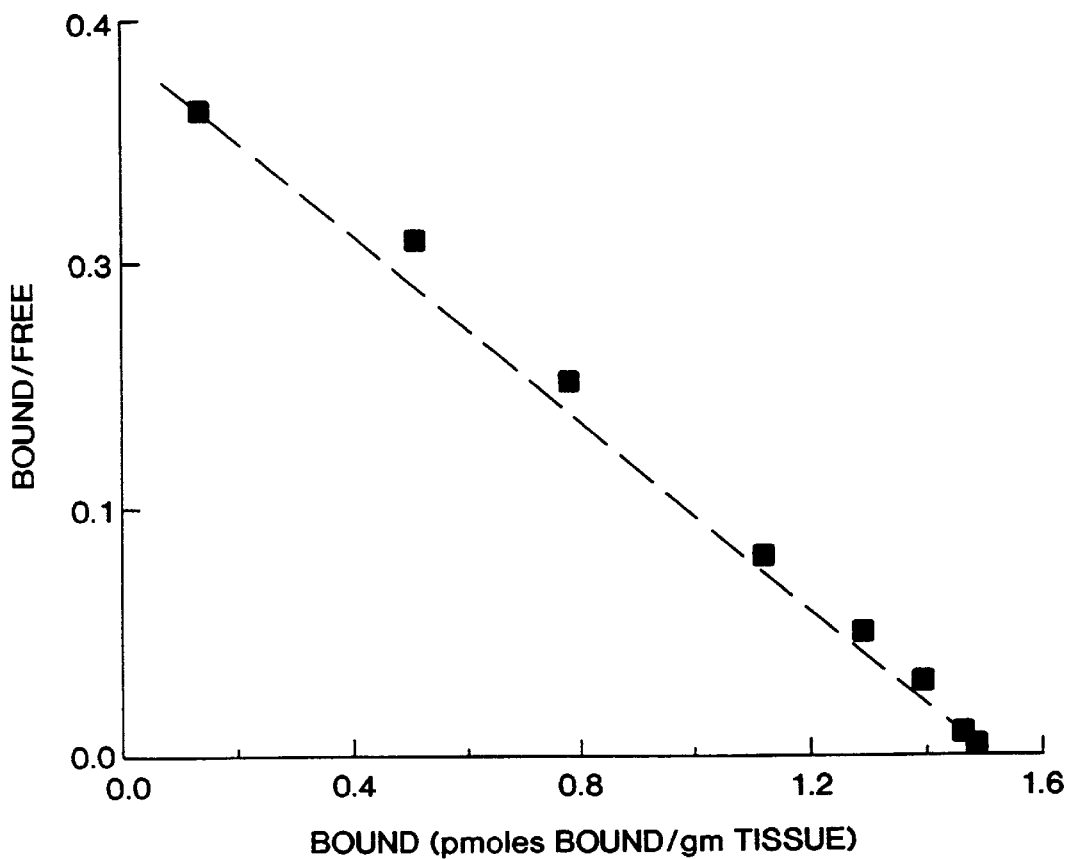

With reference to FIG. 2, saturation binding studies demonstrate binding of the GHRH analogue [His$^1$, Nle$^{27}$]-GHRH-(1–32)-NH$_2$ (GHRHa) to a single high affinity site with a Kd of about 160 pM. Some error bars were too small to show (N=6 replicates per point). This data was analyzed with the computer program Ligand, which determines binding constants based on a statistically weighted least squares fit to the ligand binding equation in a nontransformed coordinate system. The program reports a single binding site with a $K_d$=150±10 pM and R=1.5±0.09 pmoles/gm tissue (Best fit value=approximate SEM of fit). Statistical tests support this single binding site model. The dotted line is the theoretical curve generated using these constants in the binding equation.

Specific binding of GHRHa radioligand is reduced up to 65% by 50 μM GTPγS. The related peptides VIP and PACAP did not compete for this binding site at 100 nanomolar concentrations. This binding represents a high affinity G-protein linked GHRH-R. It is known that VIP binding to the VIP receptor is sensitive to sulfhydryl reducing agents. Such specific binding in the GHRH assay is completely eliminated by preincubation with 1 mM dithiothreitol (DTT, which is known to prevent high affinity binding to related receptors), thus further supporting the conclusion that the GHRH receptor is the binding site.

PHOTOAFFINITY PROBES

Photoaffinity probes were prepared using photoreactive cross-linking agents; these probes differ in both the location of the photosensitive group and the length of the spacer arm. The probes are capable of binding to GHRH-R in the absence of UV radiation and of cross-linking to GHRH-R under the influence of UV radiation. Preferred non-limiting examples of photoaffinity probes and methods for making same follow:

1) $^{125}$I-GHRHa-ANB-NOS

The 32 amino acid GHRH analogue [His$^1$, Nle$^{27}$]-GHRH-(1–32)-NH$_2$ (GHRHa) was coupled to the reagent N-5-azido-2-nitrobenzoyloxysuccinimide (ANB-NOS) targeted at lysine 12 or 21 to form GHRHa-ANB-NOS. The GHRHa-ANB-NOS was iodinated using iodobeads to form the radioligand ("photoprobe" $^{125}$I-GHRHa-ANB-NOS, "hot GHRHa-ANB-NOS" or "hot photoprobe") (preferred iodobeads are available from Pierce, Rockford, Ill.).

2) I-GHRHa-SANPAH

Figure 3:
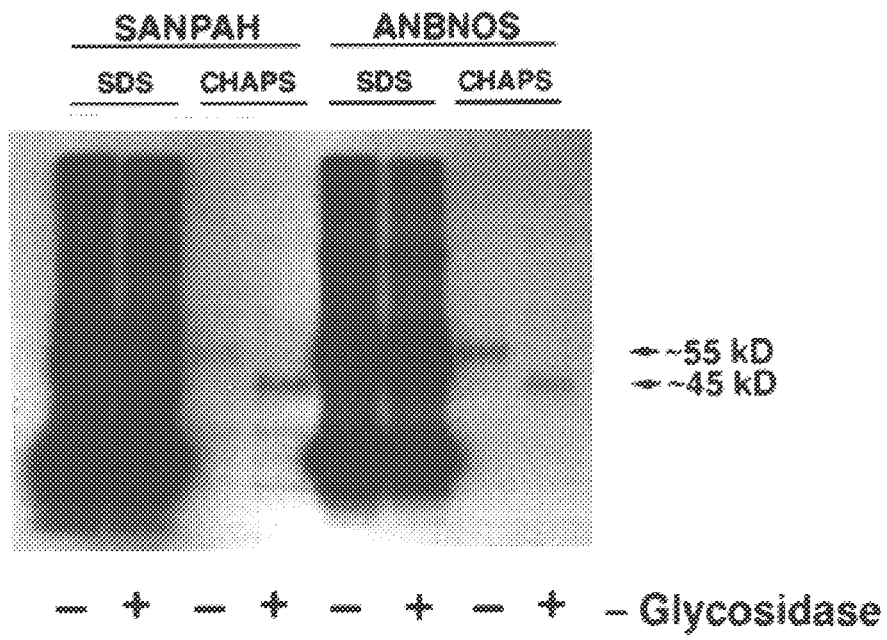
FIG. 3 is a radiograph of an SDS gel which demonstrates photoaffinity cross-linking of receptor. Cross-linking to crude ovine pituitary membranes is demonstrated with two different photoprobes (SANPAH and ANB-NOS), each extracted by two different methods (SDS and CHAPS). The effect of deglycosylating enzymes is also shown in each case. CHAPS extracts show greatly reduced nonspecific binding. Both photoprobes label a 55 kDa band that shifts to 45 kDa upon deglycosylation.
Figure 4:
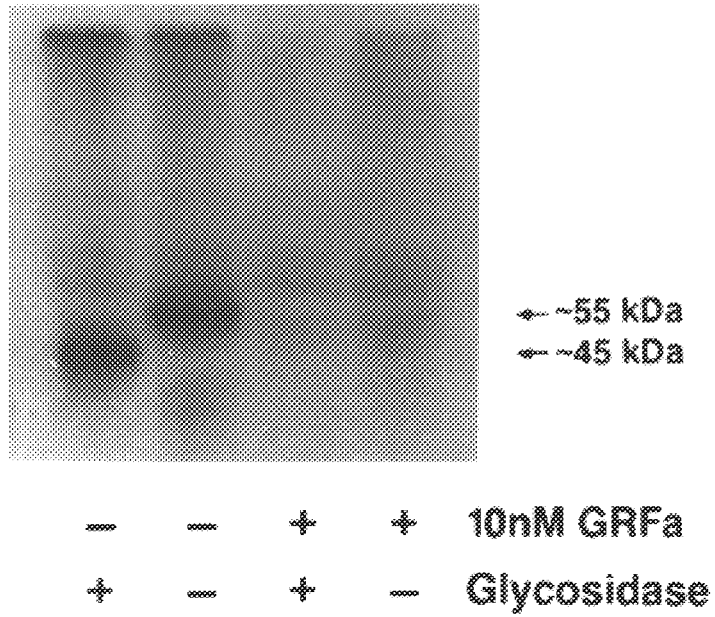
FIG. 4 is a radiograph of an SDS gel as in FIG. 3 showing CHAPS extracted ANB-NOS cross-linking which demonstrates competition by 10 nM GHRH and also shows deglycosylation.
Figure 5:
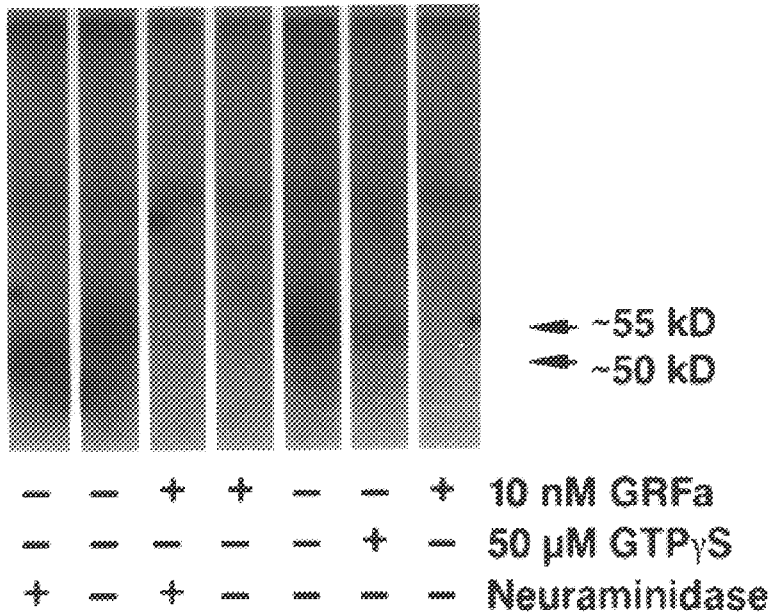
FIG. 5 is a radiograph of an SDS gel of photoaffinity cross-linking as in FIG. 4, which includes the effects of GTP$\gamma$S and also partial deglycosylation with neuraminidase.

In a dimethylformamide solvent system, the GHRH analog [His$^1$, Nle$^{27}$]-GHRH-(1–32)-NH$_2$ to N-5-azido-2-nitrobenzoyloxysuccinimide (ANB-NOS), was coupled to sulfosuccinimidyl-6-(4'-azido-2'-nitrophenylamino) hexanoate (sulfo-SANPAH or SANPAH) targeting at the N-terminal histidine of GHRHa. The radioiodinated material was then purified essentially free of starting peptide by reverse phase HPLC on a fluorocarbon based Bio Series Poly F Column (available from Mac-Mod Analytical, Chadds Ford, Pa.) using a shallow gradient of acetonitrile. Photoprobe binding in ovine pituitary membrane pellets was determined by γ-counting and UV induced cross-linking was examined by autoradiography of sodium dodecylsulfate polyacrylamide electrophoresis (SDS-PAGE) gels. $^{125}$I-GHRH$_a$-ANB-NOS probe bound with an affinity of about one nanomole, nM (compared to about 160 picomole, pM, for GHRH$_a$). SDS-PAGE revealed a band at about 55 kDa for ovine pituitary (in bovine pituitary, 57 kDa), which was completely eliminated in the presence of 10 nM GHRH$_a$; this band was reduced over 50% by 50 μM GTPγS, and was unaffected by 100 nM VIP. Thus, the 55 kDa band is due to photocrosslinking of the GHRH-R. FIG. 3 shows that this specific 55 kDa band is separated from most nonspecifically cross-linked material by CHAPS extraction. FIG. 4 demonstrates competition with 10 nM GHRHa. FIG. 5 demonstrates the effect of GTPγS on crosslinking.

Treatment of the cross-linked GHRH-receptor with neuraminidase caused the 55 kDa band to shift to 50 kDa, which is attributed to the removal of charged terminal sialic acid groups which decrease mobility in the gel (FIG. 5). Treatment of the cross-linked GHRH-receptor with a purified, protease-free mixture of endoglycosidase F and N-glycosidase F (available from Boehringer Mannheim of Indianapolis, Ind.) caused a shift in gel mobility to form a band at 45 kDa (shown in FIGS. 3 and 4); this indicates that the GHRH-receptor is an N-linked glycoprotein (common among G protein-linked receptors) and suggests the size of the deglycosylated protein chain. This size is consistent with the structure of VIP and secretin receptors.

Tests with immobilized lectins showed no binding of the cross-linked GHRH-receptor to wheat germ agglutinin, ricin, Limulus agglutinin, or concanavalin A. This makes the receptor unusual and offers an approach to the purification and isolation of this receptor from other receptors which do bind to these lectins. Following neuraminidase and β-galactosidase treatment, the receptor bound specifically to peanut agglutinin, providing an additional approach to separation and purification of the GHRH receptor.

SOLUBLE GHRH-GHRH-R COMPLEX AND IMPROVED BINDING ASSAY

Figure 6:
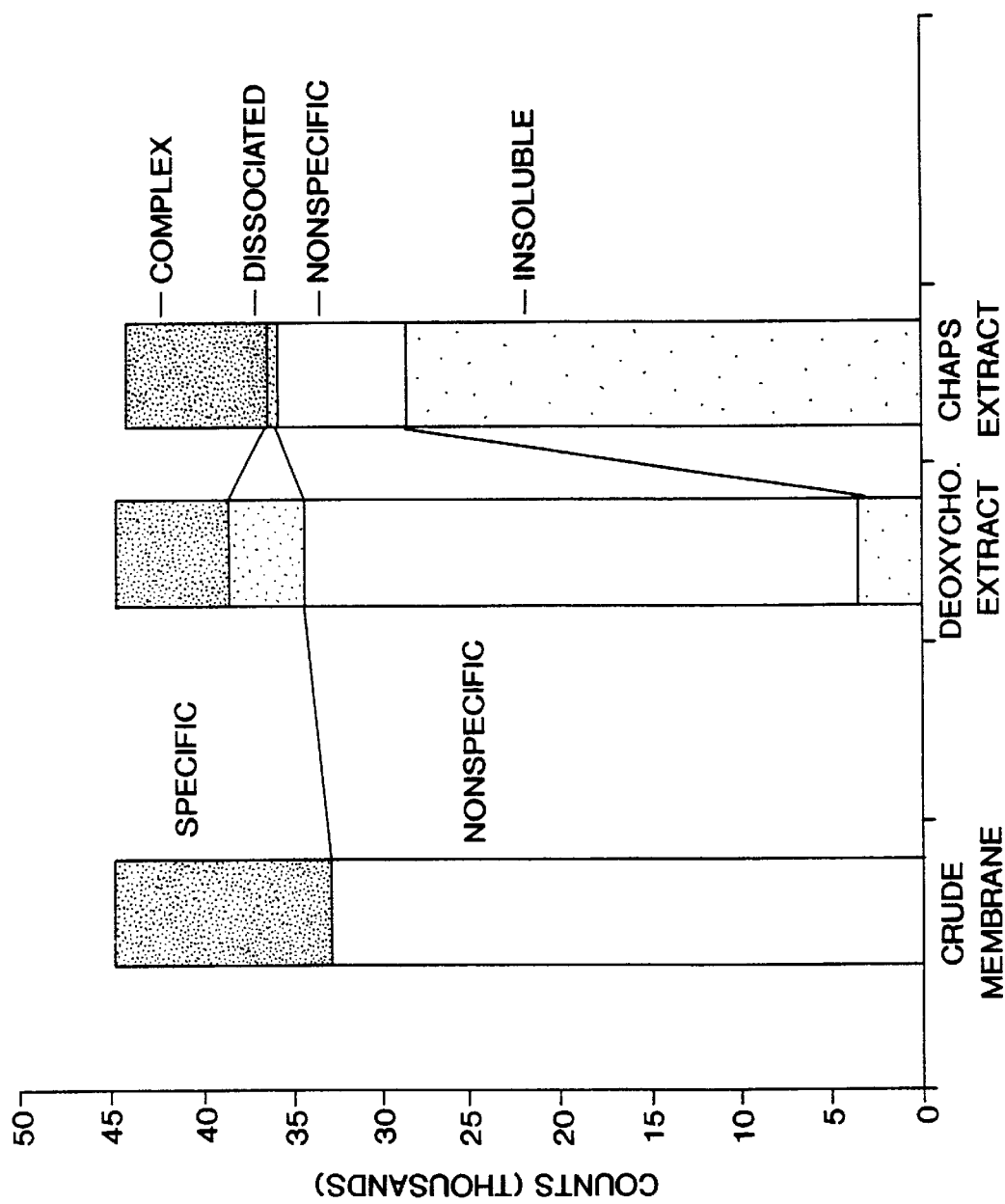
FIG. 6 demonstrates the solubility of GHRHa-GHRH-R complexes which were prepared by allowing radioiodinated GHRHa to bind to crude ovine pituitary membranes, in either the presence or absence of 10 nM unlabeled GHRHa.

Photoaffinity cross-linking showed that the covalently coupled receptor-ligand complexes are soluble in a mild detergent solution, preferably a solution containing CHAPS. Preincubating GHRH with the receptor, using the conditions of the aforementioned membrane binding assay, allowed CHAPS extraction and solubilization of an intact receptor-ligand complex even when not cross-linked. This complex was detected by gamma counting after detergent extraction of membranes incubated with $^{125}$I-GHRHa ("hot" GHRH$_a$) without crosslinking. FIG. 6 shows that most of the specific counts seen in the crude membrane were CHAPS extracted as a specific complex associated with receptor. The data for FIG. 6 was obtained as follows. Radioiodinated GHRHa was allowed to bind to crude ovine pituitary membranes either in the presence or absence of 10 nM unlabeled GHRHa. This was followed by detergent extraction and centrifugation; the supernatants were then charcoal/dextran treated to separate protein bound from free GHRHa, and the radioiodine in each fraction was counted. The labeled GHRHa bound in the crude membrane could thus be followed upon detergent treatment and characterized as: (1) insoluble, (2) soluble and nonspecifically bound, (3) specifically bound but detergent dissociated, or (4) soluble and specifically bound. As known from photocross-linking, most of the nonspecifically bound counts were not CHAPS soluble. Extraction with a deoxycholate detergent mix solubilized slightly more total counts, but much of this was unstable and dissociated, and nonspecific counts predominated.

Figure 7:
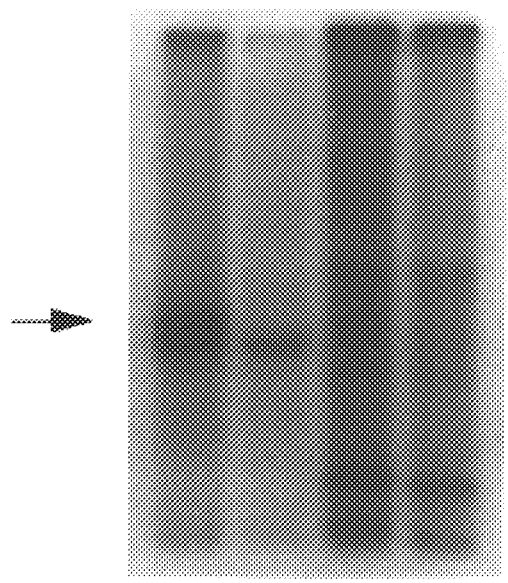
FIG. 7 demonstrates photoaffinity cross-linking of soluble complexes produced by following the experiment of FIG. 6 with ANB-NOS-GHRHa photoprobe, and the detergent soluble fraction was UV cross-linked after extraction. The leftmost two lanes were CHAPS extracted and the two lanes on the right were deoxycholate extracted.

FIG. 7 shows the results of this photocross-linking to confirm that this complex contained receptor. The membranes were prebound with photoprobe ($^{125}$I-ANB-NOS-GHRHa) in the dark, CHAPS extracted, and then cross-linked with UV. This proves that the GHRH was still bound to the solubilized receptor. In the CHAPS extract, most of the binding was in the 55 kD receptor band while in the deoxycholate case most of the bands were nonspecific. This matches well with the binding studies shown in FIG. 6 (though photoprobes have higher nonspecific binding), and demonstrates that the specific binding of the GHRH analog in the soluble complexes is to the 55 kDa receptor. Consistent with FIG. 6, the complex was much more stable in CHAPS than deoxycholate. There were also few nonspecific bands (One is just below the 55 kDa receptor band) upon photocross-linking of the CHAPS extract.

Figure 8:
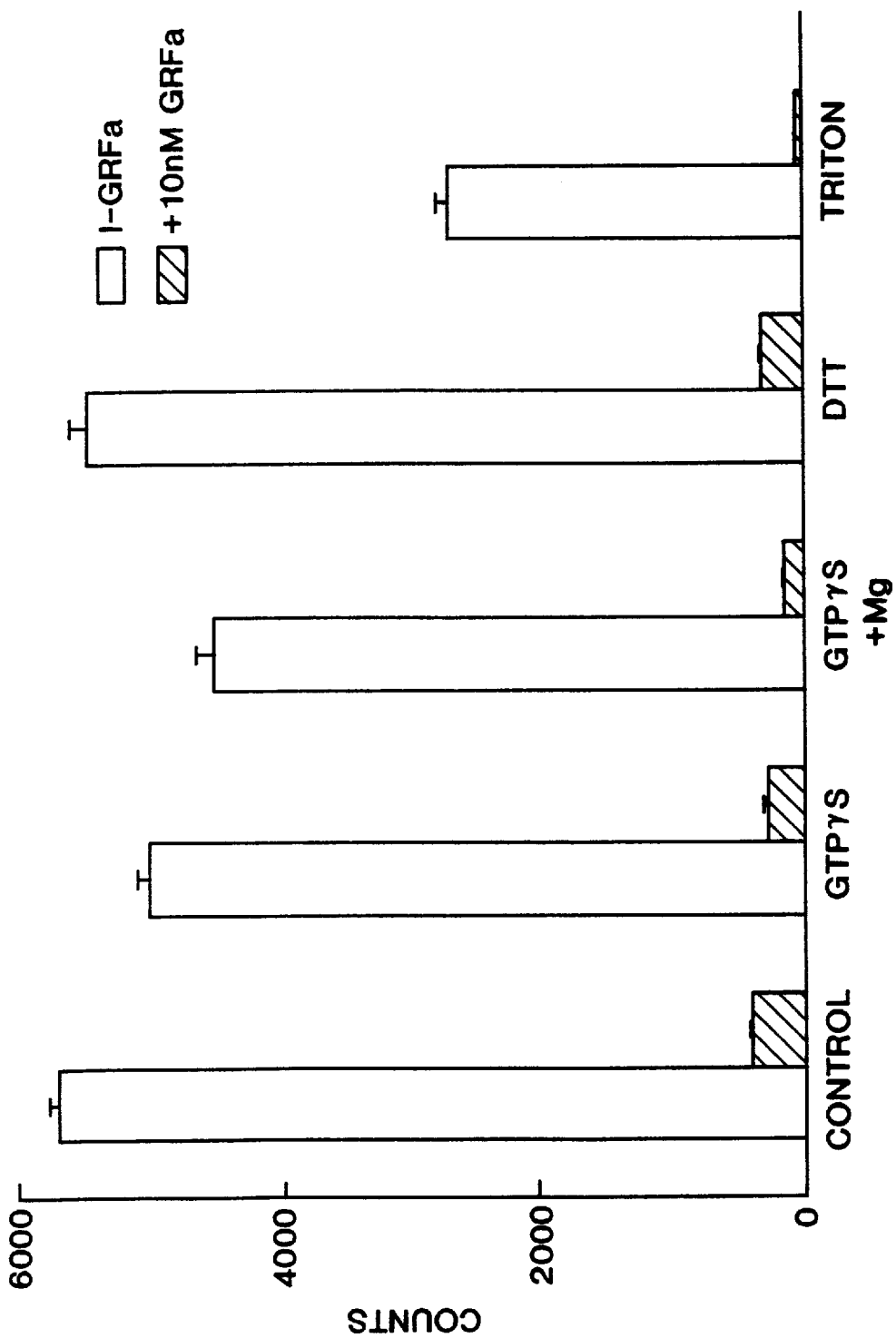
FIG. 8 demonstrates the stability of CHAPS solubilized, charcoal dextran treated GHRHa-GHRH-R complexes that were exposed to 50 $\mu$M GTP$\gamma$S ($\pm$5 MM Mg$^{++}$), 10 nM DTT, or 1% Triton X-100 for 30 minutes and then charcoal dextran treated again to quantify the amount of dissociation.

FIG. 8 demonstrates that CHAPS extraction amounts to an improved binding assay with greatly reduced nonspecific counts and increased sensitivity (Compare to FIG. 1). This figure also shows that the complex is partially dissociated by 50 μM GTPγS suggesting that G proteins are still associated with the complex solubilized in a detergent solution containing CHAPS. FIG. 1 shows that 1 mM DTT prevented specific binding before GHRH when added. FIG. 8 shows only a partial effect from 20 mM DTT after prebinding has occurred. This complex was also quite stable in up to 1M NaCl overnight at 4° C., but was completely dissociated by 1% triton X-100 (surfactant). Note the low background obtained when using CHAPS soluble, charcoal dextran treated samples for a binding assay.

Figure 9:
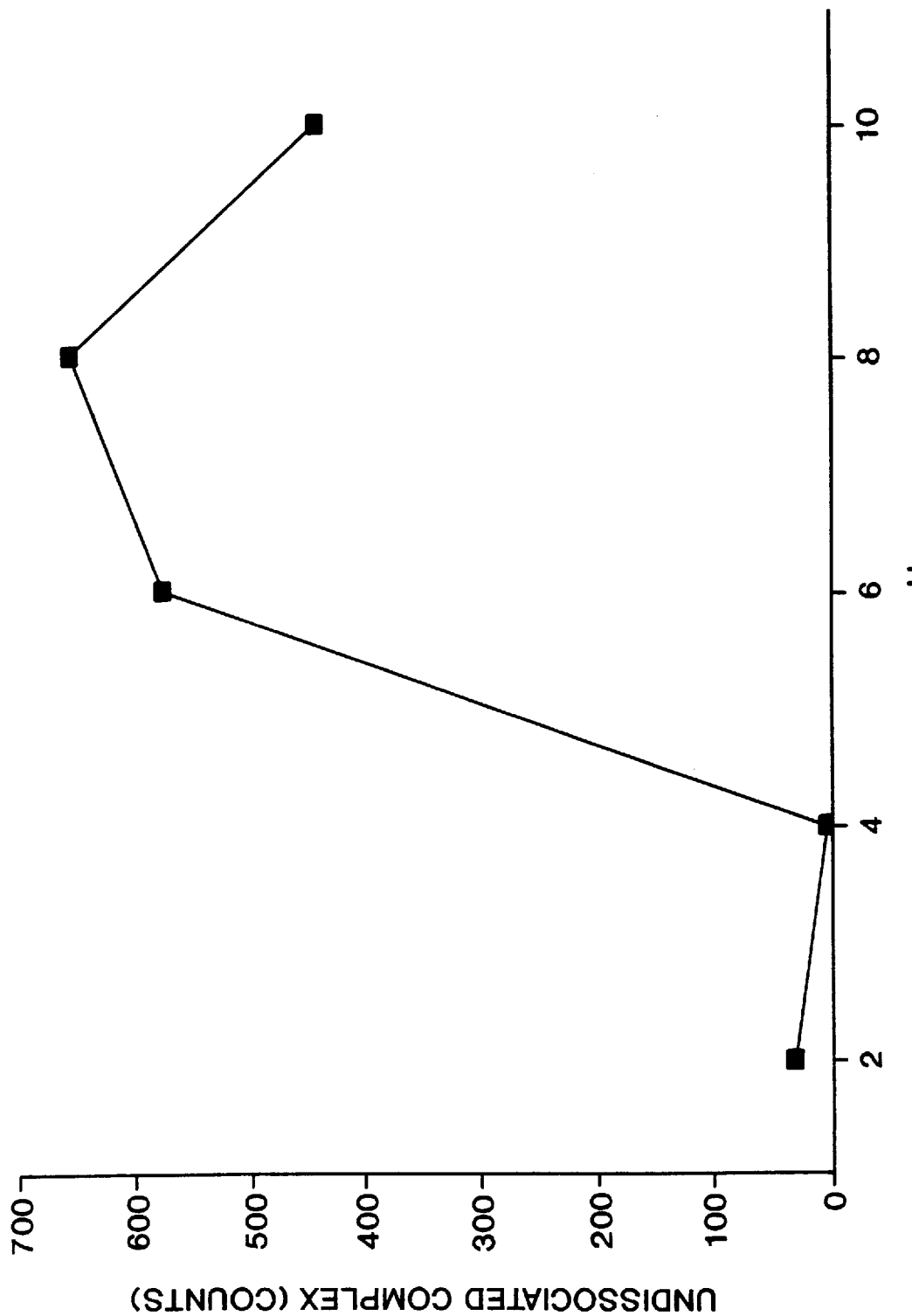
FIG. 9 demonstrates dissociation of soluble GHRH-GHRH-R complexes at low pH with stability of soluble specific complexes at varying pH evaluated as in FIG. 8. Further data indicates that near complete dissociation is obtained at pH 5 or below.

The pH stability of the soluble receptor-ligand complex is shown in FIG. 9. There is a sharp transition with the complex unstable at pH 5.5 and below, stable and able to exchange the bound GHRH with free GHRH between pH 5.5 and 6, and very stable and nonexchangeable at pH 7. The stability of this complex gives us both an improved GHRH-R binding assay, and the basis for a new receptor purification methodology.

ISOLATION AND PURIFICATION OF GHRH-R

Biotinylated GHRH analogs were developed with the aim of purifying the GHRH receptor as a receptor-ligand complex that can be retained on immobilized streptavidin. The first analog tested was [His$^1$, Nle27]-GHRH-(1–32)-NH$_2$ (GHRHa) biotinylated at lysines at the 12 and/or 21 positions using the N-hydroxysuccinimide reagent NHS-LC-Biotin (available from Pierce). This analog was iodinated at the tyrosine at the 10 position and resolved as mono and dibiotinylated forms on HPLC. Greater than 90% of these products bound to immobilized streptavidin within 30 minutes. The monobiotinylated GHRHa had two-fold reduced receptor binding affinity compared to GHRHa while the dibiotinylated had near zero activity. The biotin group appears to be in the receptor's binding pocket, as binding to streptavidin blocked binding to the receptor. The next analog tested was [His1, Nle27, Cys33]-GHRH-(1–33)-NH$_2$. It has a strong tendency to dimerize and none of the species that could displace GHRHa in a competition binding assay were biotinylated.

It has been surprisingly discovered that [His 1, Nle27, Biotin-Lys4 1 ]-GHRH-(1–41)-NH$_2$ (referred to herein as GHRHb) binds the receptor with an affinity comparable to GHRHa (a preferred source for preparing GHRHb is Nuros Corporation of San Jose, Calif.). To prove that this analog could be used in receptor purification, it was iodinated, a photosensitive cross-linking group (ANB-NOS) incorporated, and the compound purified by HPLC. This iodo-biotinyl-photoactivatable GHRH, 125I-GHRHb-ANB-NOS, was bound to receptors in crude bovine pituitary membranes. The receptor-ligand complexes were CHAPS solubilized, charcoal dextran stripped to remove free GHRH and bound to immobilized streptavidin.

To test if the streptavidin dislodged the receptor from the complex, samples were UV cross-linked before and after streptavidin binding and analyzed by autoradiography. This demonstrated that a significant fraction (30%) of the receptor that was available for binding could be retained on streptavidin beads. Studies of soluble receptor-ligand complex stability (see FIG. 9) indicate that a high salt (0.5M NaCl) wash of the streptavidin beads followed by a low pH elution (pH 5) (preferably using a phosphate, acetate, citrate or other suitable buffer solution) results in significant receptor purification to produce a GHRH-R isolate. The GHRH-R isolate obtained is of sufficient purity to allow for sequencing of the GHRH-R; in a preferred embodiment G-proteins and other interfering contaminants are removed, by methods, such as but not limited to gel electrophoresis in order to obtain GHRH-R of at least sufficient purity to perform sequencing.

Figure 10:
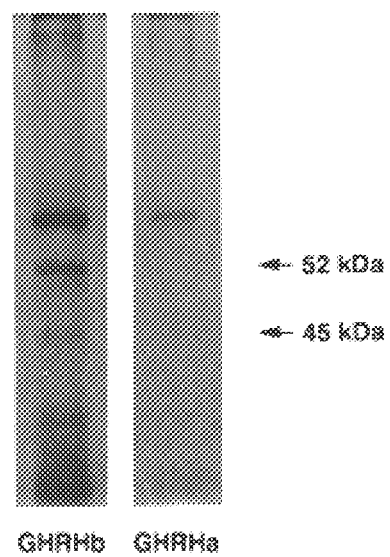
FIG. 10 demonstrates SDS-PAGE analysis of the eluate, containing purified GHRH-R, obtained from affinity chromatography of the biotinylated receptor complex GHRHb-GHRH-R on a streptavidin agarose column.

FIG. 10 demonstrates the results of affinity purification of the biotinylated receptor complex (GHRHb-GHRH-R) on a streptavidin agarose column. The agarose beads, having the bound complex, were washed in 0.5 m NaCl to minimize nonspecific binding and then the receptor was dissociated from the biotinylated ligand at pH 5.0, and eluted from the column. The eluate was concentrated by centrifuge-driven ultrafiltration, and analyzed by SDS-PAGE. A control column was run in parallel and treated identically except that the soluble receptor complexes were prebound with the nonbiotinylated analog GHRHa. The GHRHb lane on this silver stained gel shows bands at 52 and 45 kDa that are not seen in the GHRHa lane. The 52 kDa band corresponds to the size expected for the receptor because the 55 kDa band seen in crosslinking studies includes the covalently attached 3.6 kDa GHRHa peptide. The 45 kDa band is the size reported for the stimulator G-protein G$_S$ which is thought to be a subunit of the GHRH receptor complex. The coelution of these two bands and their absence in the control column confirms that highly purified GHRH-R has been prepared.

Confirmation of the GHRH-R is also proven by iodination of the purified protein corresponding to the band produced on an SDS gel having a molecular weight of approximately 52 kDa, and subsequent deglycosylation of this protein with endoglycosidase F, which shifts the band so as to correspond to a protein having a molecular weight of approximately 42 kDa. This shift reflects the same decrease in molecular weight for the photoaffinity labeled receptor.

Figure 11:
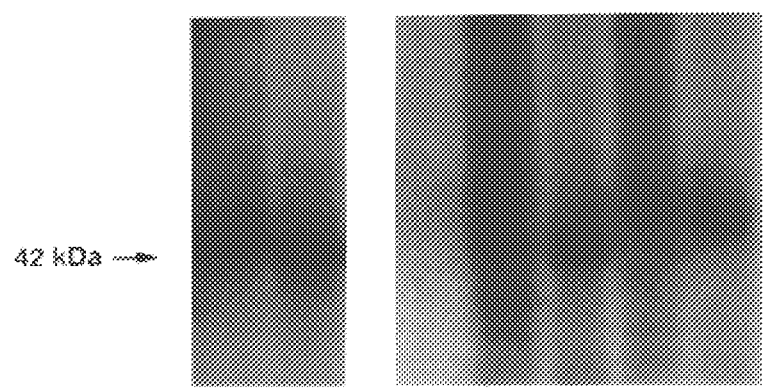
FIG. 11 demonstrates the deglycosylation behavior of purified GHRH-receptor as can be seen by mobility on an SDS gel. Seven samples were run corresponding to seven lanes on the gel. (Plus signs (+) indicate the presence of either $^{125}$I-purified receptor, photocross-linked receptor, N-glycosidase, or 10 nM GRFa). The leftmost lane illustrates the band produced by iodinated purified receptor, while the adjacent lane shows the band produced by treatment of the iodinated purified receptor with N-glycosidase, resulting in a molecular weight of approximately 42 kDa. The third lane from the left illustrates that 10 nM GRFa competed with an iodinated GRF analog capable of cross-linking to the receptor, so that no band can be seen. The fourth and fifth lanes illustrate the effect of N-glycosidase on iodinated purified receptor and iodinated photocross-linked receptor, respectively. An iodinated GHRH analog photocross-linked to GHRH-R and an iodinated purified receptor are run in lanes 6 and 7, respectively. Note that the photocross-linked receptor has a higher molecular weight, and that the samples treated with N-glycosidase have lower molecular weights.

With reference to FIG. 11, SDS gel electrophoresis illustrates the deglycosylation behavior of the purified GHRH receptor. In the leftmost lane, a band corresponding to iodinated purified receptor can be seen, having a molecular weight of approximately 52 kDa (to assist in reading the legend of FIG. 11, plus signs (+) indicate the presence of the compound listed to the left, while a minus sign (−) indicates that the compound to the left is not present). In the second lane, a single band, reflecting a protein with the molecular weight of about 42 kDa, is shown; this band resulted from the treatment of iodinated purified receptor with N-glycosidase. The third lane illustrates competition between 10 nM GHRHa ("GRFa") and iodinated GHRHa having a photo cross-linking group, which is capable of photo cross-linking to the receptor; since no band can be seen, it is clear that GHRHa displaces the $^{125}$I-GHRH. The fourth lane shows the effect of N-glycosidase on receptor photocross-linked to iodinated GRP. The sample in the fifth lane is identical to the sample in the second lane, and it is noted that the fourth lane shows that the protein producing band has a slightly higher molecular weight than the protein in the fifth lane, reflecting the increased molecular weight due to the photocross-linking group in the receptor GHRHa complex. The sixth lane shows the highest molecular weight band for receptor photo cross-linked to iodinated GHRHa. The sample in the seventh lane is identical to the sample in the first lane. Thus, FIG. 11 conclusively illustrates that GHRH-R has been purified and isolated.

The present invention encompasses the proteins and polypeptides produced by any means, whether synthetically, recombinantly, or by purification of the native protein, which have the activity of GHRH-R or fragments thereof (this includes vertebrate GHRH-R and biologically active fragments thereof). The protein sequence obtained from purified GHRH-R can be used to design oligonucleotide probes which are used to screen cDNA libraries from cells which express GHRH-R. Probes can also be based on receptors believed to be homologous to the GHRH-R. SEQ ID NO:1, SEQ ID NO:2, SEQ ID NO:3, AND SEQ ID NO:4 in the sequence listing presented just before the claims show, by way of nonlimiting examples, oligonucleotide sequences of primers useful for forming probes, via polymerase chain reaction, PCR, methodology; these probes are based on the published rat secretin receptor, RS-R and are useful in probing a cDNA library containing genes which encode for homologous proteins. Hybridization of probes with the library identifies the clone or clones containing the homologous genes or portions thereof. The gene or gene fragments are isolated from the clones, the whole gene reconstructed, and then ligated into an appropriate vector.

In one embodiment, the above mentioned probes, formed from the primers in SEQ ID NO:1 through SEQ ID NO:4 based on rat secretin receptor cDNA, are used to screen at low stringency a cDNA library prepared from a growth hormone secreting pituitary tumor from a human acromegalic in the vector λgt10 (such as that available from Clontech, of Palo Alto, Calif., #HL 1097a, oligo(dt) and random primed) (a non-limiting example of low stringency conditions includes a final wash at 42° C. in a buffer containing 30 mM NaCl and 0.5% SDS). This tumor type is thought to be monoclonally derived from pituitary somatotrophs, and is commonly responsive to GHRH, indicating the presence of functional GHRH receptors and suggesting that this is an enriched source of GHRH receptor mRNA. See Ikuyama et al., "Characterization of Growth Hormone-Releasing Hormone Receptor and Pituitary Adenomas from Patients with Acromegaly," *J. Clin. Endocrinol. Metab.*, 66: 1265–1271 (1988). For specific molecular cloning methods and laboratory techniques see Sambrook et al. ("Maniatis," *Molecular Cloning: A Laboratory Manual Second Edition,* Cold Spring Harbor Laboratory, Cold Spring Harbor, N.Y. (1989). Other articles which provide information on peptide hormones, protein purification, and gene cloning include Rosselin, "The Receptors of the VIP Family Peptides (VIP, Secretin, GRF, PHI, PHM, GIP, Glucagon and Oxyntomodulin). Specificities and Identity," *Peptides* 7: Suppl. 1, 89–100, (1986); Masu, et al., "Sequence of expression of a Metabotropic Glutamate Receptor," *Nature,* 349: 760–765, (1991); Houamad et al., "Cloning, Expression, and Gene Structure of a G-Protein-Coupled Glutamate Receptor from Rat Brain," *Science,* 252: 1318–1320, (1991); Tanabe et al., "A Family of Metabotropic Glutamate Receptors," *Neuron,* 8: 169–179; Abou-Samra et al., "Expression Cloning of a Receptor for Parathyroid Hormone-Related Peptide from Rat Osteoblast-like Cells: A Single Receptor Stimulates Intracellular Accumulation of Both CAMP and Inositol Trisphosphates and Increases Intracellular Free Calcium," *Proc. Natl. Acad. Sci. USA,* 89: 2732–2736, (1992); Libert et al., "Selective Amplification and Cloning of Four New Members of the G Protein-Coupled Receptor Family," *Science,* 244: 569–572, (1989); McFarland et al., "Lutropin-Choriogonadotropin Receptor: An Unusual Member of the G Protein-Coupled Receptor Family," *Science,* 245: 494–499, (1989); Battey et al., "Molecular Cloning of the Bombesin/Gastrin-Releasing Peptide Receptor from Swiss 3T3 Cells," *Proc. Natl. Acad. Sci. USA,* 88: 395–399, (1991); Hulmes et al., "Partial Amino Acid Sequence of a Somatostatin Receptor Isolated from $GH_4C_1$ Pituitary Cells," *Biochem. Biophys. Res. Comm,* 184: 131–136, (1992); Masu et al., "cDNA Cloning of Bovine Substance-K Receptor Through Oocyte Expression System," *Nature,* London, 329: 836–838, (1987); Spindel et al., "Cloning and Functional Characterization of a Complementary DNA Encoding the Murine Fibroblast Bombesin/Gastrin-Releasing Peptide Receptor," *Mol. Endocrinol.,* 4: 1956–1963, (1990); Straub et al., "Expression Cloning of a cDNA Encoding the Mouse Pituitary Thyrotropin-Releasing Hormone Receptor," *Proc. Natl. Acad. Sci. USA,* 87: 9514–9518, (1990); Sasaki et al., "Cloning and Expression of a Complementary DNA Encoding a Bovine Adrenal Angiotensin I Type-1 Receptor," *Nature,* 351: 230–233, (1991); White, et al., "Expression of Functional Pituitary Somatostatin Receptors in Xenopus Oocytes," *Proc. Natl. Acad. Sci. USA,* 87: 133–136, (1990); Abou-Samra et al., "The PTH/PTHrp Receptor Activates Adenylate Cyclase and Phospholipase C Through Two Distinct Molecular Domains," *Endocrine Society 74th Meeting,* Abstract 836, (1992).

Clones obtained from low stringency library screening were sequenced by the dideoxy chain termination method, and clones including partial sequences resembling receptor cDNA were utilized to produce human acromegalic pituitary, HAP, oligonucleotide probe(s), "HAP probes(s)". In a non-limiting example, the oligonucleotide sequences in SEQ ID NO:5 and SEQ ID NO:6 were hybridized to each other (note that there is a 10 bp overlap), and the Klenow fragment of DNA polymerase used to fill in unpaired sections with radiolabeled nucleotides. These HAP probes, SEQ ID NO:5 and SEQ ID NO:6, were then used for high stringency screening of a cDNA library prepared from acromegalic pituitary tumor mRNA that had been completely denatured by methylmercuric hydroxide to optimize the 5' extension of the cDNAs (available from Clontech 5' Stretch HL 1097v) (a non-limiting example of high stringency conditions includes a final wash at 65° C. in aqueous buffer containing 30 mM NaCl and 0.5% SDS). This cDNA was oligo(dt)-primed, size selected (>500 bp), and directionally cloned into the vector λ.Bluemid. This vector facilitates sequencing as inserts are contained in the pBluescript plasmid and do not need to be subcloned. Screening of this library with HAP probe(s) led to the identification of clones containing a GHRH receptor gene or portions thereof [as defined herein, genes encoding proteins or polypeptides having high affinity specific GHRH binding activity, as can be determined by the assays of the present invention, are considered to be a GHRH-R gene or portions thereof]. SEQ ID NO:7 provides the coding strand of the 1254 bp nucleotide sequence of a cDNA encoding for protein having GHRH-R activity; the sequence includes a stop codon, TGA (A represents deoxyadenylic acid, G represents deoxyguanylic acid, C represents deoxycytidylic acid, and T represents deoxythymidylic acid). SEQ ID NO:8 shows the 423 amino acid residue sequence of a protein having GHRH-R activity, corresponding to the nucleotide sequence of SEQ ID NO:7. The gene included in SEQ ID NO:7, or fragments thereof, was isolated from the clones, the whole gene reconstructed, and then ligated into an expression vector. Unfortunately, E. Coli could not be routinely or easily utilized as a host cell to produce the glycosylated protein. Therefore, it was necessary to find a suitable expression vector in which to insert a GHRH gene to enable expression in a mammalian cell. In a preferred embodiment, the expression vector CDM8, available from Invitrogen, of San Diego, Calif., is utilized, and the gene expressed in COS cells (a monkey cell line transformed by SV40 viral genome containing a defective origin of viral replication. When introduced into COS cells, cDNA inserted in pCDM8 directs production of mRNAs which are translated into protein).

The invention encompasses any and all host cells transformed or transfected by genes encoding for GHRH-R or portions thereof, as well as expression vectors used to achieve this transformation. It is contemplated that transgenic animals comprising mutated receptors, sense, or antisense mRNA to alter receptor function in vivo can be created.

Isolation of Nonhuman Homologous Receptor Subtypes

Homologous receptors from other tissue types or other species can be prepared as follows. cDNA libraries prepared from mRNA from the specific tissue type or species of interest are probed with radiolabelled HAP cDNA and washed under medium stringency (e.g., 1×SSC, 0.1% SDS, 55° C.). Plaques which appear positive are rescreened to verify authenticity. The positive plaques are then used in plasmid rescue according to techniques known in the art. Rescued plasmids are purified, cut with appropriate restriction enzymes, and analyzed in an agarose gel stained with ethidium bromide. The second gel is transferred to a nitrocellulose filter, probed with labelled HAP, washed sequentially under a medium, then high stringency (0.1×SSC, 0.1% SDS, at 65° C.) wash, and exposed to X-ray film. Those inserts which strongly hybridize to HAP under high stringency conditions represent likely receptor cDNA candidates. Further confirmation of the identity of these putative receptors can be accomplished according to the protocols described in the following examples, or in accordance with routine techniques known in the art. Thus, the invention encompasses not only the nucleotide and amino acid sequences depicted in the sequence listing but also nucleotide sequences which hybridize, under medium or high stringency conditions, with nucleotide sequence encoding the amino acid sequence of SEQ ID NO:8 as well as the biologically active proteins or fragments encoded thereby.

Screen Design and Utility

Screens use the purified or recombinant receptor in solid or liquid phase or in a host cell. Expression in the screen is measured by ligand binding, second messenger function, product secretion, or by other means. Solid phase assays can involve receptor attached to a solid support either chemically or immunologically in conjunction with or without transduction proteins. These assays can be linked to a reporter such as an antibody, biological chemical (e.g., biotin), or binding protein or enzyme, which will express a radioactive, chemical, calorimetric or luminescent signal. Screens involving host cells can employ bacterial or higher cells (e.g., yeast, insect, mammalian). Ideal mammalian host cells include pituitary tumor cell lines which secrete GHRH, and cell lines secreting other products in response to stimulation of the transfected GHRH-R.

Therapeutic Utility of the GHRH-R

The GHRH-R can be applied to the treatment of clinical growth deficiency in children and adults, can restore normal body strength and composition (muscle vs. fat), can slow or reverse some aspects of body aging related to body composition and muscle strength, can improve sleep control, and can be used to increase growth in domestic livestock, as well as increase lactation in milk-producing animals, and improve immune functions, appetite control, feed efficiency and nutrition.

PRODUCTION OF ANTIBODIES WITH GHRH RECEPTOR

The technique of hydrophilicity analysis of primary sequence information has been commonly used to identify both hydrophobic potentially membrane-spanning domains and hydrophilic antigenic sites. Analysis of the cloned GHRH receptor by the Hopp and Woods Method, see FIG. 18 (Hopp, T. P., and Woods, K. R., Proc. Natl. Acad., 78:3824 (1981) indicates seven domains rich in hydrophobic residues; this is a common property in the G-protein linked receptor family Wang, H., Lipfert, L., Malbon, C., and Bahouth, B., J. Biol. Chem., 264:14424 (1989). This model depicts four extracellular regions which are potential targets for binding of anti-receptor antibodies; three extracellular loops (EC-1, EC-2, EC-3) and an N-terminus which contains sites for asparagine-linked glycosylation.

For purposes of producing antibodies which block or activate the receptor, extracellular loop fragments, particularly those not containing N-glycosylation sites (carbohydrate may sterically interfere with antibody binding) are preferred. However, intracellular loops (IC) are also useful in production of antibodies which may be used for solid phase binding of the receptor protein in screening and other assays. A recent study of antibodies directed against the three EC loops of the thyrotropin receptor indicates a heterogeneity in their biological activities, including the induction of blocking antibodies using the EC-3 Loop as the antigen. See Ohmori, M., et al., Biochem. Biophys. Res. Comm., 174:399 (1991). Therefore, a broad panel of anti-peptide and anti-receptor antibodies is prepared and carefully evaluated in order to determine the epitopes required for the induction of blocking or activating antibodies.

Peptides are produced by conventional solid phase synthesis cleaved by HF, and HPLC purified (van Regenmortal, M. H., In Synthetic Peptides as Antigens, Elsevier, New York, pages 41–93 (1988). Peptides are coupled to a carrier immunogen such as keyhole limpet haemocyanin (KLH) or ovalbumin via glutaraldehyde by conventional procedures, and these conjugates used to immunize mice and rabbits. See Coligan, Jl et al., In Current Protocols in Immunology, Vol. 1, Wiley-Interscience, New York (1991). Animals are given the first immunization of conjugate peptide with Freunds Complete Adjuvant and three weeks later are given weekly booster immunizations with conjugate peptide in Freunds Incomplete Adjuvant. Specific anti-peptide antibodies are detected by their binding to peptide in an ELISA or RIA assay. In those instances where peptides do not adhere to plastic, and therefore are not amenable for direct assay, then the peptide is conjugated to an unrelated carrier protein which then adheres to the plate.

The specificity of the antibodies is also evaluated by the technique of Western Blotting. See Towbin, 1t. et al., *PNAS USA*, 76:4350 (1979). Specific antibodies reorganize a 55 kDa protein in crude membrane preparations, in WGA eluted glycoproteins, or in streptavidin eluates. Membranes from a cell line devoid of receptor serves as a negative control. This procedure also gives information about the degree of cross-reactivity of the antibodies with receptor subtypes from other cell lines and tissues (brain, pituitary) and obviates the need for receptor purification from each source. It is beneficial to obtain both tissue-specific antibodies for physiological studies and cross-reactive antibodies for possible use in purification of the receptor from various tissues using immunoaffinity chromatography.

Monoclonal antibodies to the GHRH receptor are prepared using conventional methods. See Harlow, H., and Lane, D., In *Antibodies: A Laboratory Manual*, Cold Spring Harbor Lab, New York, pages 139–240 (1988). The antigens used for immunization include (1) KLH-peptide conjugates corresponding to the extracellular regions as described above, (2) purified receptor from ovine or bovine anterior pituitary membranes, (3) purified receptor deglycosylated with neuraminidase or N-glycosidase and repurified by SDS-PAGE and electro-elution, (4) receptor purified from recombinant sources, such as transfected CHO cells, or baculovirus tested for reactivity to the peptide immunogen by ELISA or protein immunogen by Western blot. Those which display circulating antibodies to the receptor or its peptides are utilized for the preparation of hybridomas. Briefly, spleen cells are removed and fused in the presence of polyethylene glycol to SP2/D myeloma cells that are deficient in the enzyme hypoxanthine-guanine phosphoribosyl aminopterine-thymidine, which selects for true hybrids of both cell types since spleen cells do not grow in culture. Hybridoma supernates are screened for antibody to the receptor by (1) Western blots of purified receptor or WGA-eluted glycoproteins, (2) ELISA using inhibition of radiolabelled ligand binding to membranes. Those hybridomas which are positive are propagated and recloned by limiting dilution or growth in soft agar; this ensures their monoclonal nature. Positive clones are used to induce tumors in mice and accumulate the antibody in ascites fluid.

Both polyclonal and monoclonal IgG antibodies are purified by conventional ammonium sulfate precipitation and Protein A chromatography. See Harlow, supra. Antibodies are analyzed for their ability to block or activate radioligand binding to membranes in the standard binding assay described above.

Those antibodies that show promise for ligand blocking or activation are tested in vivo using for example a rat model, e.g., by using indwelling venous catheters on rats in order to monitor GH levels after administration of anti-GHRH receptor antibody. See Miell, J., et al., *J. Endocrinol*, 131:75 (1991). Those antibodies which show the most in vivo activity at this point are examined to define their epitopes (if not already determined) on the receptor. Those epitopes represent antigenic fragments of the receptor which when used as immunogens induce antibodies possessing the desired physiological effect of altering levels of GH production.

EXPERIMENTAL METHODS AND EXAMPLES

The following non-limiting examples further demonstrate the improved GHRH binding assay of the present invention, and method of purifying the GHRH-receptor based on solubilization of an intact GHRH/GHRH-receptor complex. The non-limiting gene cloning and protein expression examples which follow refer to exemplary nucleotide and amino acid sequences, SEQ ID NO:1 to SEQ ID NO:8. However, it is to be understood that the invention is not limited solely to these sequences, but also encompasses biologically equivalent sequences. Modifications to the sequence, such as deletions, insertions, or substitutions in the sequence which produce silent changes in the resulting protein molecule or portions thereof are also contemplated. For example, alterations in the gene sequence which reflect the degeneracy of the genetic code, or which result in the production of a chemically equivalent amino acid residue or residues at a given location in the protein, are contemplated. In particular, the invention contemplates those DNA sequences which are sufficiently duplicative of the sequence specifically disclosed so as to permit hybridization therewith under standard medium to high stringency Southern hybridization conditions, as well as the biologically active proteins produced thereby. The nucleic acid sequence or portions thereof disclosed herein can readily be employed in Southern hybridization procedures to identify and isolate GHRH-R in cells from a variety of species and tissue types; such host cells and their derivatives can be used in recombinant production of all or a portion of a GHRH-R.

It is to be understood that a wide variety of other materials than those specifically mentioned herein may be used to practice the invention without undue experimentation.

BINDING ASSAY IN CRUDE MEMBRANE PELLETS

Tissue Preparation

All steps were performed at 4° C. Frozen ovine or bovine anterior pituitaries (ovine: approximately 1 gm/pituitary obtained from Dr. Ian Clarke, Melbourne, Australia; bovine: approximately 2.5 gm/pituitary special handling from Pel-Freez, of Rogers, Ark.) were washed of blood, cleaned of connective tissue and homogenized (using a Dounce homogenizer) in 50 mM HEPES buffer, 100 mM NaCl, 10 mM EDTA, 0.1 $\mu$M EGTA, pH 7.4 with 0.5 mM PMSF (phenyl methyl sulfonyl fluoride), 10 $\mu$g/ml leupeptin, 10 $\mu$g/ml pepstatin A, and 200 U/ml (units/ml) aprotinin. This buffer is used to remove endogenous GTP which might be bound to G proteins and to restore high affinity binding. The homogenate was spun at top speed in a microfuge and the supernatant discarded. The upper (membrane) layer of the pellet was then gently resuspended in binding buffer containing 50 mM Tris buffer, 5 mM EGTA, 5 mM $MgCl_2$, 50 $\mu$g/ml alamethicin, 30 $\mu$g/ml bacitracin and other protease inhibitors as above.

Binding Conditions and Analysis

1/50 pituitary equivalent per tube was incubated in binding buffer with approximately 100,000 counts of iodinated probe in a volume of 500 $\mu$l at room temperature for 1 hour. The total counts delivered and the percent of counts bound for each tube was determined with 3 to 6 replicates per experimental condition. Saturation binding profiles were analyzed with the computer program Ligand which performs a statistically weighted least squares fit to the exact ligand binding equation in nontransformed coordinates. Statistical measures (F test and runs test) indicated a convincingly good fit to a single binding site model. A representative saturation binding analysis is presented in FIG. 2.

Results

Treatment of the tissue with 10 mM EDTA was essential to allow the removal of endogenous GTP and reveal the high affinity GTP dependant sites. Initially, nonspecific binding was overwhelming and a wide variety of blocking agents offered no improvement. Slightly better binding signals were seen in membrane fractions purified by sucrose density centrifugation. To obtain consistent results, large batches of crude membrane were prepared from frozen pituitaries and aliquots of this membrane were frozen for later assay. With reference to FIG. 1, a great increase in specific binding was noted when the membranes were tested directly after homogenation. One possible mechanism for this freeze-thaw effect is the formation of vesicles which interfere with the assay. In testing this possibility, it was found that the pore forming antibiotic alamethicin (50 ug/ml) increased the ratio of specific binding/total binding 3 fold, as is graphically illustrated in FIG. 1. Most of this increase was due to a drop in nonspecific binding, possibly due to the release of probe trapped in vesicles. An additional wash of the membrane pellets by centrifugation was included to maximize the enhancement of specific over nonspecific binding despite the loss in total counts recovered.

Computer analysis of saturation binding studies with the program Ligand indicates a single binding site with a $Kd=158\pm13$ pM and that the total number of specific binding sites (RT) is $1.5\pm0.09$ pmoles/gm tissue (best fit value±approximate standard error of means (SEM). Since the affinity for GHRHa is commensurate with GHRHa's biological potency, and because of specificity for GHRH over related peptides (no competition by 100 nM VIP or PACAP) and sensitivity to 50 uM GTPγS and to 1.0 mM DTT, this binding indicates the presence of GHRH-R.

Comparison of the $^{125}$I-GHRHa to a commercially available iodinated human GHRH (Amerisham, Arlington Heights, Ill.) showed much similarity; $^{125}$I-GHRH$_a$ displayed a slightly better specific binding and a somewhat stronger GTP effect.

Evaluation of Photoaffinity Probe Binding

Two different photoaffinity probes were prepared using heterobifunctional photoreactive cross-linking agents available from Pierce as discussed above (Rockford, Ill.). SANPAH was coupled to GHRHa targeted at the N-terminal histidine using a DMF solvent system. ANB-NOS was coupled to GHRHa targeted at lysines 12 or 21. Each coupling group-GHRHa product was purified by HPLC, iodinated and repurified.

Photoprobe binding to membranes was evaluated with crude membrane binding assay and then analyzed further by SDS-PAGE electrophoresis to identify the binding sites. Photoprobes were incubated in the dark, photolysed for 10 minutes with a long wave (366 nm) UV lamp, and then the samples were pelleted. The pellets were counted and then extracted by boiling directly in SDS sample buffer (total SDS extracts). Alternatively, the labeled pellets were extracted in a mild detergent solution (5 mM CHAPS) centrifuged, and the chloroform/methanol concentrated supernatants denatured with SDS buffer (CHAPS extracts). These samples were then electrophoresed in SDS gels and autoradiographed.

Results

Binding assay revealed that both photoprobes bound to membrane pellets, and could be totally displaced by 10 nM GHRHa, or partially displaced by 50 μM GTPγS. Both gave greater nonspecific binding than I-GHRHa. Gels of total SDS extracts of the affinity cross-linked pellets displayed this nonspecific binding as bands unaffected by GHRHa or GTPγS. These nonspecific bands differed somewhat from run to run and between the two probes (FIG. 3). The nonionic detergent CHAPS is a weak solubilizer of proteins; receptor purification work demonstrated the ability of solutions containing CHAPS to solubilize GHRH binding activity. When extracts of cross-linked pellets obtained by using a solution containing 5 mM CHAPS were examined on SDS gels, visualization of receptor cross-linking was much improved, as most of the nonspecifically labeled protein was not solubilized. With reference to FIGS. 3 and 4, a 55 kD band, whose labeling is greatly effected by GHRHa or GTPγS, is clearly visible with both probes, and represents the GHRH-R. These photoprobes are invaluable in the further characterization, purification and cloning of the GHRH-receptor.

DEGLYCOSYLATION

Since the extracellular portion of most G protein-linked membrane receptors is known to contain multiple carbohydrate groups covalently linked to arginine residues (N-linked), experiments were performed to confirm that the specifically photolabeled band in FIGS. 3 and 4 is an N-linked glycoprotein. Samples were treated with a purified, protease-free mixture of endoglycosidase F and N-glycosidase F.

Photolabeled pellets (extracted using SDS or CHAPS) were boiled in SDS sample buffer, diluted, and incubated overnight at 37° C. with 1.25% Nonidet P40 (a non-ionic detergent also known as NP-40) in either 0.5 units of glycosidase or blank. These samples were then concentrated by a chloroform-methanol precipitation protocol (see Wessel, et al., *Anal. Biochem.*, 138:141–143 (1984)) and electrophoresed on SDS gels.

With reference to FIGS. 3 and 4, it can be seen that the mobility of the specifically photolabeled band shifts from approximately 55 kD to approximately 45 kD only in the presence of glycosidase. Other bands, visible in the SDS extracted samples, and judged to be nonspecifically labeled by the lack of response to GHRH$_a$ or GTPγS, are not deglycosylated. This is the first proof that the GHRH-R is a glycoprotein, and provides the best estimate of the true size of the protein chain. As is shown in FIG. 5, treatment of the photolabeled receptor with neuraminidase caused a shift in gel mobility to approximately 52 kD. This demonstrates that the receptor has a number of terminal sialic acid groups on its oligosaccharide chains. These sialic acid groups also affect the receptor's pI, as seen on isoelectric focusing gels, hydrophobicity on HPLC, and also its lectin binding properties. Deglycosylation is useful in purification strategies and in facilitating proteolytic cleavage of the receptor for sequencing.

SOLUBILIZATION OF RECEPTOR-GHRH COMPLEXES

Pituitary membrane preparations solubilized in solutions containing CHAPS showed only GTP insensitive low affinity sites (Kd approximately 500 nM), as measured with a charcoal-dextran binding assay (adapted from that developed for VIP by Paul, et al., *J. Biol. Chem.*, 262:158–162 (1987)). Other detergents preserved even less binding, which indicates that the GHRH-R was not stable to these treatments. Photoaffinity crosslinking results revealed that the covalently coupled receptor-ligand complex is soluble in a solution containing CHAPS. Preincubating GHRH with the receptor using the conditions of the membrane binding assay of the present invention, followed by extraction with a mild detergent solution, preferably containing CHAPS, revealed solubilization of an intact receptor-ligand complex. This soluble complex was detected by detergent extraction of membranes incubated with $^{125}$I-GHRH analog, or $^{125}$I-GHRH analog following treatment with 10 nM cold GHRH.

PURIFIED GHRH-R

Biotinylated GHRH analog was then utilized to form a soluble $GHRH_b$-GHRH-R complex, and this soluble complex, following extraction using CHAPS, and purification with charcoal-dextran, was run over a streptavidin column. The streptavidin column was then washed with a NaCl solution, and subsequently a buffer solution having a pH of 5.0 was run over the column in order to produce a GHRH-R isolate.

The GHRH-R isolate can then be further purified by SDS-PAGE. A band appearing at about 52 KDa (corresponding to pure GHRH-R) can be blotted with a standard PVDF membrane. The PVDF membrane having purified GHRH-R thereon can then be digested on the membrane and sequenced to obtain the complete or partial amino acid residue sequence of the GHRH-R following conventional sequencing methods.

The amino acid residue sequence or sequences obtained from the sequencing step can then be utilized as a basis for forming degenerate probes for use in cloning of the gene responsible for production of GHRH-R.

Thus, an improved methodology for measuring binding of GHRH analogs to the GHRH receptor in ovine and bovine pituitary membranes has been disclosed (including methods for iodination, purification and delivery of GHRH analogs, and the use of pore forming antibiotics). This led to the development of methods for the GTP sensitive, GHRH specific, high affinity photo-labeling of the GHRH receptor. Such labelling of this receptor was not previously accomplished. This allowed for the characterization of the receptor's size, glycosylation, solubility and other properties. This led to the discovery that a mild detergent solution, including compounds such as CHAPS, could extract the bound GHRH-GHRH-receptor complex in a stable, soluble form. CHAPS extraction and charcoal/dextran treatment (to bind free GHRH) gives a soluble receptor-ligand complex that is purified from most nonspecific GHRH binding, and thus is very useful as a new, low background GHRH binding assay with better sensitivity than previously possible, and also as a starting point for receptor purification. This receptor-ligand complex is relatively stable to salt washes, GHRH exchange and GTP or DTT treatment, but not to lowered pH. A C-terminally biotinylated GHRH analog has been invented that, when bound in a soluble GHRH-R complex, allows for the purification of GHRH receptor by retention on a column of immobilized streptavidin, followed by a salt wash, and pH 5 elution. This purified receptor protein is suitable for partial sequencing of receptor peptides and this sequence information is valuable for the cloning of the GHRH receptor cDNA.

VECTORS

Figure 13:
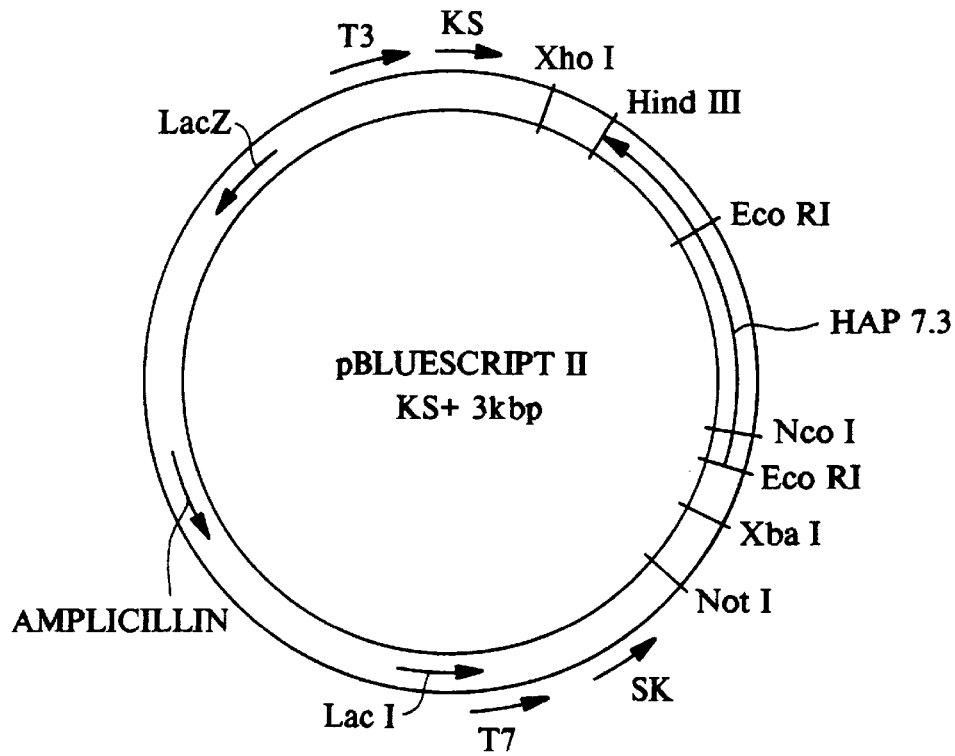
FIG. 13 is a representation of the plasmid pBluescript, illustrating the HAP insert, various restriction sites, and other features of the plasmid.
Figure 14:
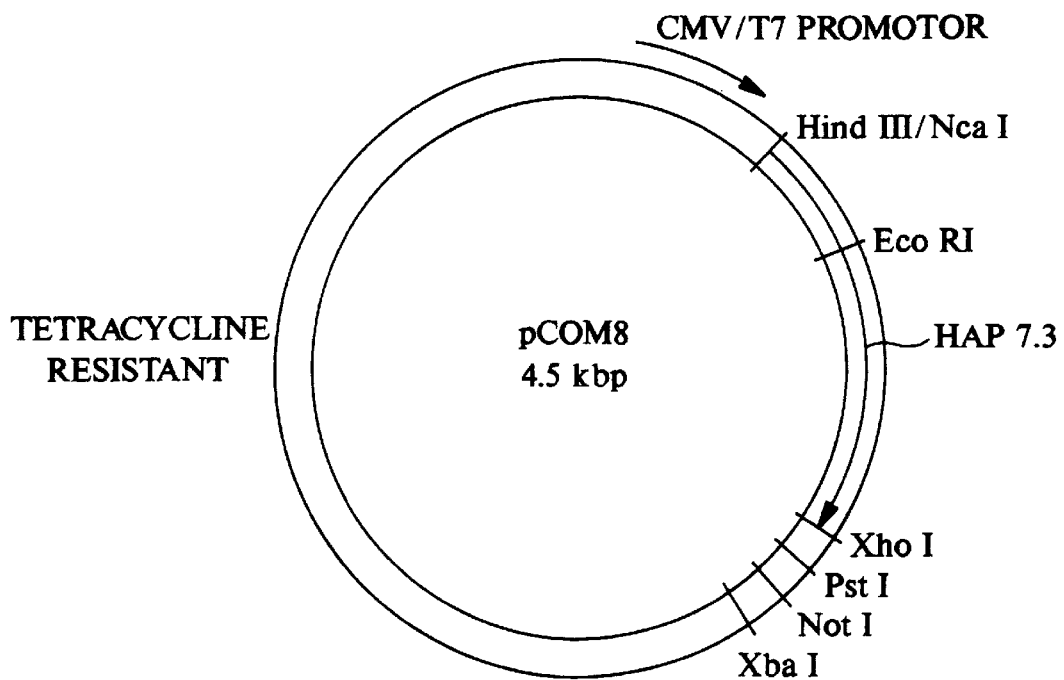
FIG. 14 is a representation of the plasmid CDM8 illustrating the HAP insert, relative locations of various restriction sites, and other features of the plasmid.

Non-limiting examples of suitable vectors for use in performing the present invention include the vectors represented in FIGS. 13 and 14. With reference to FIG. 13, the pBluescript® II KS+phagemid is represented. The pBluescript phagemid is a 2961 base pair phagemid derived from pUC19. The KS designation indicates the polylinker is oriented such that lacZ transcription proceeds from Kpn I to Sac I. The pBluescript phagemid is available from Stratagene, La Jolla, Calif. Specific information on pBluescript can be obtained from Stratagene and is available in published catalogs (such as the Stratagene 1991 Product Catalog). The pBluescript® II plasmid is shown containing a 1.6 kbp insert from HAP cDNA (to be defined further herein), which encodes for a GHRH-R. Restriction enzymes that cut before the 5' end of HAP include SacI, BstX, NotI, XbaI, SmaI, PstI, EcoRI. Enzymes that cut at 3' end of the HAP cDNA include HindIII, ClaI, SalI, XhoI, ApaI. Enzymes that cut within the HAP cDNA include NcoI and EcoRI.

With reference to FIG. 14, the vector CDM8, available from Invitrogen of San Diego, Calif., is represented. pCDM8 is a 4.5 kb multifunctional eukaryotic expression vector developed by B. Seed for cDNA cloning and analysis in *E. Coli* and eukaryotic systems. See *Nature* 32: 840–842, (1987). The plasmid CDM8 is shown containing a HAP cDNA insert. The Hind III, NcoI, and XhoI restriction sites shown were not reformed after blunt-end ligation of insert into the plasmid.

It is to be understood that other vectors may be used for cloning all or portions of the gene encoding for a GHRH-R or biologically active fragments thereof (such as, by way of non-limiting example, a proprietary expression vector of Merck Company designated pRJB2).

OLIGONUCLEOTIDE PROBES

In one embodiment, a first probe, based on rat secretin receptor cDNA was produced. Four oligonucleotides shown in SEQ ID NO:1 to SEQ ID NO:4 were synthesized to match portions of the sequence of the strands of the rat secretin receptor sequence disclosed by Ishihara et al., in "Molecular Cloning and Expression of a cDNA Encoding the Secretin Receptor," *EMBO. J.*, 10: 1635–1641 (1991). Two of these oligonucleotides, SEQ ID NO:1 and SEQ ID NO:2 were then used in performing the polymerase chain reaction, PCR, method, with cDNA from rat cerebellum in order to amplify the entire coding region of the rat secretin receptor cDNA. PCR was conducted as follows using a thermal cycler: cycle temperatures were 94° F., 55° F., and 72° F. for denaturing, primer annealing, and primer extension, respectively, and cycle times were approximately 1, 1.5, and 2.5 minutes, respectively, for these temperatures during each cycle. A total of 30 cycles were used. Taq Polymerase in standard PCR buffer was used. Unfortunately, the PCR reaction using the initial two primers (SEQ ID NO:1 and SEQ ID NO:2) did not give sufficient amplification. To overcome this problem, a second PCR reaction was performed using a second set of primers, SEQ ID NO:3 and SEQ ID NO:4 nested internally to the first set. The product was an 812 base pair "hydrophobic core" of the secretin receptor, which stretched from the first transmembrane segment, to just after the seventh transmembrane segment, nucleotides 639–1450 (the secretin receptor, like certain G protein linked receptors, GCRs, spans the cell membrane, and has multiple transmembrane segments formed of clusters of hydrophobic amino acids, and gives a hydropathy signature like that of the Rhodopsin GCRs). Restriction endonuclease mapping with Pst 1 and Xba 1 confirmed the identity of this material. The PCR product was purified as a band from an agarose gel by electrophoresis onto diethylaminoethyl, DEAE, paper, followed by salt elution and ethanol precipitation.

LOW STRINGENCY LIBRARY SCREENING

The secretin receptor cDNA fragment produced above was then radiolabeled by random priming, and used as a probe for screening about $1.5 \times 10^6$ clones that had been plated from the λgt10 cDNA library from human acromegalic pituitary, and lifted onto nitrocellulose filters. In a preferred embodiment, labeling of probes is conducted using a Prime-a-Gene kit available from Promega of Madison, Wis. (generally, low stringency conditions comprise elevated ionic strength and/or decreased temperature; high stringency conditions comprise decreased ionic strength and/or increased temperature). The filters were washed at 42° C. in a buffer containing 30 mM NaCl in 0.5% sodium dodecyl sulfate, SDS, prior to autoradiography. Phage that hybridized to the probe were plaque-purified, CsCl banded, the inserts in the λgt10 were excised with EcoRI, subcloned into pGEM7Zf(+) (available from PROMEGA of Madison, Wis.), and cultured in *E. Coli*. The cloned inserts in the pGEM7Zf(+) were then sequenced by the dideoxy chain termination method of Sanger et al., in "DNA Sequencing with Chain Termination Inhibitors," *Proc. Natl. Acad. Sci. USA*, 74: 5463–5467 (1977). Several small (<400 bp) and three larger clones were found. Two of these larger clones (1.0 and 1.1 kb) each included partial sequences resembling receptor cDNA (HAP sequence), and a non-coding 3' section ending in a poly A tail. These clones contained identical sequences where they overlapped, but differed in the length of coding region included by 200 bp, and demonstrate two different 3' polyadenylation sites 300 bp apart. It was surprisingly discovered that no clones representing the human secretin receptor, which should be readily detected by the rat secretin probe used, were found in the acromegalic tumor, HAP, library. [This is particularly significant, since the GHRH-R is present in extremely low concentrations in the pituitary somatotroph, and the presence of even relatively small amounts of the gene encoding for the human secretin receptor in the cDNA library would make cloning of the GHRH-R by this method difficult].

HIGH STRINGENCY LIBRARY SCREENING

A labeled 50 bp HAP oligonucleotide probe made from the two complimentary 30 mers shown in SEQ ID NO:5 and SEQ ID NO:6, which overlap by 10 bp; the hybridized mers were labeled with a Klenow fragment fill-in reaction (these mers were prepared based on the sequence obtained from the low stringency library screening). The 50 bp HAP probe was used to screen the Clontech #HL 1097a human acromegalic cDNA library discussed above, as well as to screen a Clontech 5' stretch HL 1097v library specially prepared from acromegalic pituitary, HAP, tumor mRNA that had been completely denatured by methylmercuric hydroxide to optimize the 5' extension of the cDNAs; this cDNA was oligo(dt)-primed, size selected (>500 bp), and directionally cloned into the vector λBluemid. This vector facilitates sequencing as inserts are contained in the pBluescript plasmid and do not need to be subcloned as had to be done when using the vector λgt10 above. Both libraries were screened as above, but a high stringency final wash of the nitrocellulose filter lifts at 65° C. was used to remove all but the closest matches. A library using the λgt10 vector produced 152 signals that were confirmed by duplicate lifts.

Screening of the second "5' stretch" library with duplicate lifts revealed 64 matching signals, 58 of which were plaque purified; of these, the 7th, designated HAP 7, was suggested by PCR to contain the complete protein encoding region for a GHRH-R. More specifically, by use of PCR primers to the phage vector that brackets the cloning site and also by use of primers specific to the HAP sequence, it was possible to measure both the total size of each insert and its length 5' to the known HAP sequence using PCR. The results suggest that the HAP cDNA is abundant in both of these tumor libraries and that a full-length clone was produced.

The HAP 7 phage was cut with the restriction endonuclease NotI to remove the plasmid pBluescript containing the cDNA insert. This plasmid was then used to transform *E. Coli* and transformed cells were selected by resistance to ampicillin; one of the colonies designated *Escherichia Coli* HAP 7.3, DH5α was deposited with the American Type Culture Collection, 12301 Parklawn Drive, Rockville, Md. 20852, U.S.A., on Aug. 25, 1992, and has been given the Accession Number ATCC 69058.

Figure 12:
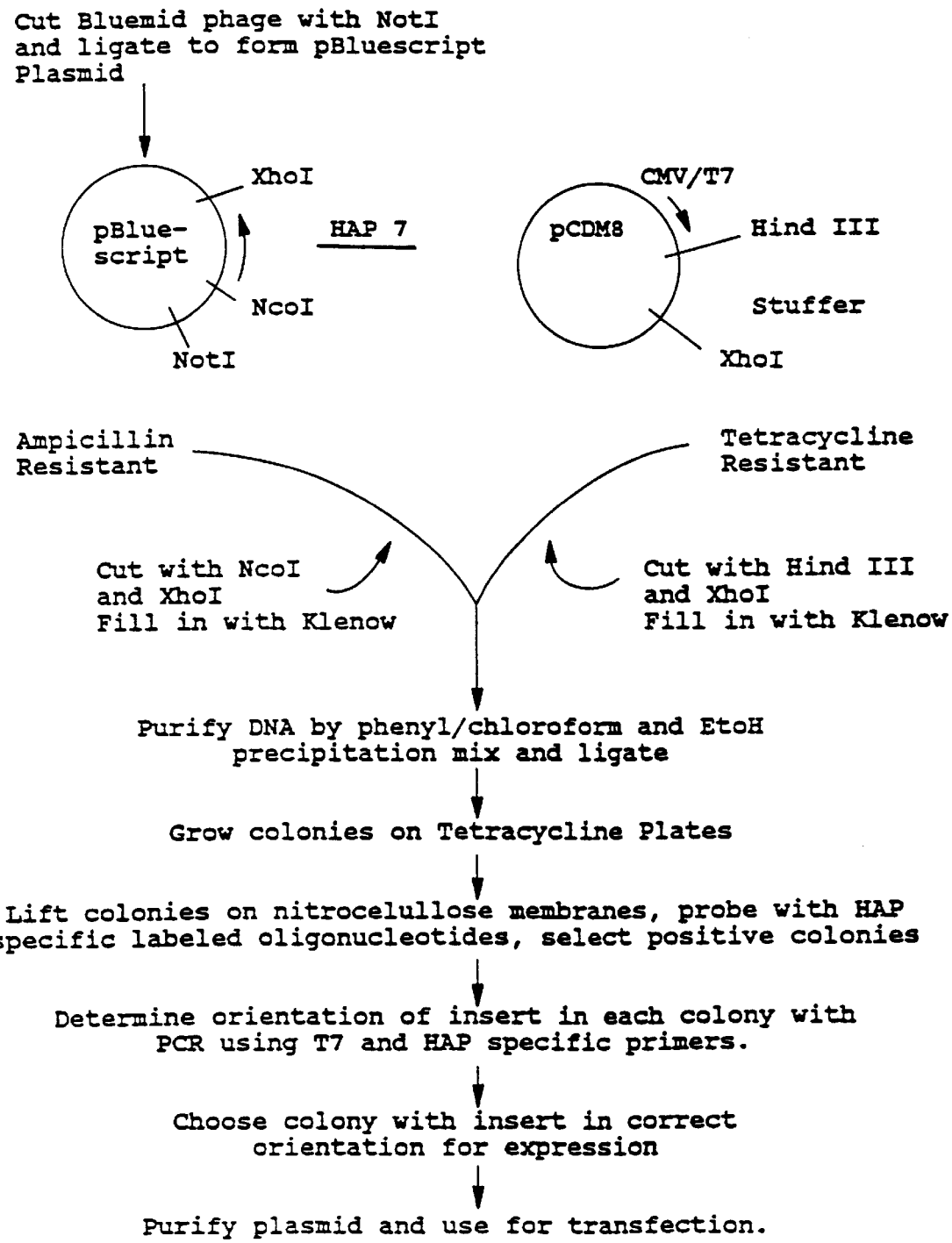
FIG. 12 is a flowchart of a procedure followed for preparing a plasmid useful in expression of a growth hormone releasing hormone receptor in a mammalian cell line.

FIG. 12 illustrates the steps followed to insert the HAP 7.3 cDNA sequence into the pCDM8 plasmid for use in transfection of COS cells. This scheme takes advantage of the NcoI restriction site containing the start codon (ATG) and different antibiotic resistances of the pBluescript® and pCDM8 plasmids.

Sequencing of HAP clones can be performed by the dideoxy chain termination method of Sanger using a commercially available kit, or on an automated DNA Sequencer.

The nucleotide sequence for the HAP 7.3 cDNA encoding a GHRH-R is illustrated in SEQ ID NO:7, and its corresponding amino acid sequence is shown in SEQ ID NO:8. A computer search (FASTAst GenBank Release 71) shows that, other than receptors from the secretin family, the sequence has no significant similarity to other known proteins.

EXPRESSION OF HAP 7.3 cDNA IN A MAMMALIAN CELL LINE

The HAP 7 cDNA contains an extended translation open reading frame (ORF) that begins with the methionine (Met) codon that conforms to the initiation codon consensus sequence proposed by Kozak. See "An Analysis of 5'-Noncoding Sequences From 699 Messenger RNAs," *Nucleic Acids Res.*, 15:8125–8148 (1988). The HAP 7 cDNA contains 80 base pairs 5' to this putative initiation codon, and is devoid of either ATG or inframe termination codons. The ORF extends 1,269 bp, and thus encodes a protein of 423 amino acids (predicted molecular weight of approximately 45 kDa). The HAP 7.3 cDNA was subcloned into the pCDM8 expression vector by taking advantage of the Nco1 restriction endonuclease site containing the putative initiation codon.

Figure 15:
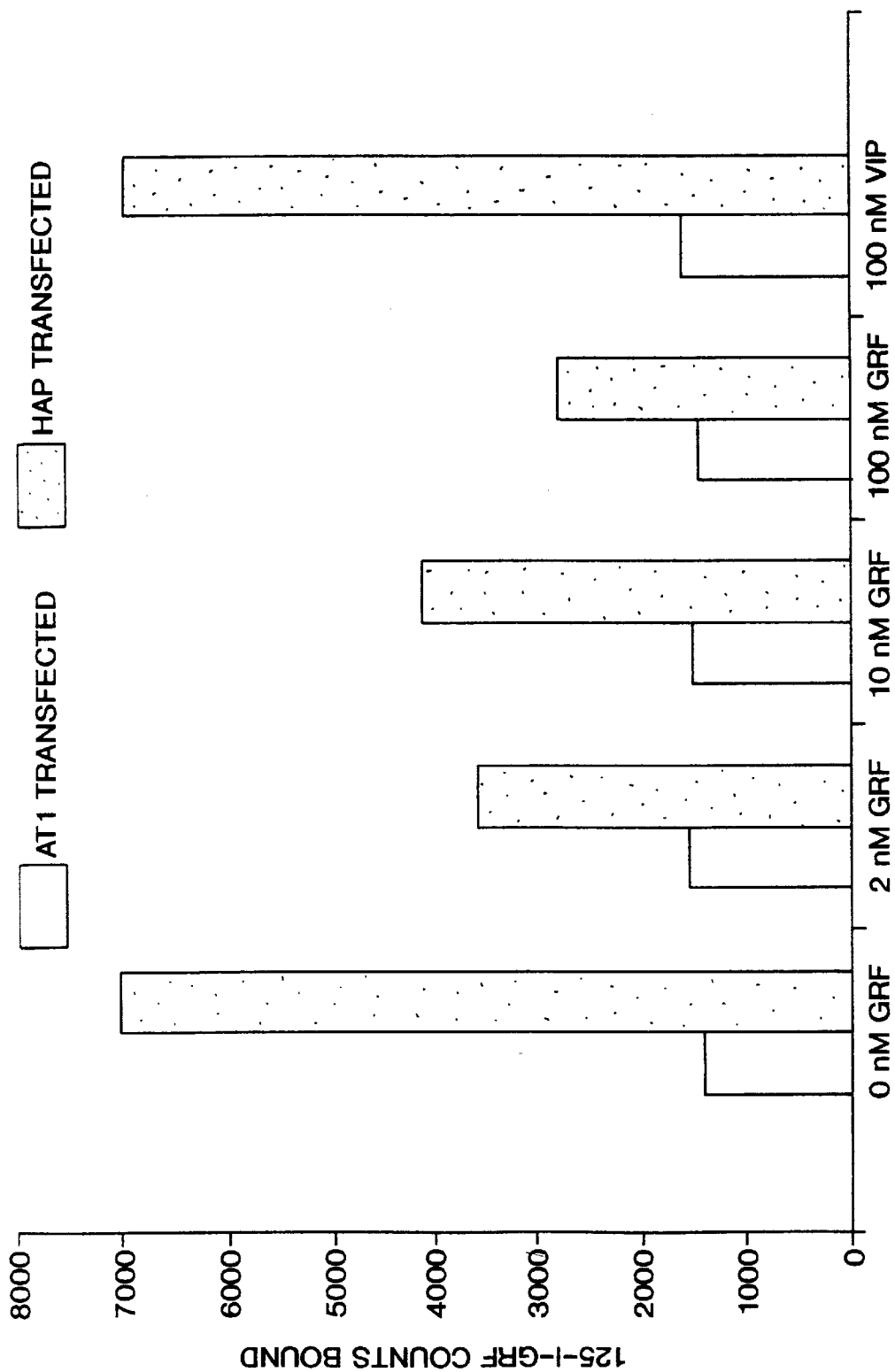
FIG. 15 is a bar chart demonstrating binding of $^{125}$I-GHRHa to COS cells transfected with either angiotensin AT$_1$ or HAP containing vectors. The bars indicate the total counts bound to the cells after incubation with $^{125}$I-GHRHa or in the presence of gradually increasing amounts of non-iodinated GRF. Incubation of the COS cells with $^{125}$I-GHRHa in the presence of 100 nM VIP had no effect on bound counts of GHRHa.
Figure 16:
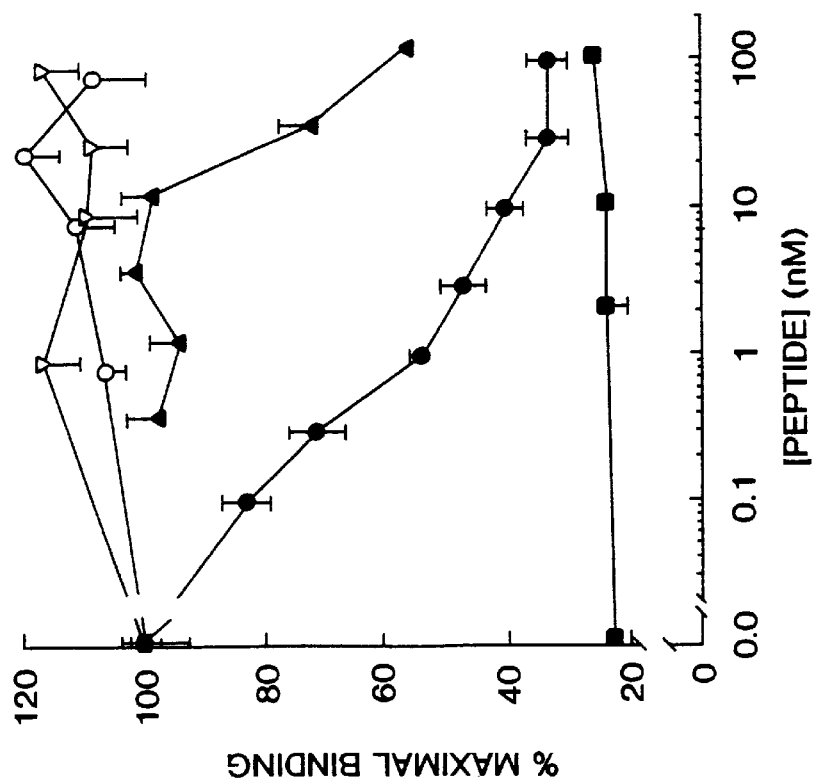
FIG. 16 illustrates the binding of iodinated GHRHa to cell membranes transfected with pCDM8 containing either the HAP 7 cDNA or the gene encoding for the rat angiotensin receptor. Binding in the presence of increasing concentrations of competing peptides is shown. Solid circles represent binding in the presence of uniodinated GHRH to membranes formed from cells transfected with a gene (HAP 7) encoding a GHRH-R. Squares represent binding in the presence of uniodinated GHRH to membranes formed from cells transfected with a gene encoding for rat angiotensin receptor. Solid triangles represent binding in the presence of PACAP to membranes formed from cells transfected with a gene (HAP 7) encoding a GHRH-R, open triangles represent binding in the presence of VIP, and open circles represent binding in the presence of secretin. Each point represents an N of 6±standard error. Non-specific binding was 20–30% of total counts in COS cell membranes, and 40–60% in crude pituitary membranes.

Cos-1 cells were transfected with the vector formed by splicing pCDM8 and HAP cDNA, and Cos-1 cell membranes were prepared 72 hours subsequently. Cos-1 cells were transfected using 10 μg of plasmid DNA per $6 \times 10^5$ cells in a 100-mm dish using the DEAE-dextran method described by Cullen. See "Use of Eukaryotic Expression Technology and the Functional Analysis of Cloned Genes," *Methods Enzymol.*, 152:684–704 (1987). COS cell cultures were transfected in parallel with pCDM8 containing a cDNA encoding the rat $AT_1$ angiotensin II receptor. COS cell membranes transfected with HAP cDNA, but not angiotensin receptors cDNA transfected COS cells, showed specific, high-affinity binding of $His^1$, $^{125}I\text{-}Tyr^{10}$,$Nle^{27}$ human GHRH(1–29)$NH_2$. With reference to FIGS. 15 and 16, the binding of iodinated GHRH, to COS cell membranes transfected with pCDM8 containing the HAP 7 cDNA, and iodinated GHRH binding to membranes transfected with pCDM8 containing a cDNA encoding the rat angiotensin II receptor is illustrated, and this binding compared to GHRHa binding in the presence of varying concentrations of competing peptides.

FIG. 15 is based on a lower number of samples, and due to high noise, it appears that the 2 nM GRF displaces a greater amount $^{125}$I-GRF than 10 nM GRF. However, the higher number of samples reflected in each data point in FIG. 16 show a direct correlation between the concentration of competing peptide added and the decrease in total bound counts of iodinated GRF analog.

FIG. 16 illustrates that PACAP competed for iodinated GHRH binding, although at much higher concentrations (Ki of approximately 30 nM). Binding of iodinated GHRH was unaffected by 100 nM of other peptides, including VIP, secretin, glucagon, calcitonin, galanin, parathyroid hormone, gastrointestinal peptide, PHM, and somatostatin, or one µM growth hormone releasing peptide. Since GHRH did not bind to the COS control cells transfected with the gene encoding for angiotensin, it is clear that the GHRH binding in the COS cells transfected with pCDM8 containing the HAP 7 cDNA is due to the expression of protein by the HAP 7 cDNA. Further, the GHRH specific binding activity demonstrated in FIGS. 15 and 16 illustrates that the protein produced by expression of the HAP 7 gene has all the binding characteristics of a GHRH-R.

Figure 17:
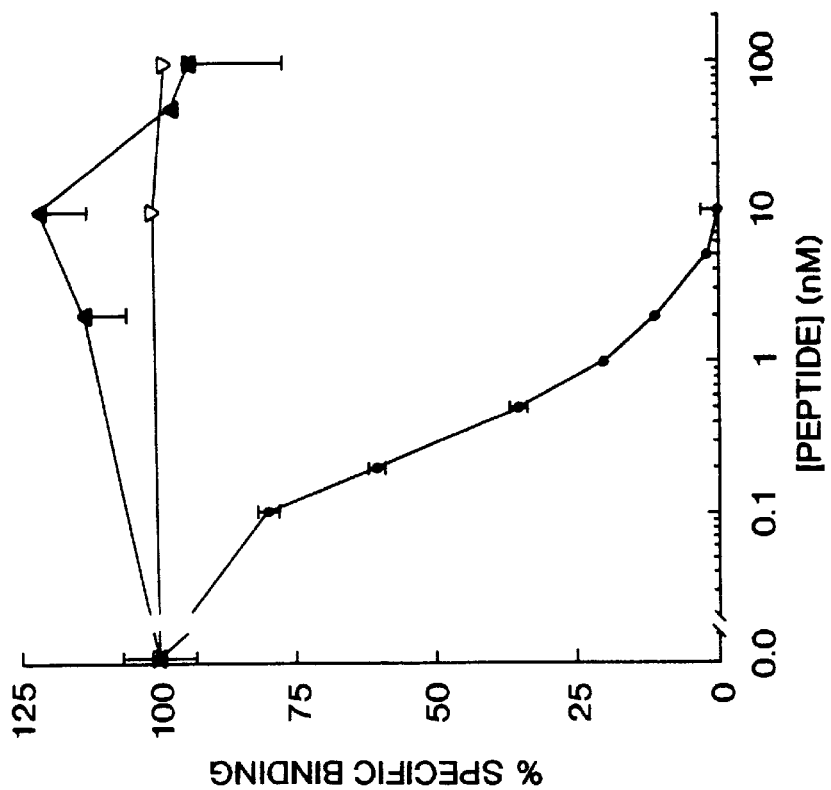
FIG. 17 illustrates the binding of $^{125}$1-GHRHa in ovine pituitary in the presence of gradually increasing concentrations of competing peptides. Solid circles represent GHRHa, solid triangles represent PACAP, and open triangles represent VIP.

FIG. 17 shows binding and displacement of the same GHRH analog in ovine pituitary membranes. This data gave a $K_D$ for GHRH binding in pituitary of 0.2 nM. Comparison with FIG. 16 suggests that a comparable high affinity site is induced in transfected COS cells, but that some of the sites may have lower affinity. This is expected because the abundance of G proteins in transfected cells is probably insufficient to allow complete receptor coupling, but this could also be due to some other factor in the artificial COS cell expression system. PACAP, but not VIP, showed significant displacement of GHRH in ovine pituitary at 500 nM and 1M.

There are several pieces of evidence which confirm that a GHRH-R gene has been cloned: The molecular weight of the protein encoded by the cloned gene closely matches the results from photoaffinity cross-linking of the ovine pituitary GHRH receptor, which showed a size of about 42 kDa after deglycosylation. The amino acid sequence of the cloned gene shown as SEQ ID NO:8, includes 423 amino acid residues. If the first 22 amino acid residues are a signal peptide which is removed by processing in the cell, this leaves a 401 amino acid protein having a molecular weight of approximately 44 kDa, which matches closely with the size determined in the photo affinity cross-linking in deglycosylation studies above.

Figure 18:
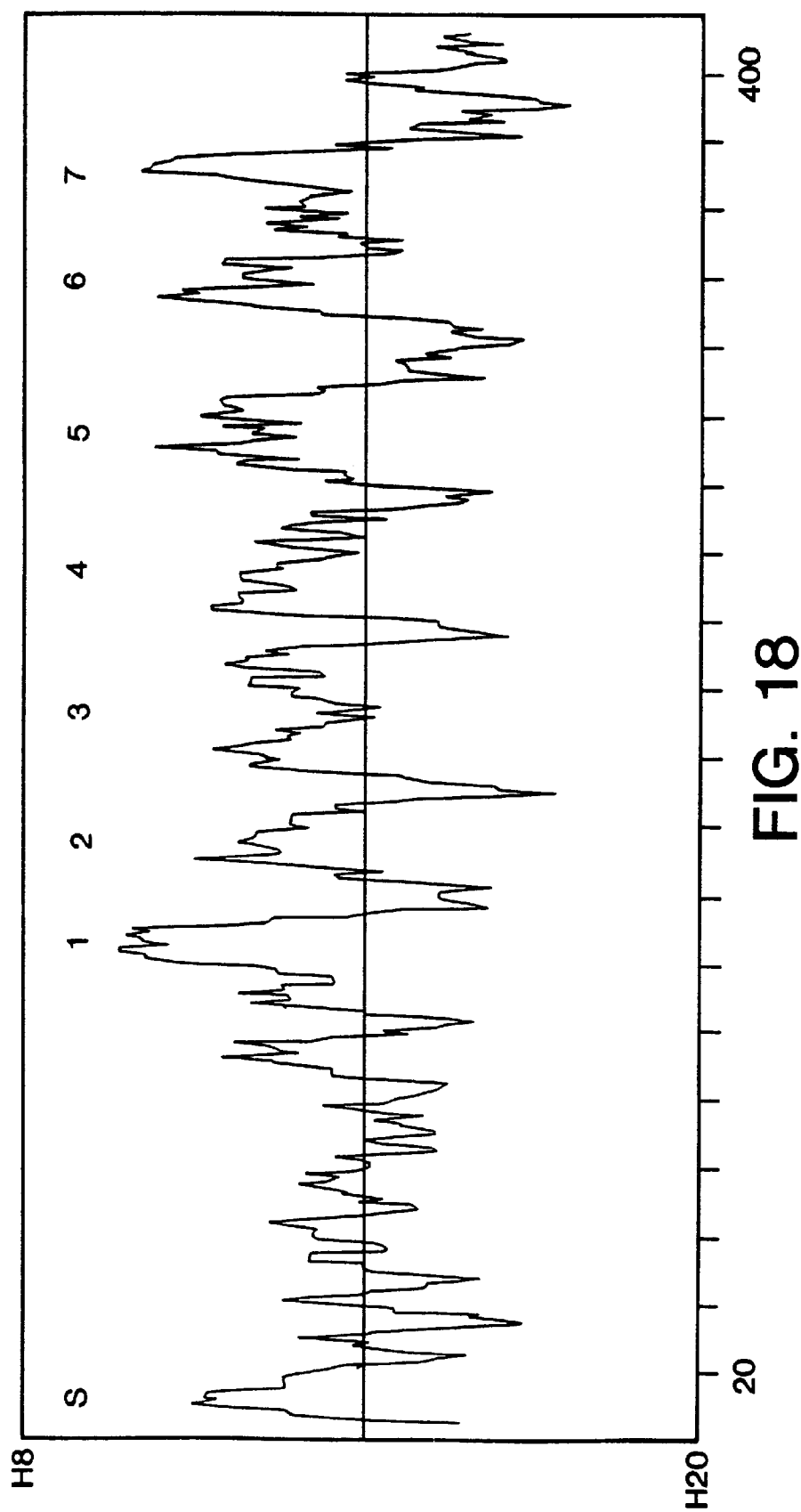
FIG. 18 is a hydropathy plot of the amino acid sequence shown as SEQ ID NO:8; S indicates putative signal peptide, and 1–7 indicate putative transmembrane spanning helices.

The protein sequence encoded by the cloned gene includes possible membrane spanning domains which exhibit the hydropathy signature of a G-protein-linked receptor. For example, FIG. 18 is a hydropathy plot of the amino acid sequence of SEQ ID NO:8, and has seven possible transmembrane regions. The graph is prepared by determining the running average of 9 amino acid residue polarities; points below the horizontal center line reflect polar or hydrophilic portions of the protein, while portions above the line indicate non-polar or hydrophobic portions of the protein which are likely to serve as transmembrane segments.

Table 1 below illustrates the percent amino acid residue identity found in receptor sequences believed to be similar to GHRH-R (e.g., VIP and secretin) via a computer matching algorithm, known as FASTA. See Pearson et al., *Proc. Natl. Acad. Sci. USA*, 85:2444–2448 (1988)

TABLE I

PERCENT AMINO ACID IDENTITY OF SELECTED RECEPTOR PROTEINS WITH HAP 7.3 IN COMPUTER SELECTED REGION OF OVERLAP

|  | VIP | Secretin | Calcitonin | PTH |
|---|---|---|---|---|
| HAP 7.3 Overlap | 47% 387 bp | 42% 388 bp | 35% 262 bp | 28% 367 bp |

TABLE II

PERCENT AMINO ACID RESIDUE IDENTITY IN RECEPTORS BELIEVED TO BE SIMILAR TO GHRH-R

| | Receptor Transmembranes TM5, TM6 and TM7 | | | |
|---|---|---|---|---|
| | PTH | SEC | VIP | HAP |
| CTR | 49% | 43% | 45% | 45% |
| PTH |  | 52% | 60% | 57% |
| SEC |  |  | 73% | 68% |
| VIP |  |  |  | 73% |

Table II demonstrates that the gene cloned from HAP is slightly more like the VIP receptor than the secretin receptor, and less like the PTH and calcitonin receptors (e.g., has significant homology to other G-protein linked receptors).

From the foregoing, it is clear that a gene encoding for a protein having GHRH-R activity has been cloned and expressed.

Thus, the present invention involves the solubilization, purification, and protein sequencing of a growth hormone releasing hormone receptor and biologically active fragments thereof, and also involves the cloning of a gene encoding for a growth hormone releasing hormone receptor and biologically active fragments thereof. In a preferred embodiment, the receptor nucleotide sequence obtained from a human acgromegalic pituitary tumor, cDNA Library, is inserted into a vector, such as but not limited to a pBluescript plasmid; this plasmid is used to transform a suitable host cell, such as bacteria in a viable culture; for example, the bacteria stored in the American Type Culture Collection in Rockville, Md. as Accession Number ATCC 69058. The bacteria stored at the ATCC can be obtained, the nucleotide sequence for a GHRH receptor can be excised from the bacterial plasmid using restriction endonucleases, by way of non-limiting example XbaI and XhoI, and the nucleotide sequence used to express protein in another organism or cell line, such as but not limited to COS cells. Thus, the transformed bacteria stored at the ATCC (as Accession Number 69058) is useful for further cloning of the nucleotide sequence encoding a GHRH receptor, and the nucleotide sequence encoding a GHRH receptor can be utilized to express protein, which can be used for screening of a variety of drugs which interact with G-protein-linked receptors, such as the GHRH-R, and can also be used for the therapeutic treatments mentioned above

MOLECULAR CLONING OF THE OVINE PITUITARY GHRH-R

Cloning of the Ovine Pituitary GHRH Receptor

We employed various conventional techniques in attempts to obtain the ovine GHRH-R sequence by screening an ovine pituitary library with human GHRH-R as a random-primed DNA probe template. We also tried to obtain the ovine sequence using PCR directly on the full ovine library using degenerate primers and primers specific to the human GHRH-R sequence, but this only yielded several GHRH-R fragments. Thus, performing PCR on the full library indicated a part of the GHRH receptor, but could not be used to obtain the full sequence.

We were able to successfully clone the ovine pituitary GHRH-R only by combining library subdivision, a technique not heretofore employed in hybridization screening but commonly used in expression cloning, with PCR and hybridization screening. Thus, we developed a unique hybridization screening protocol, discussed in detail below. In summary, our protocol comprises the steps of: (1) subdividing a library into pools; (2) using PCR on each library pool to identify a pool exhibiting a signal; and (3) using a random-primed DNA probe template to perform hybridization screening on that pool. Screening was carried out using a commercially available hybridization buffer, such as RAPID HYB® from Amersham International plc.

In particular, we employed the following protocol to clone the ovine pituitary GHRH-R: (1) subdividing an ovine library into pools; (2) using PCR on each library pool to identify a pool exhibiting a GHRH receptor signal; and (3) using human GHRH-R as a random-primed DNA probe template to perform hybridization screening on that pool. Screening was carried out using a commercially available hybridization buffer, such as RAPID HYB® from Amersham International plc.

First, an oligo dT primed cDNA library was constructed from adult female ovine pituitary. Then the library was subdivided into 30 different pools. As discussed above, while subdivision has been used in expression cloning techniques, it is not typically employed in hybridization screening. Due to low abundance of the GHRH receptor, expression cloning cannot be used to isolate and sequence the GHRH-R.

Next, PCR was performed on each of the 30 library pools in order to amplify GHRH-R in the each sample and identify a sample that exhibited a GHRH receptor signal. Using PCR allowed us to check each pool to identify a pool that exhibited a GHRH receptor signal. PCR is not normally used in combination with library subdivision and hybridization screening. Thus, by subdividing the library into pools and using PCR on each pool, we were able to reduce the number of competing signals and identify a pool exhibiting a GHRH-R signal.

Then, hybridization screening was performed on the identified pool using human GHRH-R as a random-primed DNA probe template and a hybridization buffer to obtain the full length clone. After screening $3 \times 10^6$ clones in the identified pool, three different clones encoding GHRH-R were obtained. Only one of the three clones encoded the full length ovine GHRH-R sequence, as set forth in FIG. 19.

Results

The ovine GHRH-R sequence we obtained, shown in FIG. 19, encodes a putative seven trans-membrane G protein-coupled receptor. The ovine GHRH-R is structurally related to the porcine, human, rat and mouse GHRH-R with nucleotide identity of 88.8, 83.7, 79.1 and 78.5%, respectively. In addition, the amino acid sequence identity with porcine, human, rat and mouse is 84.9, 83.0, 78.0 and 75.4%, respectively. The ovine GHRH-R sequence is less homologous to human VIP, PACAP and secretin receptors (58.9, 59.9 and 57.7%, respectively). Transient expression of this ovine GHRH receptor demonstrated functional coupling to cAMP.

Figure 20B:
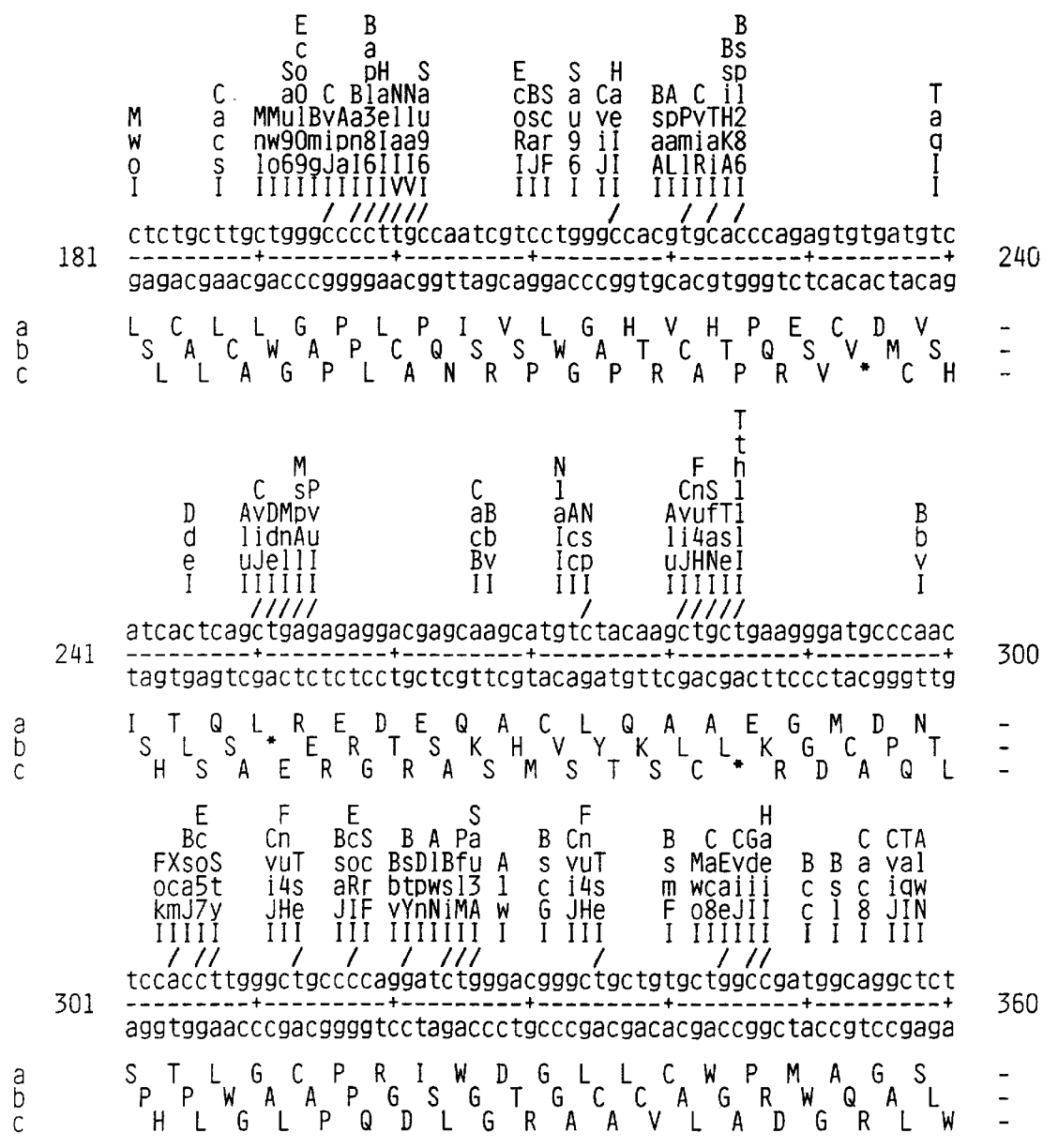
Figure 20D:
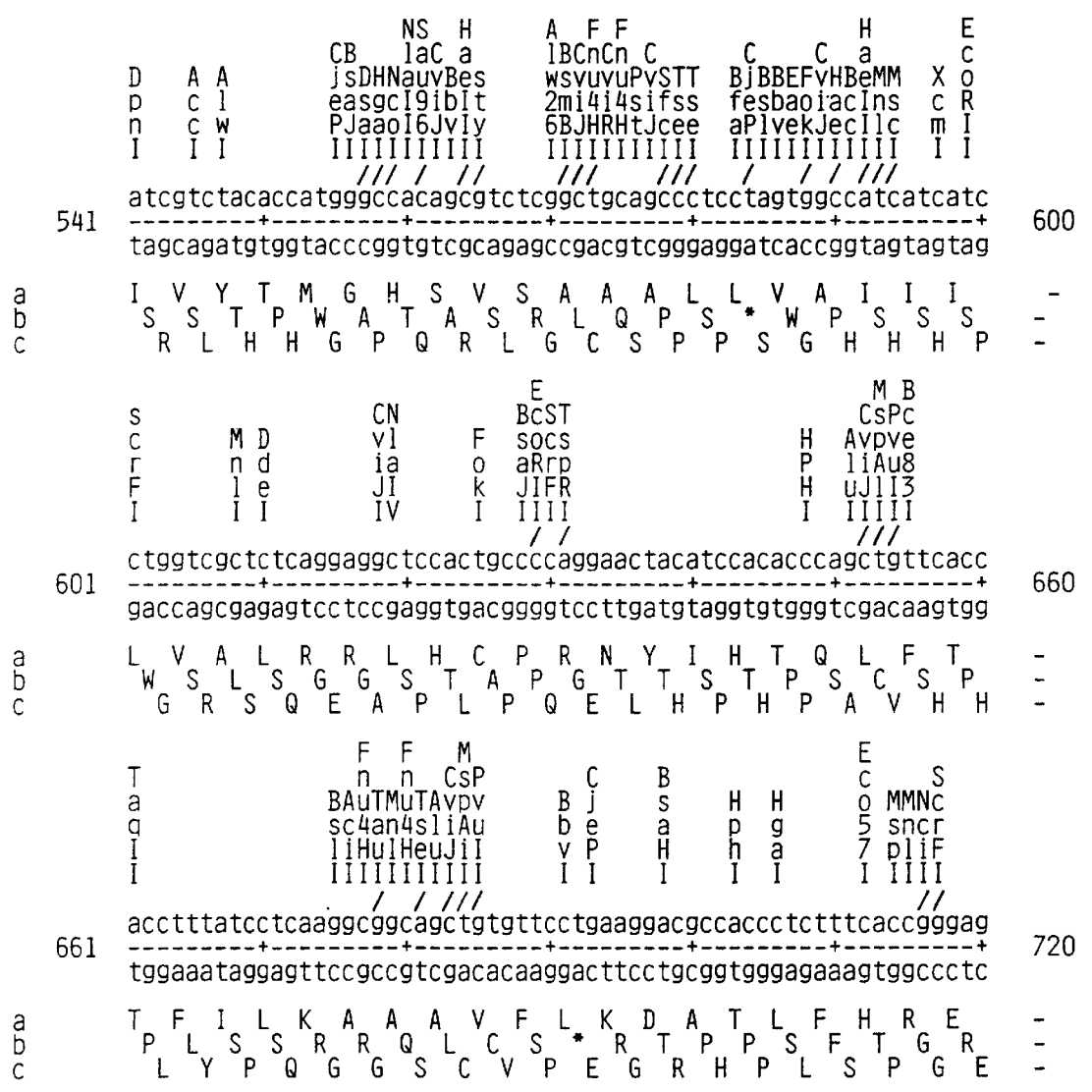

FIG. 20 illustrates locations on the ovine GHRH-R sequence illustrated in FIG. 19 that are cut by restriction enzymes. The following restriction enzymes cut the ovine receptor sequence:

| AccI | AceIII | AciI | AhdI | AluI | AlwI | Alw26I | AlwNI |
|---|---|---|---|---|---|---|---|
| ApaI | ApaLI | ApoI | AvaI | AvaII | BanI | BanII | BbsI |
| BbvI | BccI | Bce83I | BcefI | BogI | BfaI | BfiI | BglI |
| BglII | BmgI | BplI | BpmI | Bpu10I | BsaAI | BsaHI | BsaJI |
| BsaXI | BsoGI | BseRI | BsgI | BsiHKAI | BslI | BsmBI | BsmFI |
| Bsp1286I | BspGI | BspMI | BsrI | BsrDI | BssSI | BstYI | Cac8I |
| CjeI | CjePI | CviJI | CviRI | DdeI | DpnI | DrdII | DsaI |
| EaeI | EarI | EciI | Eco57I | EcoNI | Eco0109I | EcoRI | EcoRII |
| FauI | Fnu4HI | FokI | GdiII | HaeI | HaeII | HaeIII | HgaI |
| HhaI | Hin4I | HincII | HinfI | HphI | MaeIII | MboII | MmeI |
| MnlI | MscI | MslI | MspI | MspAII | MwoI | NarI | NciI |
| NcoI | NlaIII | NlaIV | NruI | NspI | PflMI | PleI | PmlI |
| PpuMI | PstI | PvuII | RleAI | RsaI | SacII | SapI | Sau96I |
| Sau3AI | ScaI | ScrFI | SfaNI | SfcI | SimI | SspI | SstI |
| StuI | StyI | TaiI | TaqI | TaqII | TatI | TauI | TfiI |
| ThaI | TseI | Tsp45I | Tsp4CI | Tsp509I | TspRI | TthlllII | XcmI |
| XhoI | | | | | | | |

The following restriction enzymes do not cut the ovine GHRH-R sequence:

| AatII | AflII | AflIII | ApaBI | AscI | AvrII | BaeI | BaeI |
|---|---|---|---|---|---|---|---|
| BamHI | BclI | Bpu1102I | BsaI | BsaBI | BsaWI | BsbI | BsiEI |
| BsmI | Bsp24I | Bsp24I | BspEI | BspLU11I | BsrBI | BsrFI | BsrGI |
| BssHII | Bst1107I | BstEII | BstXI | Bsu36I | ClaI | DraI | DraIII |
| DrdI | EagI | Eco4III | EcoRV | FseI | FspI | HgiEII | HindIII |
| HpaI | KpnI | MluI | MseI | MunI | NdeI | NgoAIV | NheI |
| NotI | NsiI | NspV | PacI | Pfl1108I | PinAI | PmeI | PshAI |
| Psp1406I | PvuI | RcaI | RsrII | SalI | SanDI | SexAI | SfiI |
| SgfI | SgrAI | SmaI | SnaBI | SpeI | SphI | SrfI | Sse8387I |
| Sse8647I | SunI | SwaI | TthlllI | UbaDI | VspI | XbaI | XmnI |

The ovine GHRH-R provides an important tool for studying the GHRH binding site. As shown in FIG. 21, the ovine sequence differs from other known GHRH-R sequences, such as porcine, human, rat and mouse, in that the ovine GHRH-R has 16 amino acids deleted from its C-terminus. RT-PCR analysis was conducted for independently prepared ovine pituitary mRNA and confirmed that this truncated receptor is the dominant form of receptor mRNA expressed in ovine pituitary and is not a cloning artifact. A missing receptor domain has been reported to play a key role in the down regulation of related receptors. Accordingly, regulation of the ovine receptor may be different, and may be susceptible to different means of pharmacological intervention, from that of other known receptors (porcine, human, rat and mouse). Also, related receptors may be similarly truncated and have regulation mechanisms similar to that of the ovine receptor and different from that of other known receptors. For example, sheep and cows are closely related (they are classified in the same suborder). Therefore, the bovine GHRH-R may be similarly truncated and regulated.

In addition, we have studied photoaffinity crosslinking to the expressed ovine clone and compared it to crosslinking in ovine pituitary membranes. In both cases, the deglycosylated GHRH-R protein appears the same size. This further confirms that the truncated receptor protein we have cloned is not an artifact, but is the major form of the receptor found in ovine pituitary.

From the above teachings, it is apparent that many modifications and variations of the present invention are possible. By way of non-limiting example, it is contemplated that other complexes of GHRH-R in crude pituitary samples can be bound to affinity columns in order to produce purified GHRH-R. It is therefore to be understood that the invention may be practiced otherwise than as specifically described.

We claim:

1. A purified and isolated nucleic acid molecule having the nucleic acid sequence of SEQ ID NO:9 of the ovine growth hormone receptor.

2. A purified and isolated nucleic acid molecule encoding the amino acid sequence of SEQ ID NO:10 of the ovine growth hormone releasing hormone receptor.

3. A nucleic acid molecule having the nucleic acid sequence SEQ ID NO:9 encoding an ovine growth hormone releasing hormone receptor, prepared according to the following process:

(a) preparing an ovine pituitary library;

(b) subdividing the library into pools;

(c) performing PCR on each pool to identify a pool that exhibits a growth hormone releasing hormone receptor signal; and (d) performing hybridization screening on the pool identified in step (c) using a hybridization buffer and a detectable labeled growth hormone releasing hormone receptor DNA oligonucleotide probe to obtain the nucleic acid molecule encoding the ovine growth hormone releasing hormone receptor.

* * * * *